(12) United States Patent
Barrett et al.

(10) Patent No.: US 9,522,177 B2
(45) Date of Patent: *Dec. 20, 2016

(54) ANTIMICROBIAL AND IMMUNOSTIMULATORY SYSTEM COMPRISING AN OXIDOREDUCTASE ENZYME

(71) Applicant: Institute of Technology Sligo, Sligo (IE)

(72) Inventors: John Reginald Barrett, Sligo (IE); James Joseph Brennan, Sligo (IE); Thomas Patrick Patton, Sligo (IE)

(73) Assignee: INSTITUTE OF TECHNOLOGY SLIGO, Sligo (IE)

( * ) Notice: Subject to any disclaimer, the term of this patent is extended or adjusted under 35 U.S.C. 154(b) by 33 days.

This patent is subject to a terminal disclaimer.

(21) Appl. No.: 13/721,752

(22) Filed: Dec. 20, 2012

(65) Prior Publication Data

US 2014/0023597 A1    Jan. 23, 2014

Related U.S. Application Data

(63) Continuation of application No. 12/444,231, filed as application No. PCT/IE2007/000094 on Oct. 5, 2007, now abandoned.

(30) Foreign Application Priority Data

Oct. 6, 2006 (GB) .................. 0619786.7

(51) Int. Cl.
| | | |
|---|---|---|
| *A61K 38/44* | (2006.01) | |
| *A61K 31/7004* | (2006.01) | |
| *A61K 33/40* | (2006.01) | |
| *A61K 9/00* | (2006.01) | |
| *A61K 8/22* | (2006.01) | |
| *A61K 8/60* | (2006.01) | |
| *A61K 8/66* | (2006.01) | |
| *A61L 15/32* | (2006.01) | |
| *A61L 15/38* | (2006.01) | |
| *A61L 15/46* | (2006.01) | |
| *A61L 26/00* | (2006.01) | |
| *A61Q 17/00* | (2006.01) | |
| *A61Q 19/00* | (2006.01) | |

(52) U.S. Cl.
CPC .............. *A61K 38/443* (2013.01); *A61K 8/22* (2013.01); *A61K 8/60* (2013.01); *A61K 8/66* (2013.01); *A61K 9/0056* (2013.01); *A61K 31/7004* (2013.01); *A61K 33/40* (2013.01); *A61L 15/32* (2013.01); *A61L 15/38* (2013.01); *A61L 15/46* (2013.01); *A61L 26/0033* (2013.01); *A61L 26/0066* (2013.01); *A61Q 17/005* (2013.01); *A61Q 19/00* (2013.01); *C12Y 101/03004* (2013.01); *A61L 2300/11* (2013.01); *A61L 2300/254* (2013.01); *A61L 2300/404* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 4,537,764 A | 8/1985 | Pellico et al. | |
| 4,576,817 A | 3/1986 | Montgomery et al. | |
| 4,578,265 A | 3/1986 | Pellico et al. | |
| 4,839,156 A | 6/1989 | Ng et al. | |
| 4,844,898 A | 7/1989 | Komori et al. | |
| 4,950,475 A * | 8/1990 | Vishnupad et al. | 514/772.3 |
| 5,098,303 A | 3/1992 | Fischer | |
| 5,262,151 A * | 11/1993 | Montgomery | A61Q 11/00 424/50 |
| 5,336,494 A | 8/1994 | Pellico | |
| 5,453,284 A | 9/1995 | Pellico | |
| 5,607,681 A * | 3/1997 | Galley et al. | 424/405 |
| 2003/0228264 A1 | 12/2003 | Perna | |
| 2006/0034816 A1* | 2/2006 | Davis et al. | 424/94.4 |

FOREIGN PATENT DOCUMENTS

| | | |
|---|---|---|
| WO | WO-8802600 A1 | 4/1988 |
| WO | WO-9638548 A1 | 12/1996 |
| WO | WO-9965538 A1 | 12/1999 |
| WO | WO-02080861 A1 | 10/2002 |
| WO | WO-03090800 A1 | 11/2003 |

OTHER PUBLICATIONS

David W. Ball. The Chemical Composition of Honey. Journal of Chemical Education vol. 84 No. 10 Oct. 2007. pp. 1643-1646.*
J. W. White, Jr. and Landis W. Doner. Beekeeping in the United States: Agriculture Handbook No. 335, Revised Oct. 1980. pp. 1-12.*
Katrina Brudzynski. Effect of hydrogen peroxide on antibacterial activities of Canadian honeys. Can. J. Microbiol. 52: 1228-1237 (2006).*
Wahdan, Causes of the Antimicrobial Activity of Honey, Infection, 26(1): 30/26-35/31 (1998).
International Preliminary Report on Patentability for PCT/IE2007/000094, mailed on Jan. 19, 2009.

(Continued)

*Primary Examiner* — Frederick Krass
*Assistant Examiner* — Michael P Cohen
(74) *Attorney, Agent, or Firm* — VLP Law Group LLP; Richard G. A. Bone

(57) ABSTRACT

The present invention relates to an antimicrobial and immunostimulatory system, applications thereof and a process for the production of the antimicrobial and immunostimulatory system. The present invention provides a storage-stable antimicrobial and immunostimulatory system comprising an oxidoreductase enzyme, a substrate for the oxidoreductase enzyme and hydrogen peroxide in an aqueous solution wherein the substrate for the oxidoreductase enzyme is present up to 90% by weight and water is present up to 20% by weight based on the weight of the total composition; the system has a pH from approximately 4 to 8; and the system provides a two-stage hydrogen peroxide release.

21 Claims, 48 Drawing Sheets

(56) References Cited

OTHER PUBLICATIONS

UKIPO Search Report for priority application GB0619786.7, Feb. 12, 2007.
pH table of bases downloaded Jun. 12, 2012 from http://www.engineeringtoolbox.com/bases-ph-d_402.html.
International Search Report for PCT/IE2007/000094, mailed Mar. 10, 2008.
Molan, The antibacterial activity of honey 1. The nature of the antibacterial activity, Bee World, 1-2: 5-29 (1992).
White et al.,The identification of inhibine, the antibacterial factor in honey, as hydrogen peroxide and its origin in a honey glucose-oxidase system, Biochim Biophys Acta, 73: 57-70 (1963).
French et al., The antibacterial activity of honey against coagulase-negative staphylococci, Journal of Antimicrobial Chemotherapy, 56: 228-231 (2005).
Brady, N.F. et al., The Sensitivity of Dermatophytes to the Antimicrobial Activity of Manuka Honey and Other Honey, Pharmaceutical Sciences, 2: 471-473 (1996).
Brudzynski, K., Effect of hydrogen peroxide on antibacterial activities of Canadian honeys, Canadian Journal of Microbiology, 52: 1228-1237 (2006).
Gupta, A.K. et al., An Overview of Topical Antifungal Therapy in Dermatomycoses, Drugs, 55(5): 645-674 (1998).
White, J.W. and Doner, L.W., Beekeeping in the United States Agriculture Handbook, 335: 1-12 (1980).
Bang, L. M., et al., "The Effect of Dilution on the Rate of Hydrogen Peroxide Production in Honey and Its Implications for Wound Healing", The Journal of Alternative and Complementary Medicine, 9:267-273 (2003).

* cited by examiner

Pseudomonas aeruginosa    Staphylococcus aureus    Escherichia coli

1. Silver containing Gel
2. Silver containing hydrocolloid
3. Non sterilised A³IS
4. Sterilised A³IS Sterilised A³IS.    Non sterilised A³IS.

ANTIMICROBIAL AND IMMUNOSTIMULATORY SYSTEM COMPRISING AN OXIDOREDUCTASE ENZYME

This application is a continuation of U.S. patent application Ser. No. 12/444,231, filed Jan. 19, 2010, which claims the benefit under 35 U.S.C. §371 of International Application No. PCT/IE2007/000094 (PCT Publication No. WO 2008/041218), filed Oct. 5, 2007, which claims priority to United Kingdom Patent Application No. 0619786.7, filed Oct. 6, 2006, the entire contents of each of which is hereby incorporated herein by reference.

FIELD OF THE INVENTION

The present invention relates to an antimicrobial and immunostimulatory system, applications thereof and a process for the production of the antimicrobial and immunostimulatory system.

BACKGROUND TO THE INVENTION

Well-known antimicrobial compositions include conventional treatments such as antiseptics and antibiotics. Other treatments include silver-containing gels, compounds containing heavy metals and solutions of hydrogen peroxide and natural and synthetic pharmaceutically active substances. However, treatments such as antibiotics have disadvantages because of the emergence of antibiotic resistance. Furthermore, high levels of hydrogen peroxide have a toxic effect. In addition, hydrogen peroxide in solution is typically unstable and it is difficult to provide a sustained delivery system for this material. Thus, for a wide variety of different reasons, conventional antimicrobial treatments have many drawbacks.

Additionally, there are a number of naturally occurring antimicrobial systems known which rely on the ability of certain oxidising agents to disrupt metabolic processes of bacteria, fungi and viruses. For example, WO 03/090800 is directed to wound dressings comprising hydrated hydrogels and enzymes. Specifically, this patent describes the need to keep the enzyme substrate physically separated from the oxidoreductase enzyme prior to the use of the dressing. This prevents an unwarranted reaction which according to WO 03/090800 is undesirable. Thus, the wound dressing of WO 03/090800 can only function when it has been used or applied to a wound i.e. after it has been brought in contact with an appropriate enzyme substrate.

Additionally, in recent years there has been a resurgence of interest in the therapeutic efficacy of honey, particularly in the area of wound healing. As a natural product, honey offers an attractive alternative to conventional treatments. Even though honey has been used for hundreds of years as a treatment for wounds, it is only relatively recently that the antibacterial properties of honey have been researched. This research has postulated that the antibacterial activity of honey is due to several key properties including high osmotic pressure, low water content, available water (Aw), low pH resulting in an acidic environment, glucose oxidase system which results in the formation of hydrogen peroxide, low protein content, high carbon to nitrogen ratio, low redox potential (Eh) due to high content of reducing sugars, chemical agents, pinocembrin, lysozyme, acids (phenolic), terpenes, benzyl alcohol and/or volatile substances (possibly phytochemicals influenced by bee enzymes).

Many different types of honey have antimicrobial activity. Over the past number of years Manuka honey has been recognised as having superior activity to most other honeys. Manuka honey is derived from the Manuka tree, *Leptospermum scoparium*, a native of New Zealand. Manuka honey is known for the treatment of wound infections and its antibacterial activity. It is the common perception in the field that Manuka contains a unique antibacterial factor and there is a wide body of research conducted to attempt to characterise this antimicrobial substance. Manuka honey has in recent years been tested in order to determine and quantify this antibacterial activity and unique antibacterial factor. Researchers in this field have found that when Manuka honey was subjected to catalase neutralization assays, where the amount of catalase added to Manuka honey samples was sufficient to destroy all hydrogen peroxide produced, antibacterial activity was still observed. This has resulted in the accepted perception in this field that there is a non-peroxide factor, referred to in the literature as Non-Peroxide Activity and Unique Manuka Factor (UMF), present in Manuka Honey causing this antibacterial activity. However, despite a significant amount of research aimed at identifying the substance(s) mediating the non-peroxide activity, or UMF, as yet, the precise nature of this activity is currently not known and no such substance has been clearly identified.

Some of the disadvantages associated with conventional treatments are outlined previously. Furthermore, natural honey as an antibacterial agent has several disadvantages. Firstly, natural honey is composed of a diverse mixture of identified and unidentified organic and inorganic compounds at various concentrations. In this respect it can be expected to demonstrate a degree of variability which may be unacceptable for its use in many clinical applications. Secondly, honey is mainly used for topical application. This is because when honey is diluted by, for example, absorption into the gut it becomes too diluted to have any detectable activity. Finally, honey is a natural product, which will have many additional compounds present and some of these compounds may give rise to an allergic reaction when it is applied. There is therefore a need for an antimicrobial system which overcomes the above-mentioned disadvantages and can provide antibacterial activity similar or better than natural honey. In particular, there is a need to carry out further research into the antibacterial role of Manuka honey in more detail in order to elucidate the mechanism of its antibacterial action.

Thus, there is therefore a need to research these conventional and natural treatments in order to generate further antimicrobial compositions which do not have the many disadvantages commonly associated with such treatments. Indeed, if the positive attributes of such conventional and natural treatments could be harnessed without the negative side effects or deleterious properties, this would result in a much improved alternative antibacterial system of significant medical and commercial importance.

STATEMENT OF THE INVENTION

According to a first aspect of the invention, there is provided a storage-stable antimicrobial and immunostimulatory system comprising an oxidoreductase enzyme, a substrate for the oxidoreductase enzyme and hydrogen peroxide in an aqueous solution;
  wherein the substrate for the oxidoreductase enzyme is present up to 90% by weight and water is present up to 20% by weight based on the weight of the total system;

the system has a pH from approximately 4 to 8; and the system provides a two-stage hydrogen peroxide release in which
(a) storage-stable endogenously produced hydrogen peroxide is bioavailable within the system at a level of at least 10 mg per liter for immediate release; and
(b) the sustained release of further hydrogen peroxide for at least a twenty-four hour period occurs upon rehydration of the system.

According to a second aspect of the invention, there is provided a system as defined herein for use in a method of therapy.

According to a third aspect of the invention, there is provided a system as defined herein for use in cosmetic applications.

According to a fourth aspect of the present invention, there is provided a method for treating a microbial infection and/or the repair and/or regrowth of damaged tissues and/or cells of a patient comprising the steps of applying an effective amount of the system as defined herein to an infected area of a patient by a topical, enteral and/or parenteral mode of administration.

According to a fifth aspect of the present invention, there is provided a process for manufacture of a storage-stable antimicrobial and immunostimulatory system comprising an oxidoreductase enzyme, a substrate for the oxidoreductase enzyme and hydrogen peroxide in an aqueous solution as defined herein wherein the process comprises the steps of
a. heating the water to a temperature of at least 60° C., preferably from approximately 75° C. to 95° C.;
b. adding the substrate for the oxidoreductase enzyme to the heated water to form a water-sugar solution,
c. cooling the water-sugar solution to a temperature below approximately 40° C. to allow retention of enzyme activity;
d. adding the oxidoreductase enzyme to the water-sugar solution of step (c) with stirring to form hydrogen peroxide at a pre-determined controlled rate; and
e. cooling the resultant mixture from step (d) to room temperature to produce a solution with bioavailable and storage-stable endogenously produced hydrogen peroxide at a level of at least 10 mg per liter for immediate release.

DETAILED DESCRIPTION OF THE INVENTION

In the specification, it will be understood that the term "antimicrobial" or "antibacterial" are used interchangeably herein and cover biocidal or biostatic activity against various types of micro-organisms including but not limited to bacteria, fungi, viruses, yeasts, parasitic or pathogenic microorgansims and/or moulds.

In the specification the term "by weight", "percentage by weight" or "w/w %" refers to the weight of the final composition or system. These w/w values are interchangeable with w/v.

According to the main aspect of the present invention, there is provided a storage-stable antimicrobial and immunostimulatory system comprising an oxidoreductase enzyme, a substrate for the oxidoreductase enzyme and hydrogen peroxide in an aqueous solution;
wherein the substrate for the oxidoreductase enzyme is present up to 90% by weight and water is present up to 20% by weight based on the weight of the total system;
the system has a pH from approximately 4 to 8; and the system provides a two-stage hydrogen peroxide release in which
(a) storage-stable endogenously produced hydrogen peroxide is bioavailable within the system at a level of at least 10 mg per liter for immediate release; and
(b) the sustained release of further hydrogen peroxide for at least a twenty-four hour period occurs upon rehydration of the system.

Advantageously, this system is a storage stable, single component system which is ready for immediate use and provides dual functionality in terms of antimicrobial and immunostimulatory activity. Furthermore, we have found that the system of the present invention has increased efficacy in terms of antimicrobial and immunostimulatory effect, when compared to Manuka honey and conventional antimicrobials, such as silver dressing.

The antimicrobial effect of the system of the present invention is mediated by the two-stage hydrogen peroxide release. Advantageously, the system of the present invention provides this two-stage hydrogen peroxide release in a regulated, defined and reproducible manner.

One of the main advantages of the present system is that it provides storage-stable hydrogen peroxide for immediate release. This endogenous reservoir provides an immediately available hydrogen peroxide and an immediate antimicrobial effect. This is one of the significant advantages of the present invention over natural honey and other known systems. Additionally, after re-hydration, the system provides for a second tier of hydrogen peroxide activity involving the sustained release of hydrogen peroxide for at least a twenty-four or forty-eight hour period.

According to a preferred embodiment of this aspect of the invention, the storage-stable endogenously produced hydrogen peroxide is bioavailable within the system at a level of at least 10, preferably 75 mg hydrogen peroxide per liter or parts per million for immediate release. However, it will be understood that the level of endogenously produced hydrogen peroxide which is immediately bioavailable within the system will depend on the amount of oxidoreductase enzyme present in the system. Hence, the level could be much greater than 10 or 75 mg of hydrogen peroxide per liter of the system if the level of oxidoreductase enzyme used is high. Thus, if the concentration of oxidoreductase enzyme and/or substrate for the oxidoreductase enzyme is increased, then the pool of endogenous hydrogen peroxide increases. For example, we have found that approximately 175 U of oxidoreductase enzyme per 100 g system generates an endogenous pool of approximately 10 mg hydrogen peroxide per liter. Furthermore, approximately 1400 U of oxidoreductase enzyme per 100 g system generates an endogenous pool of approximately 25 mg hydrogen peroxide per liter This initial endogenous reservoir of hydrogen peroxide present in the system is storage-stable and remains in the system until the second tier of hydrogen peroxide is released. This storage-stability aspect is another advantage of the present invention. In the context of this application, storage-stable means that the endogenously produced hydrogen peroxide is maintained within the system for a period of from approximately 3 months up to approximately 36 months. Furthermore, the system does not degrade, separate or lose activity during this time period. The expected shelf life for the system under normal conditions is approximately 36 months. In addition, the system when subject to sterilisation, for example by irradiation, does not deteriorate in quality or activity.

Upon use or application of the system of the present invention, a second-tier of hydrogen peroxide is released where the level of sustained release hydrogen peroxide produced upon rehydration of the system is at least 10 mg, preferably 20 mg of hydrogen peroxide per liter or parts per million. Again, the level of sustained release hydrogen peroxide generated will depend on the amount of oxidoreductase enzyme and/or substrate for the oxidoreductase enzyme present in the system. We have advantageously found that after a set time period and subsequent dilution/rehydration the amount of sustained release hydrogen peroxide exceeds that present in natural honey. Furthermore, we have advantageously found that the sustained release of further hydrogen peroxide in the system of the invention occurs for at least a twenty-eight, if not a forty-eight hour period.

Generally, the immunostimulatory effect of the system of the present invention is mediated by interleukin-1. The system of the present invention promotes the release of interleukin-1 (IL-1) from skin cells. IL-1 is a cytokine which is also secreted by macrophages, monocytes and dendritic cells. It is an important part of the inflammatory response of the body against infection. It increases the expression of adhesion factors on endothelial cells to enable transmigration of leukocytes to sites of infection. It also acts on the thermoregulation centre of the brain leading to an increased body temperature in the form of a fever. It is therefore called an endogenous pyrogen. The increased body temperature helps the body's immune system to fight infection. This is the initial phase of an inflammatory immune response which augments the antimicrobial activity of the system. The inflammatory response plays a central role in wound healing through its defence against possible infection and by participating in cell and tissue repair and re-growth. The antimicrobial effect of the system of the present invention is aided and complemented by the immunostimulatory effect which aids the regrowth and repair of damaged tissues and/or cells.

The system of the present invention is based on the unexpected findings of our research which is contrary to the accepted perception in the field. We have established that UMF does not have a role in the antimicrobial/antibacterial activity of Manuka honey and that there is no detectable endogenous hydrogen peroxide in diluted or undiluted Manuka honey. We have found that the glucose oxidase pathway is not operational on initial application of Manuka honey and is only operational to provide an antimicrobial effect following dilution of honey after a period of time has elapsed. Contrary to the common perception in the field, we conclude that Manuka honey antimicrobial efficacy is more than likely mediated through a growth limiting available water content, a marked low initial pH and the production of hydrogen peroxide via the glucose-glucose oxidase pathway only The system of the present invention advantageously utilises these new and unexpected findings and provides a system which gives a regulated, defined and reproducible level of antimicrobial activity and demonstrates a significant difference and increase in activity over the natural honey product. Thus, the system of the present invention overcomes the many disadvantages, in terms of variability, activity, viscosity and additional components which can cause allergic reaction, associated with the natural honey product, Manuka honey.

An additional benefit from the system of the invention is the ability to alter the quantity of active and excipient ingredients thereby permitting the production of a range of formulations of various strengths and properties. This includes the ability to optimise the pH for the required target site.

Furthermore, the system of the present invention allows a high level of quality control with respect to safety and efficacy, batch consistency, potency determination, and a greater control of impurities, in keeping with current Good Manufacturing Practice (cGMP) requirements.

It is a still further advantage of the system of the present invention that it will not cause any allergic reactions, due to its defined composition. Advantageously, this allows for precise labelling instructions as required by the EU legislation for pharmacologically active products.

Ideally, the oxidoreductase enzyme is selected from one or more of the following glucose oxidase, hexose oxidase, cholesterol oxidase, galactose oxidase, pyranose oxidase, choline oxidase, pyruvate oxidase, glycollate oxidase and/or aminoacid oxidase. It will be understood that each oxidoreductase enzyme acts on a specific substrate. The corresponding substrates for these oxidoreductase enzymes are D-glucose, hexose, cholesterol, D-galactose, pyranose, choline, pyruvate, glycollate and/or aminoacid respectively. It will be understood that a mixture of one or more oxidoreductase enzymes and one or more substrates for the oxidoreductase enzymes may be used.

Preferably, the oxidoreductase enzyme is glucose oxidase, hexose oxidase, galactose oxidase and/or pyranose oxidase and the respective substrate for the oxidoreductase enzyme is D-glucose, hexose, D-galactose and/or pyranose.

According to a preferred embodiment of this aspect of the invention, the oxidoreductase enzyme is glucose oxidase and the substrate is D-glucose.

Ideally, water is present in the system at a level from approximately 10% to approximately 20% by weight based on the weight of the total system. More preferably, water may be present a level from approximately 10% to approximately 15% by weight based on the weight of the total system. The amount of water present in the system initially is a crucial aspect of the invention. The addition of excess water can lead to instability in the system, as excess water may give rise to hydrolysis of the glucose oxidase, so it is important that water is only initially present within defined parameters. In addition, the system requires sufficient water to permit generation of $H_2O_2$, ease of application and to prevent precipitation of sugars during storage.

Ideally, the oxidoreductase enzyme is present in the system at an activity of at least 10 U per 100 g of the system. Generally speaking, one unit (U) is that amount of enzyme causing the oxidation of one micromole of glucose per minute at 25° C. and pH 7.0. It will be understood that there must be sufficient oxidoreductase enzyme present to catalyze the substrate and form hydrogen peroxide as needed. Preferably, the oxidoreductase enzyme is present in the system at an activity of at least 100 U, 1400 U or even 5600 U per 100 g of the system.

Ideally, the system as claimed in any of the preceding claims has a pH from approximately 4 to 8, preferably from 5 to 7, more preferably approximately 5.5. The pH is important because it plays a critical role in many therapeutic aspects of the present invention, for example wound healing and also ensures that the oxidoreductase has the correct conditions for needed for optimal activity. For example, Manuka honey has a variable pH around 4. This pH is unsuitable for optimal oxidoreductase enzyme activity and would not be desirable when treating wounds. Thus, the ability to manipulate pH is highly desirable and a significant advantage of the present invention. Advantageously, the pH of the present system may be set at a pH as required for the particular application. Buffering agents may be used to manipulate the pH. Optionally, the system further comprises a buffering agent, preferably carbonic acid-bicarbonate and/or phosphoric acid/disodium hydrogen phosphate. Preferably, the buffering agent is pre-dissolved in and replaces part of the water of the system. Different concentrations of buffering agent can be used depending on the desired pH.

Still optionally, the system may comprise additional sugars. By the term "additional sugars" we mean sugars which are not encompassed by the term "substrate for the oxidoreductase enzyme". In this situation, the additional sugars may be present from 5% to 80%, preferably 10 to 70%, by weight based on the weight of the total system.

Ideally, the additional sugars are present in combination with the substrate for the oxidoreductase enzyme at a ratio of additional sugar to substrate of approximately 10:1 to 0.01:1 preferably from 3.5:1 to 0.05:1. The preferred upper ratio of 3.5:1 is based on minimum substrate for the oxidoreductase enzyme content of 20%, minimum water content of 10% and a maximum additional sugar content of 70%. The preferred lower ratio of 0.05:1 is based on a maximum substrate for the oxidoreductase enzyme content of 85%, a minimum water content of 10% and additional sugar content of 5%.

Thus, according to a preferred embodiment of the present invention, the substrate for the oxidoreductase enzyme, preferably glucose, is present from 20 to 85 w/w % and the additional sugars, preferably sucrose, fructose and/or maltose, are present from 5 to 70 w/w %. At least 10 w/w % of water is present.

In another preferred embodiment of this aspect of the invention, the additional sugars may be selected from one or more of the following sucrose, fructose and/or maltose. Ideally, the substrate for the oxidoreductase enzyme, preferably glucose or any other suitable substrate, and the additional sugars are present in the system in the follow ranges (based on the weight of the total system):

| Substrate for oxidoreductase enzyme | Range (w/w %) |
| --- | --- |
| Glucose | 10 to 85 |
| Additional Sugars | |
| Fructose | 8 to 50 |
| Maltose | 4 to 15 |
| Sucrose | 0.5 to 3 |

Ideally, the ratio of fructose:substrate for the oxidoreductase enzyme:maltose:sucrose is from approximately 1.5:4:2:1 to approximately 3.5:4:1:0.1. A preferred ratio is approximately 4.5:4:1:1.7.

According to another embodiment of this aspect of the invention, the system may further comprise at least one viscosity modifying ingredient. Ideally, the viscosity modifying ingredient is selected from the following:
Methyl cellulose
Carboxymethyl cellulose
Hydroxypropyl methyl cellulose
Hydroxyethyl cellulose
Hydroxypropyl cellulose
Carbopol
Polyvinyl alcohol
Polyvinyl pyrrolidone
Hydrogenated vegetable oils
Xanthan Gum and other natural gums
Polytheylene Glycols (low and high molecular weight)
Paraffin (liquid, semisolid and solid) and/or
Glycerol.
Other conventional viscosity modifying ingredients may also be used.

Optionally, the viscosity modifying ingredient may be the additional sugars as defined before. For example, a change in ratios of the additional sugars may result is a corresponding increase or decrease in the viscosity of the system.

It will be understood that the additional sugars and/or the viscosity modifying ingredients are added to provide the necessary physical properties needed for the specific application of the system. For example, if the system is used topically, it must have sufficient viscosity to adhere to the applied surface. In this situation it may be desirable to use a viscosity modifying ingredient and/or modify the ratios of additional sugars present. In another situation it may be advantageous to modify the viscosity such that the system may be an effective intramammary preparation.

According to a preferred embodiment of this aspect of the present invention, there is provided a storage-stable antimicrobial and immunostimulatory system comprising glucose oxidase, D-glucose and hydrogen peroxide in an aqueous solution;
  wherein D-glucose is present up to 90%, preferably 85%, by weight and water is present up to 20% by weight based on the weight of the total composition; the system has a pH from approximately 4 to 8; and the system provides a two-stage hydrogen peroxide release in which
    (a) storage-stable endogenously produced hydrogen peroxide is bioavailable within the system at a level of at least 10 mg per liter for immediate release; and
    (b) the sustained release of further hydrogen peroxide for at least a twenty-four hour period occurs upon rehydration of the system.

According to another embodiment of this aspect of the invention, there is provided a storage-stable single component antimicrobial and immunostimulatory system comprising
  a. a saturated solution of sugars, including glucose, and water at a ratio of from approximately 10:1 to approximately 5:1, wherein water is present up to 20% by weight based on the total composition;
  b. from approximately 0.01% to 1% by weight of glucose oxidase; and
  c. endogenously derived hydrogen peroxide for immediate release;
wherein the composition has a pH of from approximately 4 to 8, the bioavailability of hydrogen peroxide is maintained in the system and sustained release of further hydrogen peroxide occurs upon rehydration.

The system of the present invention may be in many different physical forms, including but not limited to liquid preparations, solid or semi-solid preparations. In order to prepare solid or semi-solid formulations, the ingredients of the system should be manipulated to lower the water content and increase the content of the other components.

The system of the present invention may be in the form of a liquid preparation. Liquid preparations include but are not limited to a syrup, paste, spray, drop, ointments, creams, lotions, oils, liniments and/or gels. A typical gel includes an alcoholic gel such as isopropanol, ethanol, or propanol and/or a hydrogel.

Alternatively, the system of the present invention may be in the form of a solid or semi-solid preparation. Solid or semi-solid preparations include but are not limited to capsules, pellets, gel caps, hydrogels, pills, pillules and/or globules. Other means used for conventional drug-delivery can be adopted, for example, liposomal delivery may be contemplated.

According to a preferred embodiment of this aspect of the invention, there is provided a pharmaceutical composition comprising the system of the invention together with at least one pharmaceutically acceptable excipient or adjuvant.

According to another embodiment, there is provided a dressing comprising the system or pharmaceutical composition of the invention. Such dressings include gauzes, bandages, films, gels, foams—Lyofoam®, hydrocolloids—Granuflex®, alginates—Kaltostat® (Comvita), hydrogels—Intrasite Gel® and polysaccharide pastes, granules and beads.

According to a particular embodiment, the system may be present together with a wound-dressing matrix. Ideally, the ratio of the system to wound-dressing matrix may be approximately 1:1, although other ratios are contemplated. The wound-dressing matrix may be a collagen or collagen-GAG (glycosaminoglycan) matrix.

It will be understood that the system or pharmaceutical composition of the invention, may be present in many different administration forms. These forms include but are not limited to forms adapted for topical, enteral or parenteral administration.

Forms suitable for topical administration include a topical ointment, cream, lotion, oil, liniment, liquid and/or gel. For example, the system of the present invention may be applied epicutaneously, intranasally, via eye and/or ear drops. One particular embodiment of this aspect of the invention provides the system or pharmaceutical composition of the invention in a form adapted for intramammary administration. In this situation, the system or pharmaceutical composition of the invention may be adapted for delivery as part of a teat seal or intramammary depot delivered via the teat canal. Further compositions may be adapted as tissues, bandages or dressings. This is particularly advantageous for the treatment of infections such as mastitis and has both medical and veterinary applications.

Another form suitable for topical administration includes the system or pharmaceutical composition of the invention wherein the system or composition is in a form adapted for delivery via a dissolvable film strip or strips. In this situation the system of the present invention is soluble upon application.

Enteral administration includes, but is not limited to oral administration. Other enteral administration forms include suppositories and enemas. Forms suitable for oral administration include a capsule, pellet, gel cap, pill, pillule, globule, lozenge, dental floss, toothpaste, mouthwash, dissolvable film strips and/or adapted for delivery as part of a mouth guard. According to one embodiment of this aspect, the system or pharmaceutical composition is in a form suitable for controlled or sustained-release delivery. For example, the oral administration form may have an enteric coating to provide for controlled or sustained-release delivery. This sustained release aspect is important for the treatment of *Campylobacter* infections in poultry and the treatment of *Cryptosporidium* infections in cattle.

Parenteral administration forms include, but are not limited to injection. For example, the system may be adapted for injection by intramammary administration. This is particularly useful for the treatment of mastitis. Intramammary injection by this means involves injection directly into the teat canal using a tube or syringe with a nozzle of appropriate size, e.g. approx. 1.0 mm. Injection in this situation is directed into a body cavity or abscess.

According to another aspect of the present invention, the system may be present in the form of and for use as a cosmetic composition together. Ideally, the system of the present invention is present with at least one suitable cosmetic excipient or adjuvant. Such cosmetic excipients or adjuvants are conventional in this field.

Cosmetic applications cover many different personal care applications. Ideally, for these types of applications, the system may be provided in a form adapted for topical application, although other administration forms previously mentioned may be contemplated.

Such cosmetic applications include, but are not limited to, the treatment of hair conditions or the treatment of body odour. Hair conditions include dandruff and the system of the present invention removes the dead skin that accumulates in the scalp. Furthermore, as dandruff may also have a microbial infection aspect, the system of the present invention can also treat any underlying microbial infection. This microbial infection aspect is discussed in more detail below. The system of the present invention may be used as an alternative to the conventional use of hydrogen peroxide for the control of body odour and any associated microbial infection which causes or exacerbates a body odour problem. Additionally, the system may be used in the treatment of skin conditions, for example, acne. This aspect is expanded on below.

Additionally, the system may be provided in the form of a prophylactic hand barrier solution or hand sanitizer solution. Such a hand barrier solution may be provided in the form of a cream, lotion, hydrogel etc and is used as a hand wash type product with advantageous properties for the prophylactic prevention of microbial infection.

Another cosmetic application includes the use of the system of the present invention in a method for whitening teeth. Conventional teeth whitening involves applying a solution of hydrogen peroxide or bleach to the outside surfaces of the teeth usually under the supervision of a dentist. As the peroxide penetrates the teeth they become lighter in colour. Advantageously, the system of the present invention is provided in a form adapted for oral delivery via a dissolvable film strip or strips, dental floss, toothpaste, mouthwash and/or adapted for delivery via a mouth guard. Delivery by these means facilitates the lightening of the colour of teeth whereby hydrogen peroxide is released from the system of the present invention. The system of the present invention provides a sustained release of hydrogen peroxide which is ideal for whitening teeth. Furthermore, the system is hydrated and easily tolerated, thereby overcoming the disadvantages associated with conventional whitening systems which employ hydrogen peroxide per se.

Thus, the system of the present invention may be used as an alternative hydrogen peroxide source to replace the use of bleach used in many personal care applications.

According to a second aspect of the invention, there is provided the system or pharmaceutical composition of the invention for use in a method of therapy.

According to one embodiment of the present invention, there is provided the system or pharmaceutical composition of the invention for use in a method of treatment of a microbial infection. Furthermore, the system or pharmaceutical composition of the invention may also be used in the prophylactic prevention of such microbial infections.

Additionally and according to another embodiment of the present invention, there is provided the system or pharmaceutical composition of the invention for the regrowth and/or repair of tissues and/or cells, including damaged tissues and/or cells. It will be understood that the system or pharmaceutical composition of the invention enhances an immune response by ideally stimulating the release of interleukin-1 (IL-1). The immunostimulatory properties of the system or pharmaceutical composition of the present invention is responsible for the stimulation, re-growth and repair of damaged tissues and/or cells. It will be understood that the cells include but are not limited to skin cells.

The system or pharmaceutical composition of the present invention provides a dual functionality in that it is both antimicrobial and immunostimulatory. Advantageously, this dual functionality enables the system to be used for a wide range of therapeutic and prophylactic applications.

Ideally, the microbial infection that can be treated using the system of the present invention is any microbial infection that can be treated by hydrogen peroxide.

It will be understood that the microbial infection may caused by gram positive bacteria, gram negative bacteria, acid-fast bacteria, viruses, yeasts, parasitic or pathogenic micro-organisms and/or fungi. Acid-fast bacteria include *Mycobacteria*, including *Mycobacterium tuberculosis* which causes TB. Such microbial infections may be caused by, but not limited to, *Escherichia coli, Staphylococcus aureus, Pseudomonas aeruginosa, Candida albicans, Propionibacterium acnes, Staphylococcus aureus, Staphylococcus epidermidis, Staphylococcus saprophyticus*, Beta haemolytic Streptococci Group A, *Campylobacter coli, Campylobacter jejuni*, Methicillin Resistant *Staphylococcus Aureus* (MRSA), *Botrytis cinerea* and/or *Mycobacterium tuberculosis*.

In addition the microbial infection may be caused by *Cryptosporidium*, a protozoan pathogen of the *Phylum Apicomplexa*. *Cryptosporidium* causes a diarrheal illness called cryptosporidiosis. Other apicomplexan pathogens covered by the present application include the malaria parasite *Plasmodium*, and *Toxoplasma*, the causative agent of toxoplasmosis.

Advantageously, the present invention may be used in the treatment or prophylactic prevention of MRSA or other antibiotic resistant micro-organisms and bacteria. Thus, the invention overcomes the problem of emerging antibiotic resistant strains of micro-organisms in a non-toxic manner. Furthermore, we have observed no resistance to our system in contrast to the application of Nisin which generates resistance as shown in the Examples. This is a major advantage of the present invention over and above conventional systems. For this application, the system or pharmaceutical of the present invention may be administered topically, for example as a topical ointment, cream, lotion, oil, liniment, liquid and/or gel. Optionally, the system or pharmaceutical of the present invention may be administered as part of a tissue or skin wipe. This type of administration may be important in the prophylactic prevention of MRSA and MRSA-type infections.

The microbial infection may be an oral, eye and/or ear infection. The oral infection may be gum disease, oral ulceration and/or an oral hygiene disorder. The oral hygiene disorder may be halitosis and/or gingivitis. Alternatively, the oral infection may be a throat infection or a nasal infection, including nasal Staphylococci infections. An eye infection may include conjunctivitis.

Another condition is mastitis, including wet and/or dry mastitis. Mastitis is a major condition in both humans and animals and is initially caused by microbial infection through damaged skin, blockage of the teat canal, or contact with infected surfaces. In particular, mastitis has a tremendous economic importance for the dairy industry as the present antibiotic therapies require that milk must be withheld from the food chain for a period of up to 4 days following completion of therapy. This leads to a major reduction in milk yield. Thus, alternative therapies to conventional antibiotic therapies are under evaluation. Common causal microorganisms found in mastitis include:
*Staphylococcus aureus*
*Staphylococcus albus*
*Streptococcus* species
*Escherichia coli*
*Salmonella* species
*Mycobacterium tuberculosis*
Fungal mastitis—*Candida albicans* and *Cryptococcus neoformans*

We have advantageously, that the system or pharmaceutical composition of the present invention can be used in the treatment of mastitis. Such a treatment does not involve the use of antibiotics. As such, is of significant importance to the dairy industry. As expanded on previously, the system or pharmaceutical composition of the invention may be in a form adapted for intramammary administration, for example in a form adapted for delivery as part of a teat seal, tissue, skin wipe, bandage or dressing or in a form suitable for intramammary injection.

Additionally, the microbial infection may be a skin and/or nail infection.

Alternatively, the system or pharmaceutical composition of the present invention may be used in the treatment of fungal skin and/or fungal nail infections. Fungal skin infections include athlete's foot and/or ringworm in humans. In veterinary medicine, fungal skin conditions include foot rot, ringworm and the control of zoonotic skin infections. Fungal nail infections include onychomycosis.

Additionally, the system or pharmaceutical composition of the present invention may be used in the treatment of a skin disorder. The skin disorder may be acne, eczema and/or psoriasis. Advantageously, we have found that the system of the present invention is as efficacious as conventional antiacne therapies. It will be understood that acne and eczema may also have a microbial infection component which the system treats. Furthermore, secondary microbial infections of psoriatic lesions caused by scratching can be treated by the system of the present invention. The immunostimulatory effect of the system of the present invention can also aid the re-growth and repair of the damaged tissue or skin cells.

According to another embodiment of the present invention, the system or pharmaceutical composition may be used in a method of wound care, including the treatment of a wound and/or the treatment or management of wound sepsis. The wound may be an acute wound, chronic wound, surgical wound, chronic burn and/or acute burn. This aspect of the invention involves both the treatment of a microbial infection and the re-growth/repair of damaged tissues and cells, preferably skin cells. One particular embodiment of this aspect involves the use of the system or pharmaceutical composition of the present invention in a method of stoma management. The stoma may have resulted from a colostomy, ileostomy, jejunostomy and/or gastrostomy. Another embodiment involves the treatment of diabetic ulcers or wounds.

Alternatively, the system or pharmaceutical composition of the present invention may be used in the prophylactic prevention of wound sepsis.

It will be understood that the system of the present invention may be used in both veterinary medicine and human applications.

Many of these specific human applications have been defined previously. However, as defined above the system or pharmaceutical composition of the present invention may be used in the treatment of general microbial infections and the treatment or management of skin disorders, wound care and/or burn treatment. The treatment or management of wounds and burns can involve both the antimicrobial and immunostimulatory effect of the system of the present invention.

Important veterinary applications also involve the treatment of microbial infections and the treatment or management of wound care and/or burn treatment. However, specific conditions include wet and dry mastitis in cattle or other domestic animals, chronic skin infections in dogs (subcutaneous *Staphylococcus* infections), Otitis externa (ear infections), oral care in animals, *Campylobacter* infections in chickens, coliosis, enteric microbial infections in pigs, poultry and cattle, *Cryptosporidium* infections, clearance of zoonotic infections, wound dressing, e.g. horn removal, and abscess treatment. The present invention has particular advantages in veterinary usage, in that it allows the treatment of microbial infections without introducing antibiotics into the food chain.

According to a third aspect of the present invention, there is provided the use of the system or pharmaceutical composition of the present invention for the manufacture of a medicament for treating a microbial infection or for the prophylactic prevention of a microbial infection.

Additionally, there is provided the use of the system or pharmaceutical composition of the present invention for the manufacture of a medicament for the repair and/or re-growth of damaged tissues and/or cells. The system or pharmaceutical composition of the present invention ideally enhances an immune response by stimulating the release of interleukin-1 (IL-1) as defined previously.

The microbial infection may be caused by gram positive bacteria, gram negative bacteria, acid-fast bacteria, viruses, yeasts, parasitic or pathogenic micro-organisms and/or fungi. Acid-fast bacteria includes *Mycobacteria*, including *Mycobacterium tuberculosis* which causes TB. Such microbial infections may be caused by, but not limited to *Escherichia coli, Staphylococcus aureus, Pseudomonas aeruginosa, Candida albicans, Propionibacterium acnes, Staphylococcus aureus, Staphylococcus epidermidis, Staphylococcus saprophyticus*, Beta haemolytic Streptococci Group A, *Campylobacter coli, Campylobacter jejuni*, Methicillin Resistant *Staphylococcus Aureus* (MRSA), *Botrytis cinerea, Mycobacterium tuberculosis* and/or *Cryptosporidium* as defined previously.

The term "microbial infection" as used in the present invention has been defined previously. Again, specific examples of these types of infections have been mentioned previously. The microbial infection may be an oral, eye and/or ear infection. The oral infection may be gum disease, oral ulceration and/or an oral hygiene disorder. The oral hygiene disorder may be halitosis and/or gingivitis. Alternatively, the oral infection may be a throat infection or a nasal infection, including nasal Staphylococci infections. An eye infection may include conjunctivitis. Alternatively, the microbial infection may be a skin and/or nail infection. Alternatively, the microbial infection may be a fungal nail and/or skin infection, such as athlete's foot and/or ringworm.

Another preferred embodiment includes the treatment of mastitis, including wet and/or dry mastitis.

Additionally, there is provided the use of the system or pharmaceutical composition of the present invention for the manufacture of a medicament for the treatment of a skin disorder. The skin disorder may be acne, eczema and/or psoriasis which may have a microbial component.

Additionally, there is provided the use of the system or pharmaceutical composition of the present invention for the manufacture of a medicament for treating a wound and/or the treatment or management of wound sepsis. The wound may be an acute wound, chronic wound, surgical wound, chronic burn and/or acute burn. Additionally, there is provided the use of the system or pharmaceutical composition of the present invention for the manufacture of a medicament for stoma management. The stoma may result from a colostomy, ileostomy, jejunostomy and/or gastrostomy.

Additionally, there is provided the use of the system or pharmaceutical composition of the present invention for the manufacture of a medicament for use in the prophylactic prevention of wound sepsis.

It will be understood that the microbial infection, skin disorder, wound or other disorder will be treated by a method which comprises the topical, enteral and/or parenteral administration of the system or pharmaceutical composition of the present invention as defined previously.

According to a fourth aspect of the present invention there is provided a method for treating a microbial infection and/or the repair and/or re-growth of tissues and/or cells of a patient comprising the steps of applying an effective amount of the system or pharmaceutical composition of the present invention to an infected area of the patient by topical, enteral and/or parenteral mode of administration.

Again, the term "microbial infection" as used in the present invention has been defined previously and specific examples of these types of infections have been mentioned previously and are applicable to this aspect of the invention. The method may also involve the treatment of a skin disorder, wound and/or treatment or management of wound sepsis as defined previously.

According to a fifth aspect of the present invention, it will be understood that the system of the present invention may be used for the sterilisation of compositions, including water, or products, such as field surgical devices. Thus, the system of the present invention may be used in water decontamination or device sterilisation in applications such as camping and emergency use.

According to a sixth aspect of the present invention, there is provided a process for manufacture of a storage-stable antimicrobial and immunostimulatory system of the present invention comprising an oxidoreductase enzyme, a substrate for the oxidoreductase enzyme and hydrogen peroxide in an aqueous solution comprising the steps of a. heating the water to a temperature of at least 60° C., preferably from approximately 75° C. to 95° C.;
b. adding the substrate for the oxidoreductase enzyme to the heated water to form a water-sugar solution,
c. cooling the water-sugar solution to a temperature below approximately 40° C. to allow retention of enzyme activity;
d. adding the oxidoreductase enzyme to the water-sugar solution of step (c) with stirring to form hydrogen peroxide at a pre-determined controlled rate; and
e. cooling the resultant mixture from step (d) to room temperature to produce a system with bioavailable and storage-stable endogenously produced hydrogen peroxide at a level of at least 10 mg per liter for immediate release.

Uncontrolled heat treatment of sugars tends to produce carmelisation resulting in a formulation that acquires a yellow to brown colouration. To eliminate carmelisation, and thereby produce a clear material, the manufacturing process above was developed in which the order of addition of sugars and their dissolution by heating is carefully selected to circumvent the carmelisation process.

Preferably, the process comprises the further step of adding of a buffering agent to the system to achieve a pH from approximately 4 to 8, preferably 5 to 7, more preferably 5.5. The buffering agent may be added during or after step (d)

Ideally, the oxidoreductase enzyme is glucose oxidase, hexose oxidase, cholesterol oxidase, galactose oxidase, pyranose oxidase, choline oxidase, pyruvate oxidase, glycollate oxidase and/or aminoacid oxidase and the substrate for the oxidoreductase enzyme is D-glucose, hexose, cholesterol, D-galactose, pyranose, choline, pyruvate, glycollate and/or aminoacid.

According to a preferred embodiment, the oxidoreductase enzyme is glucose oxidase and the substrate for the oxidoreductase enzyme is D-glucose.

Optionally, additional sugars as defined previously may be added to the system in step (b). These additional sugars may comprise one or more of sucrose, fructose and/or maltose.

Ideally, where one or more sugars are added, each sugar is added in a sequentially after the previous sugar has fully dissolved in the water of step (a).

According to one embodiment of this aspect of the invention, the sugars are added in the following sequence: fructose, glucose, maltose and sucrose. Each sugar is dissolved fully in the water by heating to approximately 90° C. before the next sugar is added. Alternatively, the sugars can be prepared as above but under a vacuum at approximately—0.5 Bar. This vacuum reduces the boiling point of the sugars to a temperature of less than 90° C. thereby preventing discoloration.

Optionally, at least one viscosity modifying ingredient may be added to the system during the above process. Ideally the viscosity modifying ingredient is selected from polyethylene glycol, glycerol and/or liquid paraffin. Other conventional viscosity modifying ingredients may be contemplated.

Another particular aspect of the present invention provides a process for manufacture of a single component antimicrobial system according to the invention comprising the steps of
a. heating the water, preferably to approximately 85+/−10° C.;
b. adding glucose, sucrose, fructose, maltose to the heated water, wherein each sugar is added in a pre-defined order, preferably sequentially, only after the previous sugar has fully dissolved in the water of step (a);
c. cooling the water/sugar solution to a temperature which allows retention of enzyme activity, preferably below approximately 40° C.;
d. adding an oxidoreductase enzyme to the solution of step (c) with stirring to form hydrogen peroxide at a pre-determined controlled rate.
e. cooling the resultant mixture to room temperature to produce a viscous solution with bioavailable hydrogen peroxide.

Once the system of the present invention is made according to the above process, the system of the invention may be packaged in an opaque, impermeable container. This prevents the further production of hydrogen peroxide, which can only be reinitiated when in an aerobic atmosphere.

The system generated according to the above process may be a liquid solution, solid or semi-solid preparation. After manufacture, the system may then be processed into the desired end product i.e. administration form, such as solid or semi-solid form suitable for the different forms of administration discussed previously. For example, the system may be combined with an alcoholic gel to provide a gel form suitable for administration. Additionally, the system may be incorporated onto various commercially available dressings.

The system may also be subjected to post-manufacturing sterilisation, by for example, irradiation. Such post-manufacture sterilisation has no negative effect on the system of the present invention.

The invention will now be illustrated by the following non-limiting examples with reference to the following figures, in which:

FIG. 1a shows a microbial inhibition profile of Manuka honey on *Staphylococcus aureus*. Manuka honey demonstrates a two tier inhibition profile. The first tier of microbial inhibition activity occurs between dilutions 50% to approximately 6.25% and the second tier of microbial inhibition activity occurs at dilutions 3.125% to approximately 0.195%;

FIG. 1b shows a microbial inhibition profile of pH adjusted Manuka honey on *Staphylococcus aureus*. Adjusting the pH of Manuka honey from its natural pH of approximately 4.0 to a pH of 6.8 does not affect the microbial inhibition profile;

FIG. 1c shows a microbial inhibition profile of pH adjusted Manuka honey to which an excess of catalase has been added on *Staphylococcus aureus*. Manuka honey pH adjusted to near a neutral pH followed by the addition of catalase in excess alters the microbial inhibition profile of the honey. The first tier of microbial inhibition is only slighted affected but the second tier is significantly affected indicating that the antibacterial effect in the second tier is primarily the result of hydrogen peroxide liberation;

FIG. 2 shows a microbial inhibition profile of Manuka honey and a prototype formulation on *Staphylococcus aureus*. The prototype formulation demonstrates greater activity compared to that of the Manuka honey;

FIG. 3a shows the results of a microbial inhibition assay using gel based prototype formulations on *Staphylococcus aureus, E. coli* and *Candida Albicans*. Both cellulose based gels demonstrate a decrease in stability and neither cellulose based gel formulation is as active as the prototype formulation as evidenced by the smaller zones of inhibition in diffusion assays (compare FIG. 3a (gels) with FIG. 3b (prototype formulation));

FIG. 3b shows the results of a microbial inhibition assay of the prototype formulations on *Staphylococcus aureus*. Large zones of inhibition are evident indicating activity;

FIG. 4a shows the results of microbial inhibition assay of Glucose//glucose oxidase only formulations on different bacteria. Microbial inhibition assays of 4 replicate of 75% D-glucose with 0.5% GOX 5600 U/g in wells and their antimicrobial activity against a number of different bacteria. These formulations demonstrate a limited degree of antibacterial activity. This activity is below that observed with the prototype antimicrobial formulation described in Example 2 as evidenced by the smaller zones of inhibition in Well/Disc diffusion assays (compare FIG. 4a (gels) with FIG. 4b (prototype));

FIG. 4b shows the results of microbial inhibition assay of the prototype formulation against a number of different bacteria;

FIG. 5a shows the activity of $A^3IS$ containing different GOX (5600 U/g) enzyme concentrations against *S. aureus*. Varying the glucose oxidase content in $A^3IS$ and its affect on the inhibition profile was measured. The antibacterial activity of $A^3IS$ increases proportionally to the concentration of glucose oxidase. A substantial antibacterial effect is attained at an enzyme concentration of 0.05%;

FIG. 5*b* shows $H_2O_2$ generation over time by $A^3IS$ containing 0.5% sigma Aldrich GOX enzyme 5600 U/g diluted 50% (C1), 25% (C2), 12.5% (C3) or 6.25% in de-ionised water (DI). $A^3IS$ generates significantly increased levels of hydrogen peroxide compared to Manuka honey diluted at 50% in DI water;

FIG. 5*c* shows $H_2O_2$ generation over time by $A^3IS$. Production of $H_2O_2$ by $A^3IS$ with 0.5% sigma Aldrich GOX enzyme 5600 U/g and diluted 25% in DI water) is maintained for a period of at least 48 h;

FIG. 5*d* shows that $A^3IS$—antimicrobial activity increases with increased glucose oxidase concentration. Potency/efficacy is dependant on the concentration of glucose oxidase in $A^3IS$ formulations. Results show an increase in efficacy with increasing glucose oxidase concentration when tested on *Staphylococcus aureus, Pseudomonas aeruginosa* and *Escherichia coli*;

FIG. 6 shows the stability results and retention of $H_2O_2$ reservoir by $A^3IS$ over a ten month period. The available $H_2O_2$ reservoir produced by $A^3IS$ is storage stable. The level of available $H_2O_2$ present was initially determined immediately after being placed into tubes and again after a period of 7 and 10 months had elapsed. There is no evidence of a loss of available $H_2O_2$ within the $A^3IS$ formulation, thus, indicating stability. Similar results have been obtained with several other batches.

FIG. 7*a* shows antimicrobial activity in an $A^3IS$ formulation on *Staphylococcus aureus* over 3 months. The antimicrobial activity in an $A^3IS$ formulation on *Staphylococcus aureus* demonstrates a consistent level of antimicrobial activity over time as determined by zones of inhibition measured at each sampling time point and the results graphed using 95% confidence limits during a period of 3 months;

FIG. 7*b* shows the antimicrobial activity in an $A^3IS$ formulation on *Staphylococcus aureus* over 14 months. The antimicrobial activity in an $A^3IS$ formulation on *Staphylococcus aureus* demonstrates a consistent level of antimicrobial activity over time as determined by zones of inhibition measured at each sampling time point and the results graphed using 95% confidence limits during a period of 14 months;

FIG. 8*a* shows the $A^3IS$ antimicrobial activity against *Staphylococcus aureus*, NCCLS kill curve method. Antimicrobial activity of $A^3IS$ against *Staphylococcus aureus*, as determined by an NCCLS kill curve method. $A^3IS$ has increased efficacy compared with Manuka honey and comparable efficacy to silver dressing;

FIG. 8*b* shows the $A^3IS$ antimicrobial activity against *Staphylococcus aureus*, a Medical Device Manufacturer's Specific Method. Antimicrobial activity of $A^3IS$ against *Staphylococcus aureus*, as determined by a Medical device manufacturer's specific protocol. $A^3IS$ has increased efficacy compared with Manuka honey and comparable efficacy to silver dressing;

FIG. 8*c* shows the $A^3IS$—antimicrobial activity against beta haemolytic Streptococci Group A. Results of an inhibition assay (3 day repeats) for $A^3IS$, Medihoney® and a 10% phenol gel tested against 5 clinical isolates of the Beta haemolytic Streptococci Group A. $A^3IS$ is at normal pH 5.5 (test material A) and pH 7 (test material B), a negative control of $A^3IS$ containing no GOX is included. Formulation $A^3IS$ demonstrates comparable in vitro efficacy to a 10% phenol gel and is superior to Medihoney®;

FIG. 8*d* shows the $A^3IS$—antimicrobial activity against *Campylobacter*. Results of an inhibition assay (3 day repeats) for $A^3IS$, Manuka honey and a 10% phenol gel when tested against 5 clinical isolates of *Campylobacter* spp. Formulation $A^3IS$ is at normal pH 5.5 (test material A) and pH 7 (test material B), a negative control $A^3IS$ containing no GOX is included. Results indicate significant anti-*Campylobacter* in-vitro efficacy and the superiority of $A^3IS$ over Manuka honey;

FIG. 9*a* shows the $A^3IS$—antimicrobial activity against *P. acnes*. $A^3IS$ activity against *P. acnes* under varying incubation conditions: light and dark aerobic, light and dark anaerobic. $A^3IS$ demonstrates a high level of activity against *P. acnes*, indicating the materials potential for topical acne application;

FIG. 9*b* shows the $A^3IS$—antimicrobial activity against *P. acnes*. Antimicrobial activity of $A^3IS$ and currently available anti-acne commercial products including some commercial products which incorporate antibiotics are shown. $A^3IS$ demonstrates a high level of comparable activity to commercially available anti acne products indicating the materials potential for topical acne application;

FIG. 10 shows the $A^3IS$ antimicrobial activity against 8 strains of MRSA on three different days and compared to a 10% phenol standard and to Manuka honey. Formulation $A^3IS$ is at normal pH 5.5 (test material A) and pH 7 (test material B), a negative control $A^3IS$ containing no GOX is included. The results demonstrate significant in vitro anti-MRSA efficacy and the superiority of $A^3IS$ over Manuka honey and a 10% phenol gel control;

FIG. 11*a* shows $A^3IS$ antimicrobial activity against MRSA compared to a 10% phenol standard and to Manuka honey. Formulation $A^3IS$ is at normal pH 5.5 (test material A) and pH 7 (test material B), a negative control $A^3IS$ containing no GOX is included. The results demonstrate significant in vitro anti-MRSA efficacy and the superiority of $A^3IS$ over Manuka honey and a 10% phenol gel control;

FIG. 11*b* shows the $A^3IS$ antimicrobial activity against clinical isolates of Mastitis compared to Antibiotics. $A^3IS$ inhibition assay (3 day repeats) compared to four antibiotics (Vancomycin, Streptomycin, Tetracycline and Chloramphenicol) when tested against 22 clinical isolates of Mastitis causing *Staphylococcus aureus* organisms. $A^3IS$ demonstrates superior in vitro efficacy to all of these antibiotics. Clinical isolate number 15 is resistant to Vancomycin, Streptomycin and Tetracycline and shows only mild sensitivity to Chloramphenicol, however, it demonstrates sensitivity to $A^3IS$;

FIG. 11*c* shows the $A^3IS$ antimicrobial activity against clinical isolates of Mastitis compared to commercially available anti Mastitis products. $A^3IS$ inhibition assay (3 day repeats) compared to four of the leading commercially available anti mastitis multi antibiotic products when tested against 22 clinical isolates of Mastitis causing *Staphylococcus aureus* organisms. Formulation $A^3IS$ demonstrates comparable in vitro efficacy compared to three of the leading commercial products and is superior to one of these products;

FIG. 11*d* shows the $A^3IS$ antimicrobial activity against clinical isolates of Mastitis compared to a 2% Nisin Solution. $A^3IS$ inhibition assay (3 day repeats) compared to a 2% Nisin solution on 21 clinical isolates of Mastitis causing *Staphylococcus aureus* organisms. Formulation $A^3IS$ demonstrates superior in vitro efficacy to the 2% Nisin solution. Note: Clinical isolate number 15 of FIG. 11*b* was unrecoverable from storage and is not included in this assay;

FIG. 11*e* shows the development of Nisin Resistance. A 2% Nisin resistant colony (indicated by the arrow) within the zone of inhibition during a Nisin efficacy study. $A^3IS$ resistant colonies have never been observed;

FIG. 12a shows A³IS MTT toxicity assessment on NHFs (Normal Human Fibroblasts. Included in the assay are a 50% concentration of A³IS, a range of concentrations of commercial silver containing gel and a commercial zinc containing gel product, compared to sodium azide (positive control). A³IS demonstrates less toxicity than either the commercial silver containing gel or the commercial zinc containing gel product;

FIG. 12b shows A³IS MTT toxicity assessment on NHKs (Normal Human Keratinocytes). Included in the assay are a 50% concentration of A³IS, a range of concentrations of a commercial silver containing gel and a commercial zinc containing gel product, compared to sodium azide (positive control). A³IS demonstrates less toxicity than either the commercial silver containing gel or the commercial zinc containing gel product;

FIG. 12c shows A³IS agar overlay cytotoxicity assessment on L929 cells. Included in the assay are a 50% concentration of A³IS, a range of concentrations of a commercial silver containing gel and a commercial zinc containing gel product, compared to sodium azide (positive control). A³IS demonstrates less toxicity than either the commercial silver containing gel or the commercial zinc containing gel product;

Figure 13A:
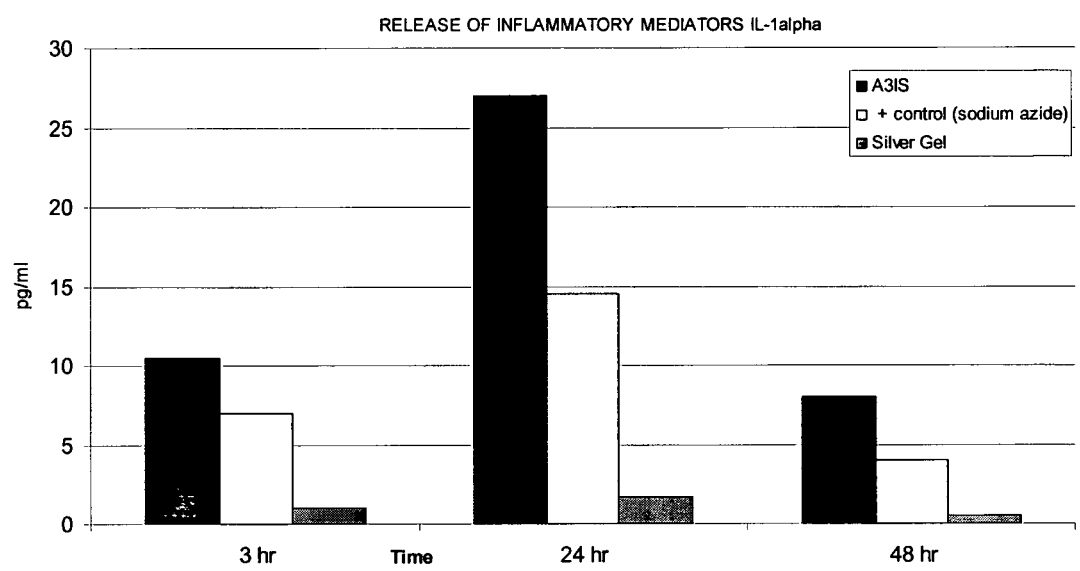
Figure 13B:
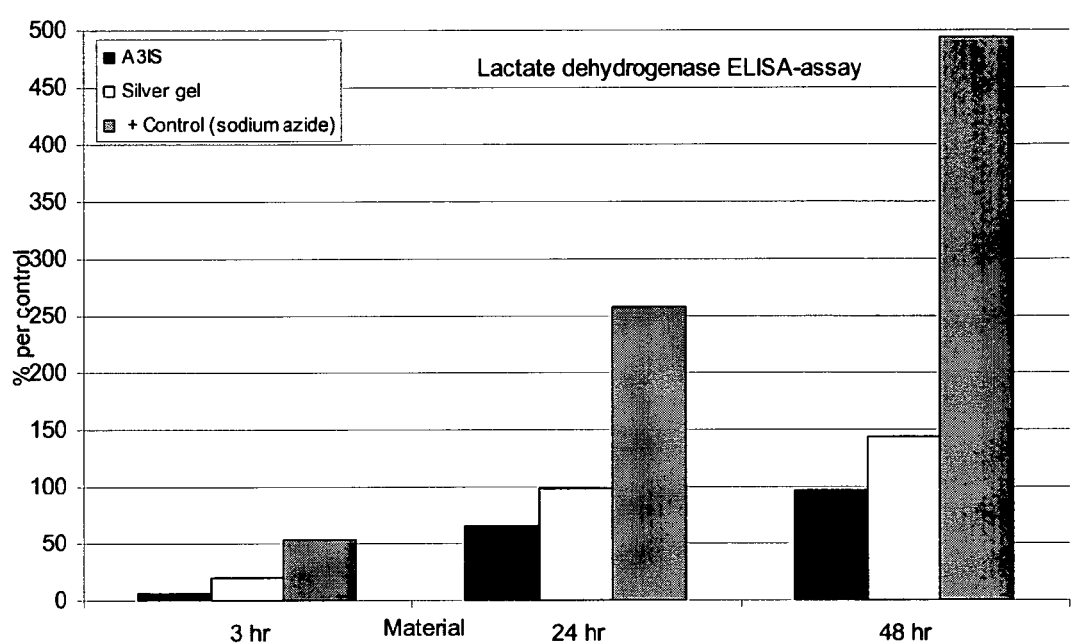
Figure 14:
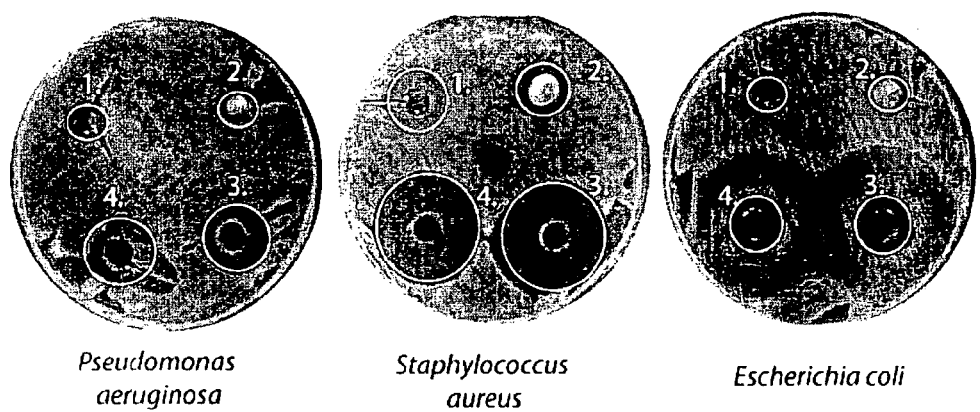
Figure 14:
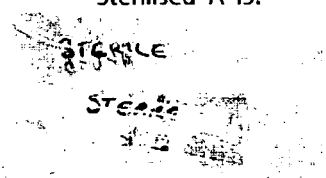
Figure 14:
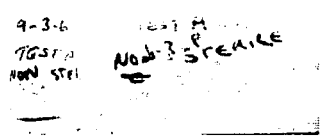
Figure 15A:
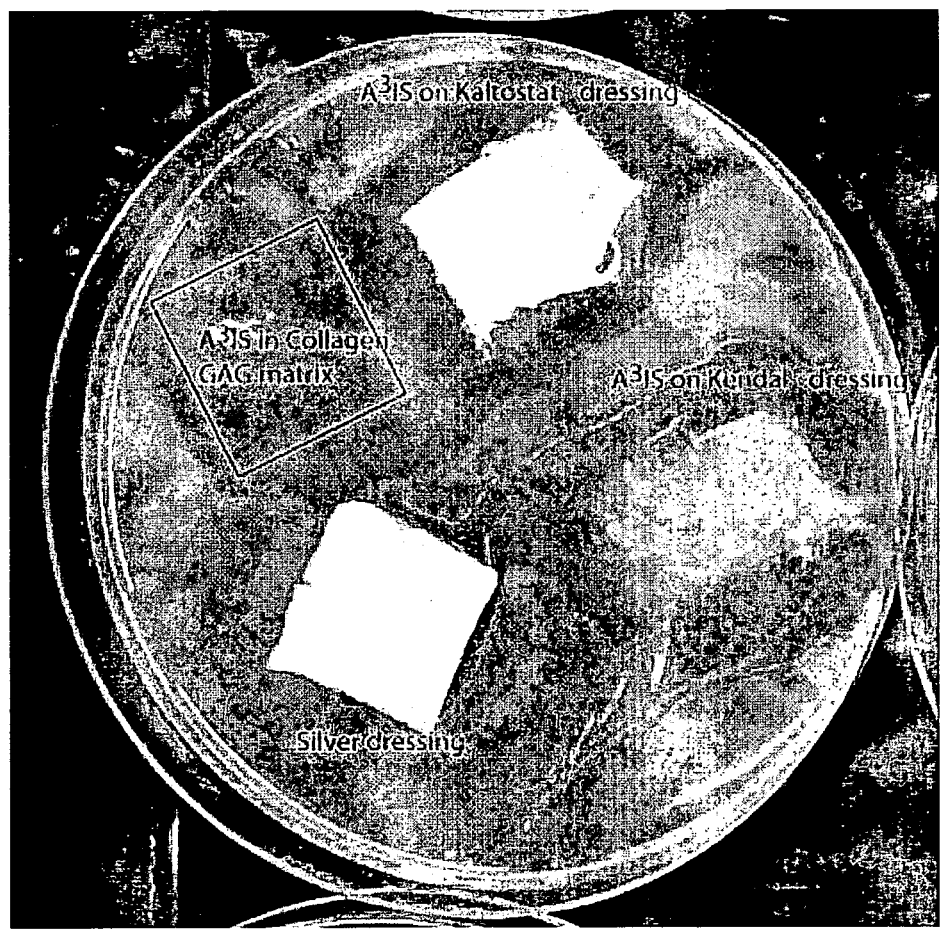
Figure 15B:
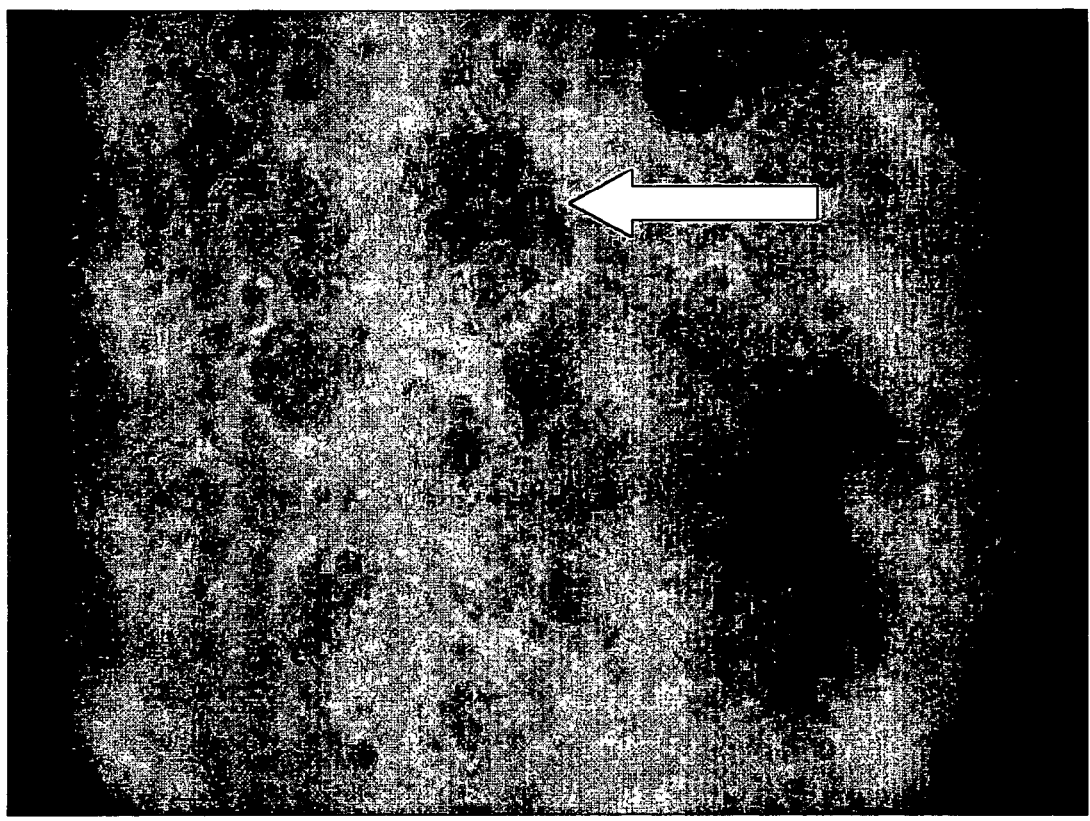
Figure 15C:
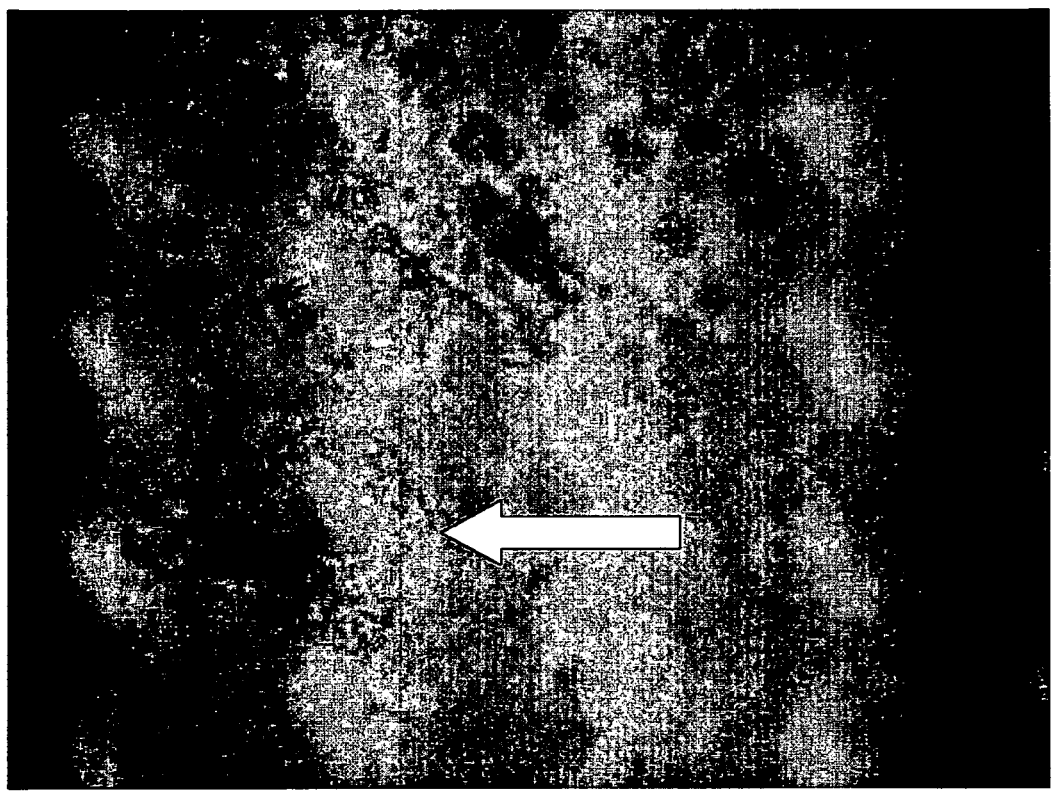

FIG. 13a shows induction of IL-1 release by A³IS. ELISA assay of the supernatant from a 3D irritancy assay over a 48 hour period, measuring and comparing the release of IL-1 when exposed to A³IS formulation, to a sodium azide positive control, and a commercial silver containing gel product. The results indicate that IL-1 is released from the skin cells exposed to the A³IS formulation;

FIG. 13b shows the induction of LDH release by A³IS. ELISA assay of the supernatant from a 3D irritancy assay over a 48 hour period, measuring and comparing the release of Lactate Dehydrogenase (LDH) when exposed to A³IS, a sodium azide positive control, and a commercially available silver containing gel product. Lactate dehydrogenase is released by cells exposed to destructive compounds. The results indicate that the A³IS formulation is less toxic than commercially available silver containing gel products;

FIG. 14 shows A³IS before and after sterilisation by Gamma irradiation. Gamma irradiation does not reduce activity as shown by zone of inhibition assays on S. aureus, E. coli and Pseudomonas aeruginosa;

FIG. 15a shows A³IS in a Collagen-GAG matrix and in commercial wound dressings tested for antibacterial activity against S. aureus. A³IS demonstrates antibacterial activity which is superior to that observed with a commercially available silver dressing used as a control;

FIGS. 15b and 15c show collagen-GAG matrix infiltration by NHFs. Infiltration by NHFs of the Collagen-GAG matrices. Over a 4 day period following addition of test sections NHFs are observed to attach to and grow within and along the Collagen-GAG matrices as indicated by the arrow.

Figure 16A:
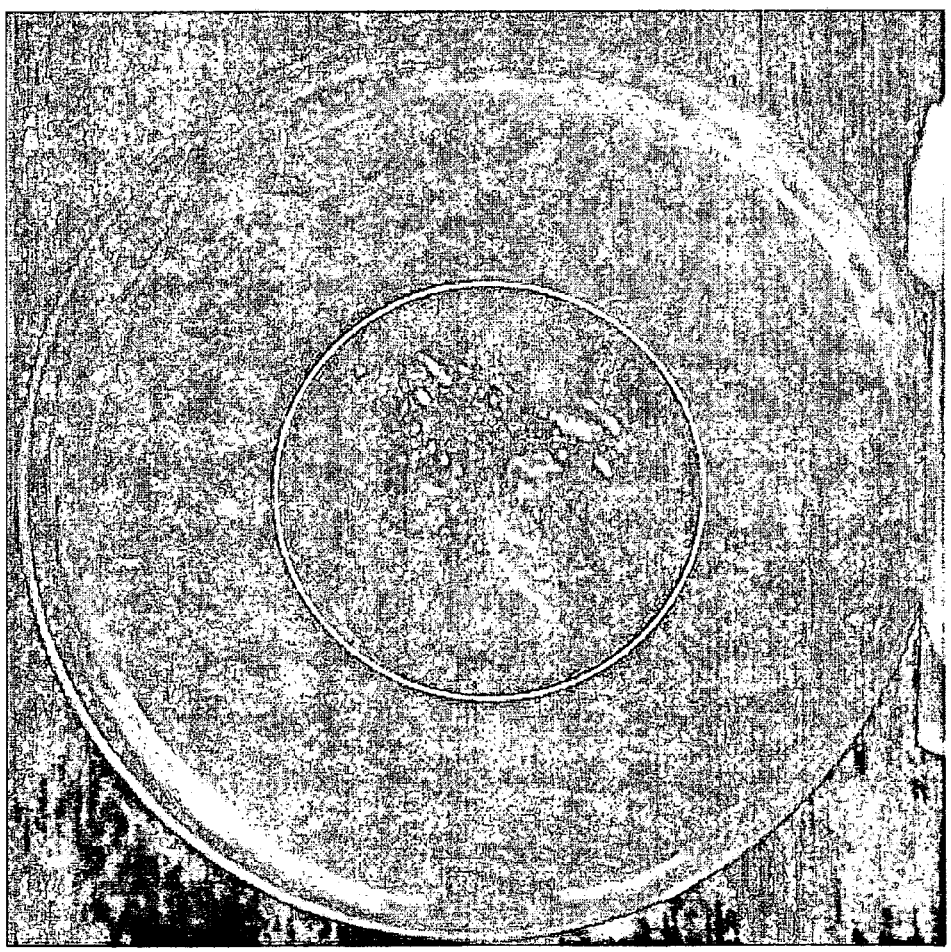
Figure 16B:
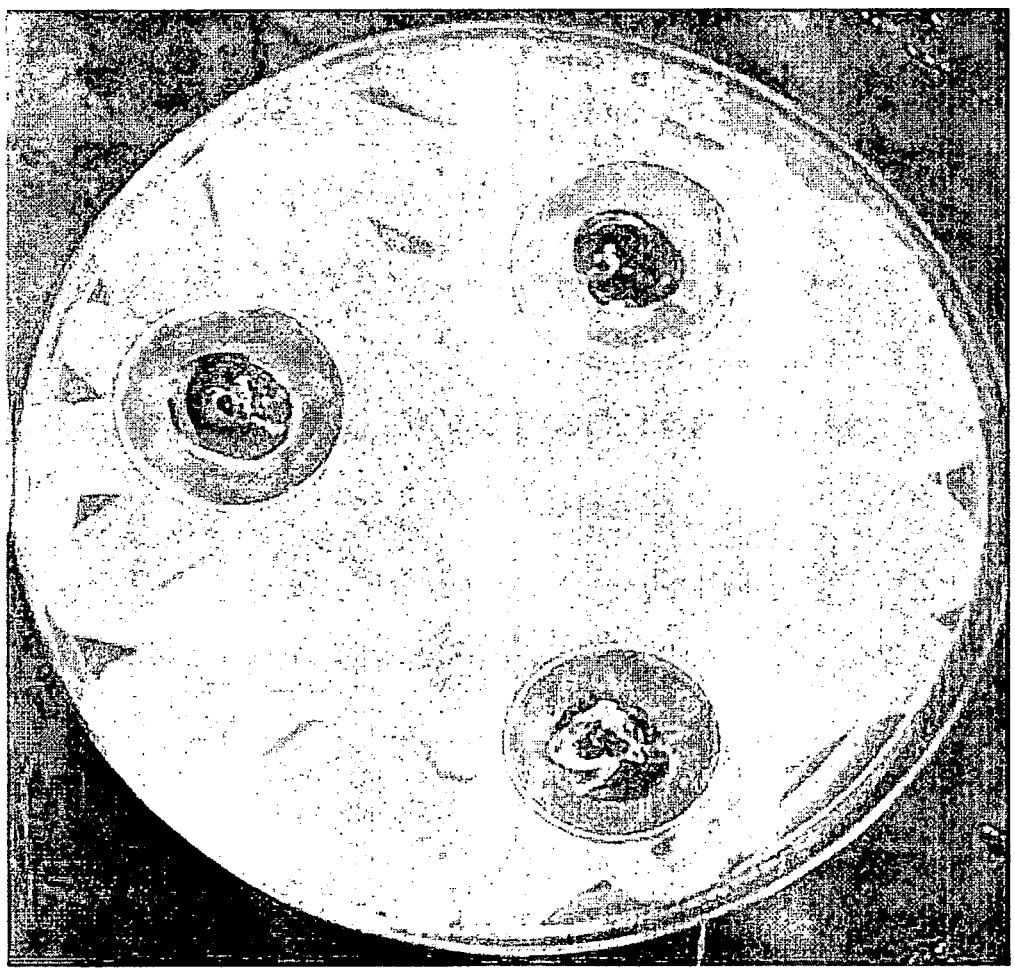
Figure 17:
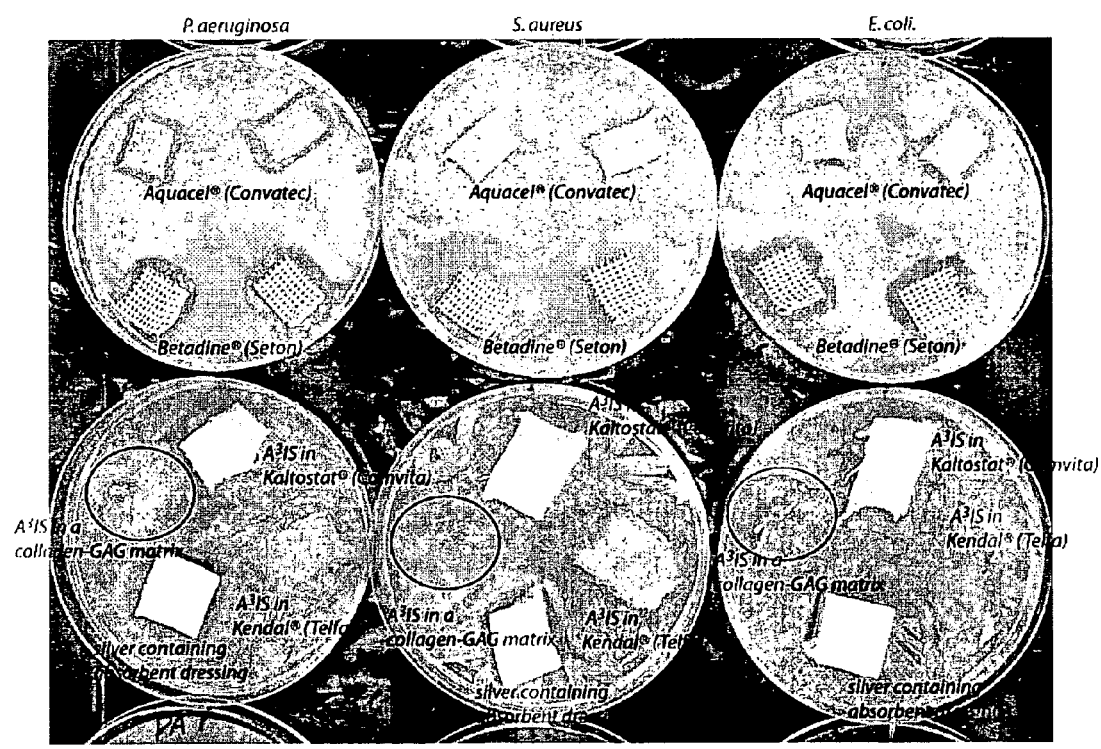
Figure 18A:
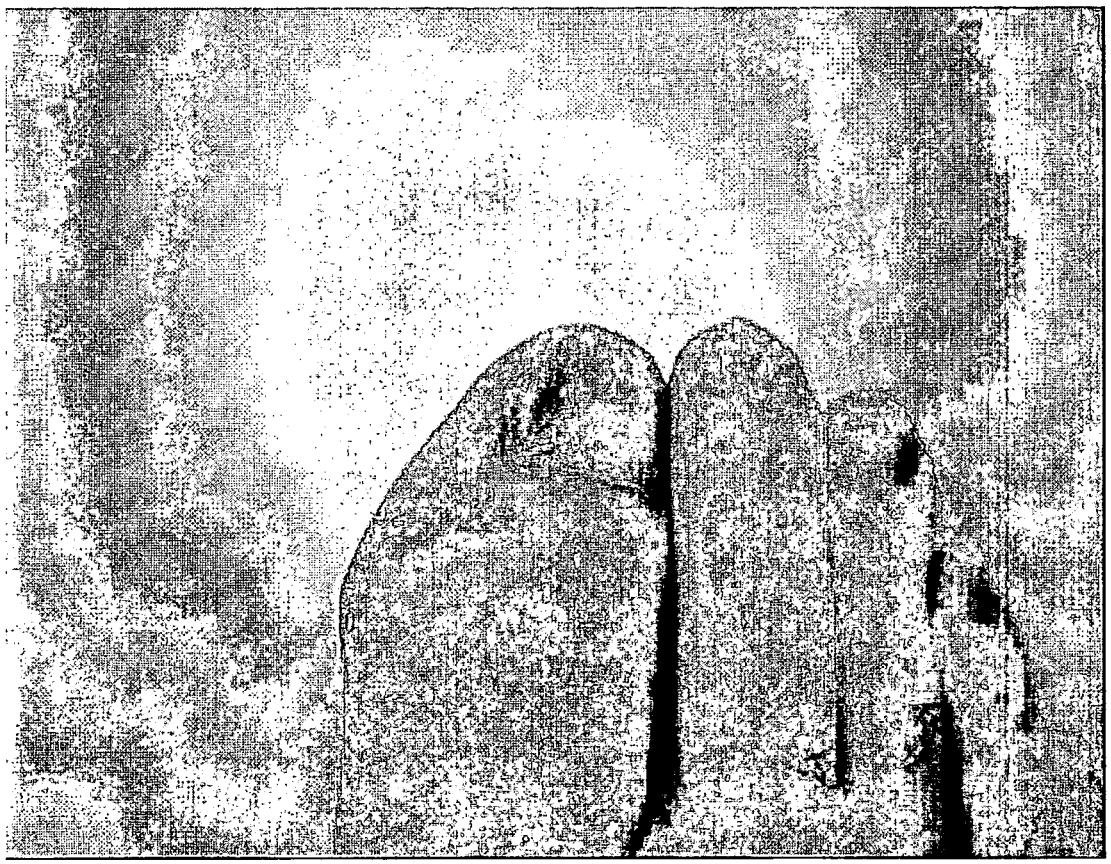
Figure 18B:
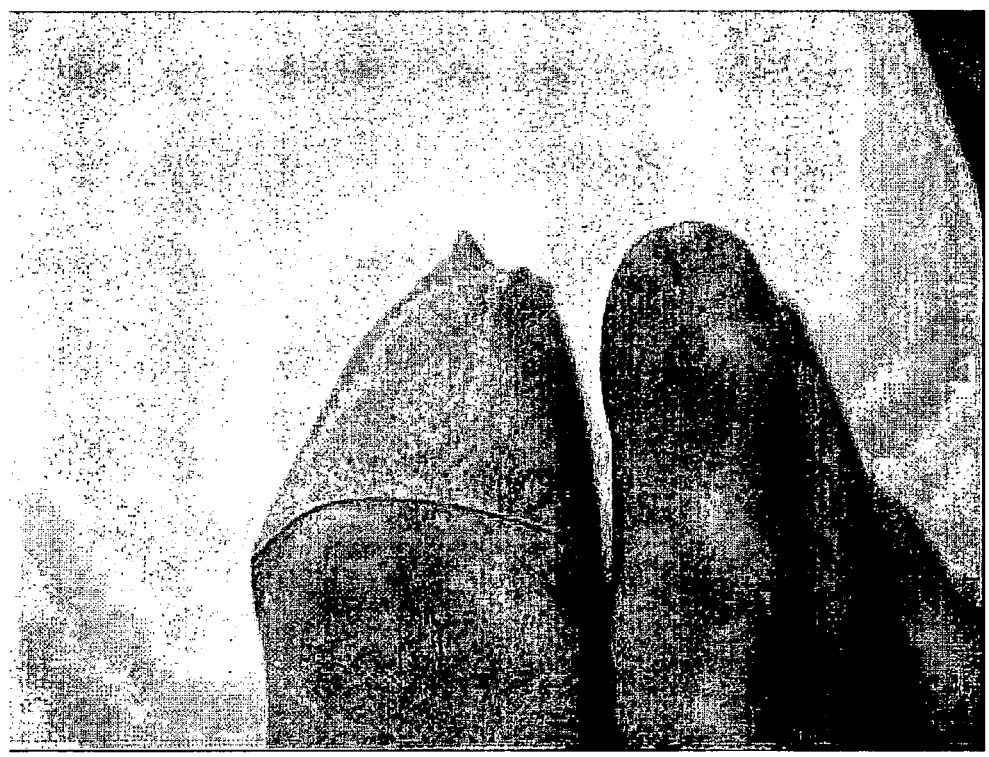
Figure 18C:
Figure 18D:

FIG. 16a shows A³IS in an alcoholic gel tested using the surface diffusion bio assay to determine zones of inhibition against S. aureus. Zones of inhibition are small due to the absorptive property of the gel matrix, but there is a clear zone around the gel matrix;

FIG. 16b shows A³IS—stability in an alcoholic gel. The A³IS in an alcoholic gel formulation was put on a short term stability study of 6 weeks, including a freeze thaw cycle and tested using the surface diffusion bio assay to determine zones of inhibition against S. aureus. Results indicated that the gel formulation maintained stability throughout the test period;

FIG. 17 shows a comparative investigation of A³IS efficacy. A³IS was poured onto the surface of a range of commercially available dressings Kaltostat® (Comvita), Kendal® (Telfa) and a Collagen-GAG (glycosaminoglycan) matrix as previously described and allowed to diffuse into the dressing for several hours. Sections were cut and placed onto agar plates, previously inoculated with S. aureus, E. coli and P. aeruginosa. The antibacterial efficacy of A³IS impregnated dressings was then compared to Aquacel® (Convatec) and Betadine® (Seton) commercially available dressings that contain elemental silver and iodine. A³IS dressings are as effective antimicrobially as Aquacel (Convatec) and Betadine® (Seton) and a commercially available dressing that use elemental silver and iodine;

FIG. 18a shows A³IS—antimicrobial activity against Onychomycosis. Onychomycosis present in a toenail prior to treatment with A³IS;

FIG. 18b shows A³IS—antimicrobial activity against Onychomycosis. A³IS covered with a bandage whose wadding is moistened using water. The nail is therefore covered in an occlusive dressing;

FIG. 18c shows A³IS—antimicrobial activity against Onychomycosis. Photograph 48 hours after initiation of A³IS treatment. It is evident that the nail has changed appearance in that it is now darker in colour; and FIG. 18d shows A³IS—antimicrobial activity against Onychomycosis. Photograph 8 weeks after initiation of A³IS treatment. In this the band of uninfected nail is clearly visible, indicating that the dermatophytes have been eliminated.

EXAMPLES

General Materials and Methods

Manuka Honey:
Manuka Care 18+® (Comvita) or Medihoney® was prepared as a 50% v/v in nutrient broth. 11 serial 1 in 2 dilutions of the 50% v/v preparation were made in nutrient broth and used for microbial inhibition testing, giving a lowest concentration of 0.01%.

Sugars:
(D+) glucose, D (−) fructose, (D+) maltose and (D+) sucrose (Sigma Aldrich)

Glucose Oxidase
0.5% glucose oxidase powder (5600 U/100 g) was used in the manufacture of A³IS. Glucose Oxidase 240 U/mg (Biozyme UK) (1 U is that amount of enzyme causing the oxidation of one micromole of glucose per minute at 25° C. and pH 7.0) and Glucose Oxidase 100 U/mg to 250 U/mg (Sigma Aldrich) (1 U will oxidize 1.0 mole of D-glucose to D-gluconolactone and H2O2 per min at pH 5.1 at 35° C.) were also used in the following Examples.

pH Adjustment:

A 50% v/v solution of Manuka honey was pH adjusted to pH6.5 with 1M NaOH and a sample of the sugar mix without glucose oxidase was pH adjusted to pH 3.8 with 1M HCl. pH was measured with a pH meter (Hanna Instruments HI 931410).

Single Sugar Preparations:

50% w/v solutions of glucose only, fructose only, and sucrose only were prepared and serially diluted in a similar manner to the Manuka honey.

Measurement of Moisture Content and Available Water (Aw):

Determination of moisture content was made using a Carl Fisher Titration apparatus (Switzerland). Determination of Aw was made using an Aqua Lab Aw meter, model series 3TE, Decagon Devices Inc. Pullman, Wash., (Kind permission Glanbia Innovation Centre, Kilkenny).

$H_2O_2$ Assay:

Hydrogen peroxide was determined following the method of (Kerkvliet 1996 and Serrano et al., 2004), using Merckoquant test strip (no. 10011; Merck, Germany).

Removal of $H_2O_2$:

Catalase (Sigma Chemical Co., from bovine liver, cat. No. C-30. 12,800 U/mg) was added to normal pH Manuka honey dilutions (initial pH 4) and to pH adjusted Manuka honey dilutions (initial pH 6.8) at the same concentrations used by Taormina et. al., Allen et. al., and Molan et. al. 1988). Typically the concentration added is 100 times greater than the measured amount of $H_2O_2$ present.

Heat Treatment of Manuka Honey:

A 50% solution of Manuka honey in nutrient broth was heat treated to a temperature of 85+/−5° C. in a water bath, this temperature was maintained for a period of 60 minutes or 120 minutes. A 50% solution of Manuka honey in nutrient broth was autoclaved at 121 psi for 15 minutes. From these heat treated honey preparations dilutions were prepared for assay.

Microbial Strains:

*Escherichia coli* (NCIMB 8545), *Staphylococcus aureus* (NCIMB 9518) and *Pseudomonas aeruginosa* (NCIMB 8626) are grown on nutrient agar or in nutrient broth for 24 hrs at 37° C.

*Candida albicans* (NCIMB 3179) and *Saccharomyces cerevisiae* are grown on sabaroud dextrose agar or in sabaroud dextrose broth for 24 hrs at 37° C.

*Propionibacterium acnes* (*P. acnes* ATCC/NTC 11827) is grown anaerobically on blood agar or in nutrient broth for 72 hrs at 37° C.

22 isolates of *Staphylococcus aureus* from clinical mastitis obtained from Sligo regional Veterinary Laboratories are grown on nutrient agar or in nutrient broth for 24 hrs at 37° C.

For testing conducted in the Sligo Regional General Hospital; five Beta haemolytic Streptococci Group A clinical isolates are grown on blood agar or in nutrient broth for 24 hrs at 37° C.

*Campylobacter coli* (NCTC 11366) is grown on brain heart infusion agar or in brain heart infusion broth for 72 hrs at 37° C.

*Campylobacter jejuni* (NCTC 11322) and three clinical isolates are grown on brain heart infusion agar or in brain heart infusion broth for 72 hrs at 37° C.

MRSA (ATCC 43300) and seven clinical isolates are grown on nutrient agar or in brain heart infusion broth for 72 hrs at 37° C.

Laboratory mould isolates are grown on sabaroud dextrose agar or in sabaroud dextrose broth for 48 hrs at 25° C.

*Botrytis cinerea* is grown on sabaroud dextrose agar or in sabaroud dextrose broth for 48 hrs at 25° C.

Bacterial growth is monitored by measuring the culture optical density (OD) in a spectrophotometer (Anthos 2010) at a wavelength of 620 nm.

Well/Disc Diffusion Methods—for Measurement of Microbial Inhibition

Agar plates are inoculated by swabbing overnight culture onto the plate surface. Plates are allowed to stand at room temperature for 15 minutes before use. Wells 8.2 mm diameter are bored into the surface of the agar. One hundred and eighty µl of sample is placed into each well. The samples diffuse into the agar around the well and are assayed for an ability to produce a zone of inhibition. Plates are incubated for 24, 48 or 72 hrs and zones of inhibition are measured using an Autodata automatic zone reader. The diameter of zones, including the diameter of the well (8.2 mm), is recorded.

For disc assays, sterile absorbent discs (8.2 mm diameter) are placed into sample dilutions for 10 minutes before being applied directly to inoculated agar plates. The samples diffuse from the disc into the agar and are assayed for an ability to produce a zone of inhibition. Plates are incubated for 24, 48 or 72 hrs and zones of inhibition are measured using an Autodata automatic zone reader. The diameter of zones, including the diameter of the disc (8.2 mm), is recorded.

Honey Bactericidal Quantifications

The agar diffusion assay (ADA) is generally the preferred method for honey bactericidal quantifications and determining biological potency for compounds/actives—antibiotics, and is used for Manuka honey production batch analysis and release procedures (Gribbles Analytical Laboratories Kerkvliet, J. D., 1996. Screening method for the determination of peroxide accumulation in honey and relation with UMF content (*Journal of Apiculture Research*. 35, 3, pp. 110-117). However, the subjective nature of this assay limits the interpretation of results. It is also time consuming and laborious, requiring preparation and cooling of plates, boring of test wells in agar and manual measuring of inhibition zones after 24 hrs of incubation. The quality of results depend largely on technique and judgment, and the suggested precision cannot be obtained when the inhibition zone is unclear or not perfectly circular.

Other Methods—for Measurement of Microbial Inhibition

Microbial growth, or inhibition of growth, can be detected using a variety of biological methods, including, direct microscopic counts, absorbance, bioluminescence, assays that incorporate a colorimetric, and fluorometric growth indicator, turbidity, dry weight and zones of inhibition.

Spectrophotometric Assay

We developed a spectrophotometric assay using 96 well microtiter plates (Patton T. et al Journal of Microbiological Methods (2006) pages 84-95) and compared this method to the standard methods of well/disc diffusion in order to evaluate the potential advantages of this bioassay for evaluation of the antibacterial properties of Manuka honey. Increased automation and throughput (efficiency) were achieved using the spectrophotometric assay which can rapidly generate large amounts of data making possible a detailed statistical analysis of results. The method is more sensitive, and more amenable to statistical analysis than the assays currently employed, permitting extensive kinetic studies even in the presence of low honey concentrations (Table 1). The assay is capable of detecting inhibitory levels below that recorded for well or disc diffusion assays. This assay provides a quick and sensitive method for elucidating the activity of Manuka honey.

TABLE 1

| Microbial species | Disc Assay MIC50 | Well Assay MIC50 | Spectrophotometric Assay MIC50 |
| --- | --- | --- | --- |
| Escherichia coli | 22.4% | 24.5% | 5.6% |
| Staphylococcus aureus | 25.7% | 22.6% | 0.78% |
| Bacillus cereus | 24% | 21.9% | 2.00% |
| Candida albicans | No inhibition | No inhibition | 40% |

MIC50 Values Indicate Percent Manuka Honey Present Resulting in a 50% Inhibition in Growth of a Test Micro-Organism.

Honey dilutions are inoculated with a 5% v/v of overnight test culture. Two hundred microliters of each dilution, using 8 replicates per dilution, are applied to wells of a flat bottom 96 well microtiter plates with lid to prevent cross contamination (Costar, Corning Ltd. NY). Control wells received 200 microliters of 5% culture inoculated broth. Optical density is determined in a spectrophotometer at 620 nm prior to incubation, ($T_0$). Plates are incubated for 24 hrs in the dark on a Certomat MO orbital shaker at 100 rpm to prevent adherence and clumping. After 24 hrs plates are again read in a spectrophotometer at 620 nm, ($T_{24}$). Results shown are averages from eight determinations repeated five times on three separate days.

The OD for each replicate at $T_0$ is subtracted from the OD for each replicate at $T_{24}$. The adjusted OD of each control well is then assigned a value of 100% growth. The growth inhibition for the test wells at each dilution is determined using the formula:

Percent Inhibition=1−(OD test well/OD of corresponding control well)×100 for each row of the 96 well plate e.g. OD row 1, column 1, well 1 (test) is divided by the OD value of Row 1, column 12, well 12 (control).

This yield eight replicate inhibition values for each honey dilution. All assays are repeated a minimum of three times on three different days using a minimum of three plates per test, i.e. each data point reported is an average from a minimum of 72 point determinations.

The standard deviation associated with the average calculated inhibition values for replicate wells is determined and is plotted as associated error bars for each data point on graphs. Where the resulting measurement recorded a negative inhibition value (growth promotion) this is reported as stimulation using the formula:

Percent Growth=(*OD* test/*OD* control)×100.

Example 1

Figure 1A:
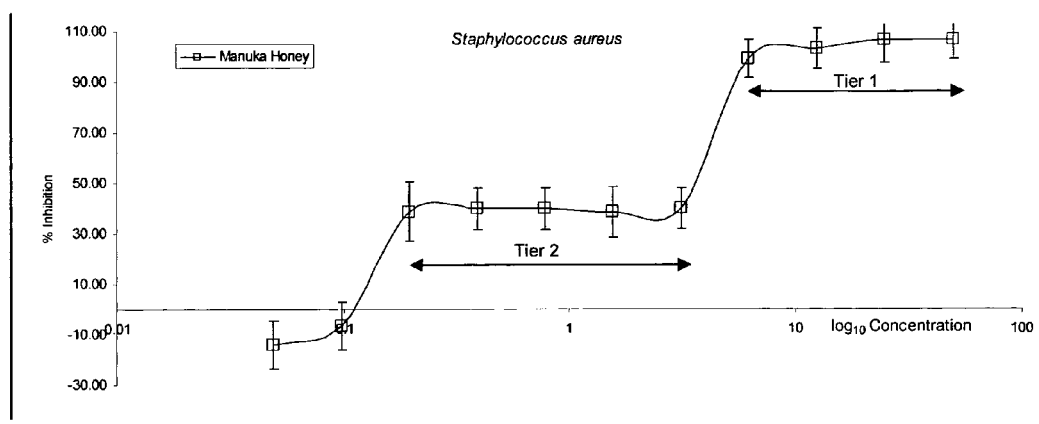

Characterisation of Antimicrobial Activities in Manuka Honey—Absence of Endogenous Hydrogen Peroxide Using the Spectrophotometric bioassay described, antimicrobial activity of commercially available Manuka honey is determined, using several samples to ensure consistency. Results shown in FIG. 1a demonstrate that Manuka honey provides a first tier of microbial inhibition activity at dilutions 50% to approximately 6.25% and a second tier of microbial inhibition activity at dilutions 3.125% to approximately 0.195%

This two tier effect is shown to be produced by separate mechanisms. Initial microbial inhibition on low honey dilution (50%-6.25%) results from a combination of low pH and growth limiting Aw (Available Water) and a very minor role by hydrogen peroxide, which is only produced de-novo upon dilution and after a considerable period of time has elapsed. There is no detectable endogenous hydrogen peroxide present in diluted or undiluted Manuka honey, as shown in Table 2

TABLE 2

| | % Dilution | | | |
| --- | --- | --- | --- | --- |
| | 50.00 | 25.00 | 12.50 | 6.25 |
| Manuka honey | pH 3.89 | pH 4.35 | pH 4.96 | pH 5.95 |
| $H_2O_2$ mg/L (Time 0 hrs) | 0 | 0 | 0 | 0 |
| Manuka honey | pH 3.89 | pH 4.35 | pH 4.96 | pH 5.95 |
| $H_2O_2$ mg/L (Time 3 hrs) | 0 | 35 | 35 | 65 |

Manuka Honey $H_2O_2$ Generation Profile

As the concentration of the honey is diluted, and after a period of time has elapsed, hydrogen peroxide is produced and further contributes to the antimicrobial effect.

Figure 1B:
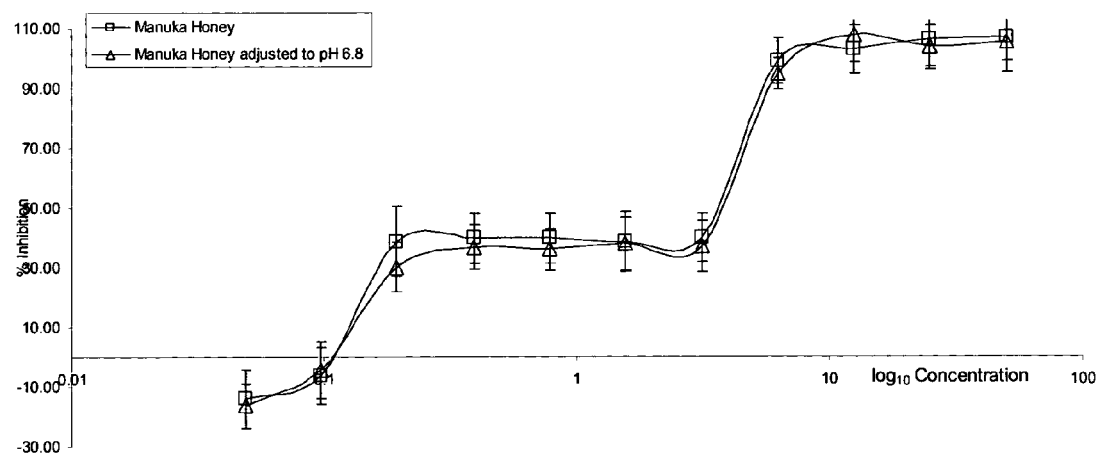
Figure 1C:
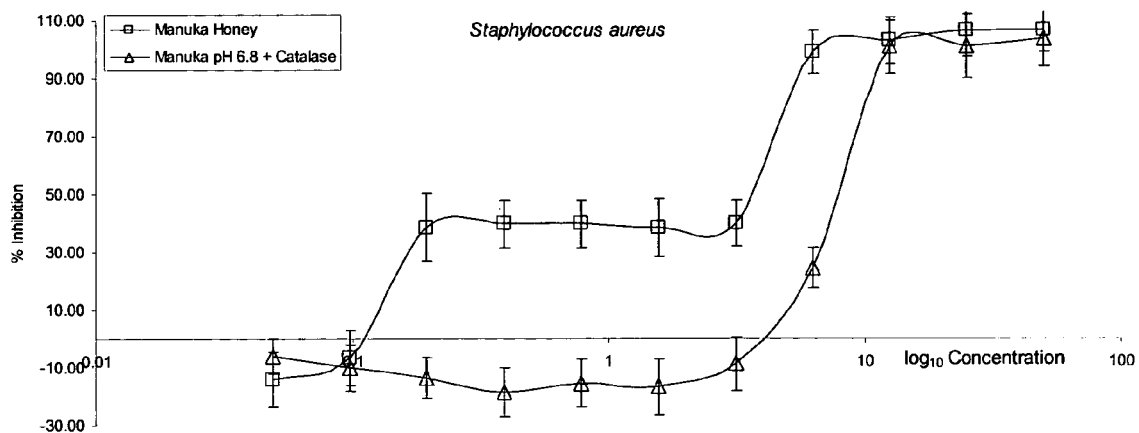

Adjusting the pH of Manuka honey from its natural pH of approximately 4.0 to a near neutral pH of 7.0 does not significantly affect the antimicrobial profile FIG. 1b. When Manuka honey dilutions are pH adjusted to near neutral followed by the addition of catalase in excess, the antimicrobial profile of the honey is altered FIG. 1c. The first tier of antimicrobial inhibition is only slighted affected but the second tier is significantly affected indicating that the antibacterial effect in the second tier is primarily the result of hydrogen peroxide liberation.

The belief that a non peroxide activity also referred to as Unique Manuka Factor (UMF) exists is due to an experimental procedural oversight. Specifically, the failure by other research groups to neutralise the pH of Manuka honey prior to catalase addition essentially renders the added catalase ineffective as the honey pH is too acidic for catalase activity. As honey to which excess catalase has been added still retains antimicrobial activity the belief that a UMF exists has persisted. As FIG. 1b shows, adjusting the pH of Manuka honey to pH 6.80 does not affect the antimicrobial activity. A pH of 6.80 is close to the optimum pH for catalase activity and under this condition the added catalase does neutralise the hydrogen peroxide activity thereby altering the antimicrobial activity profile of the honey.

Surprisingly, we also found that this glucose oxidase pathway is not operational immediately on application of Manuka honey and is only operational following dilution of the honey and after a period of time has elapsed.

Example 2

A Prototype Antimicrobial Endogenous and Sustained Release Hydrogen Peroxide Generating System A prototype formulation containing 31+/−5 g glucose: 35+/−5 g fructose: 7+/−2 g maltose: 1.5+/−1 g sucrose is made by mixing the ingredients, making the mixture up to a final volume of 100 ml in distilled deionized (DI) water; the mixture is sterilized by autoclaving. Glucose oxidase at 0.05% by weight, which is a similar concentration to that contained in Manuka honey, is added.

Figure 2:
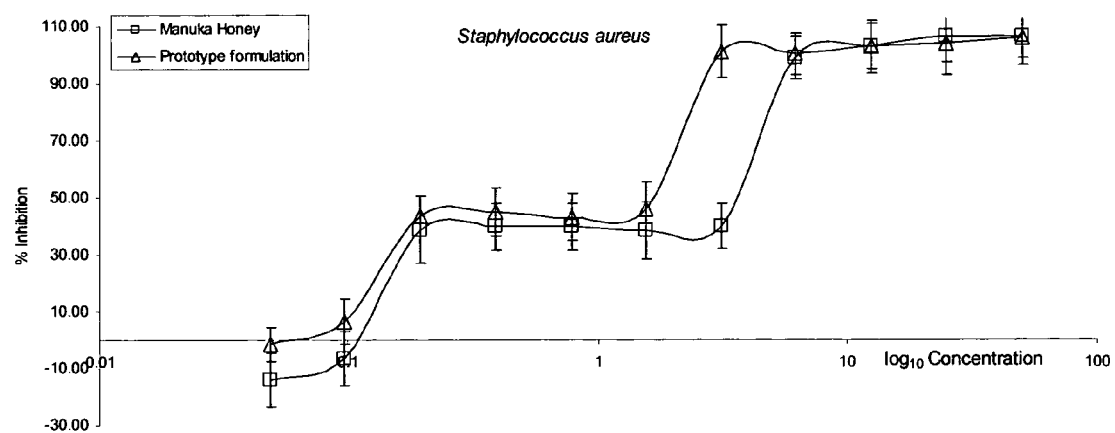

FIG. 2 shows the results of an antimicrobial assay on *S. aureus* using this prototype formulation. The prototype formulation of this example demonstrated a greater activity compared to Manuka honey. It is probable that the critical role played by the glucose oxidase enzymatic pathway in the antibacterial effect is enhanced once free from impurities and reaction limiting compounds (such as catalase) present in honey. This prototype demonstrates very effective bactericidal activity.

Example 2.1

Figure 3A:
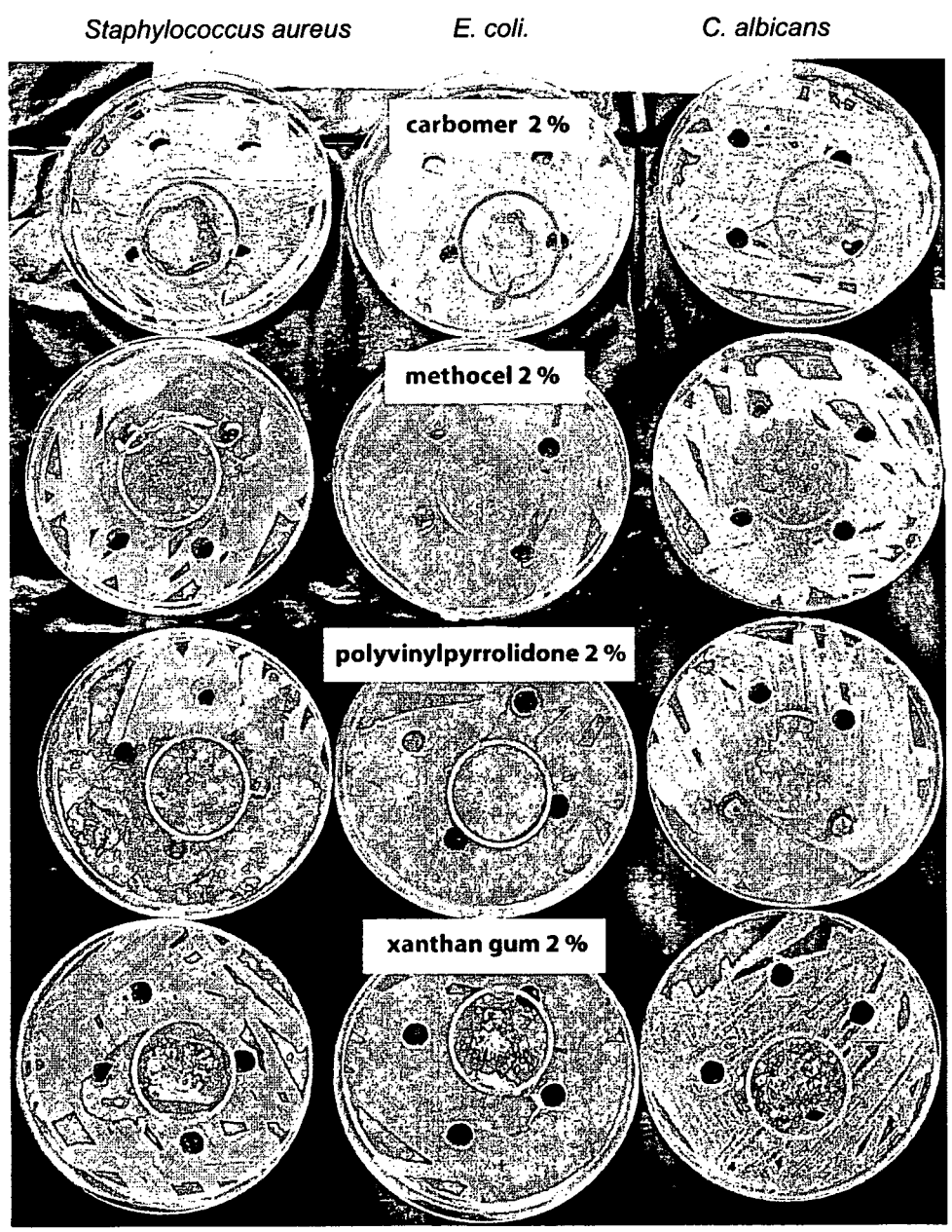
Figure 3B:
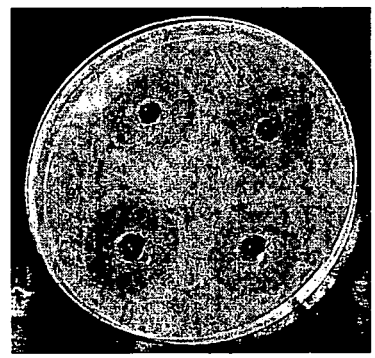

A Gel Prototype Antimicrobial Endogenous and Sustained Release Hydrogen Peroxide Generating System Gelling agents that are common ingredients in topical pharmaceutical formulations are added to the prototype formulation and tested. Gels tested include water reconstituted cellulose and alcohol reconstituted cellulose agents (1. carbomer, 2. methocel, 3. polyvinylpyrrolidone and 4. xanthan gum at 2% in a hydrogel incorporating the prototype formulation). Both cellulose based gels demonstrate a decrease in stability. It is possible that steric hindrance and hydrolysis of the glucose oxidase result in loss of antibacterial activity. Even before loss of activity, due to decreased stability, neither gel formulations is as active as the prototype formulation, as evidenced by the smaller zones of inhibition in diffusion assays (compare FIG. 3*a* (gels) with FIG. 3*b* (prototype formulation)).

Example 2.2

Figure 4A:
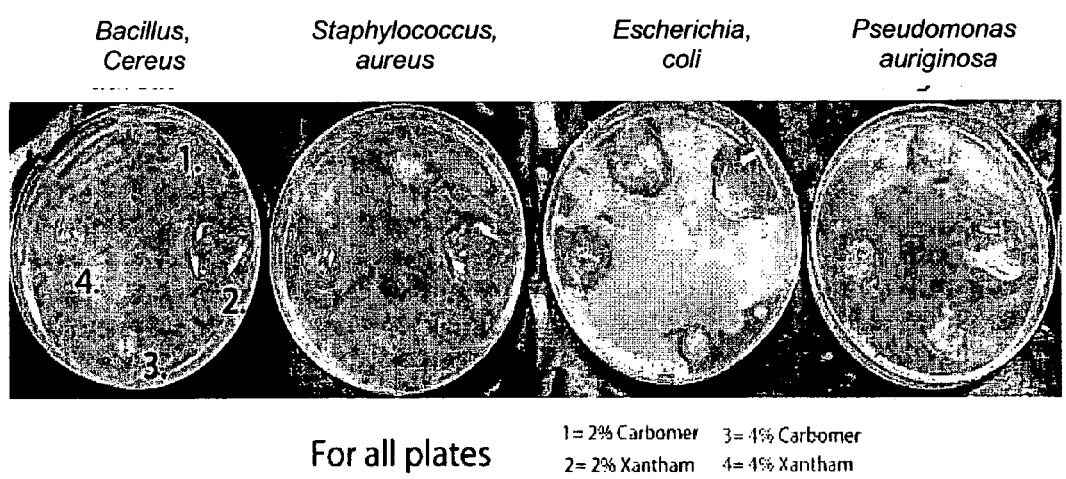

A Prototype Antimicrobial Endogenous and Sustained Release Hydrogen Peroxide Generating System—Single Sugar & Enzyme Gel Formulation In an attempt to resolve the gel stability described in Example 2.1, formulations containing glucose and glucose oxidase only are made. Glucose formulations ranging from 30%-80% glucose in water are autoclaved or warmed slowly to boiling point to aid in dissolution of the sugar. During dissolution by boiling, various gelling agents are added and when cooled to below 40° C. 0.1% glucose oxidase is added. These formulations are tested for antibacterial activity (FIG. 4*a*).

Figure 4B:
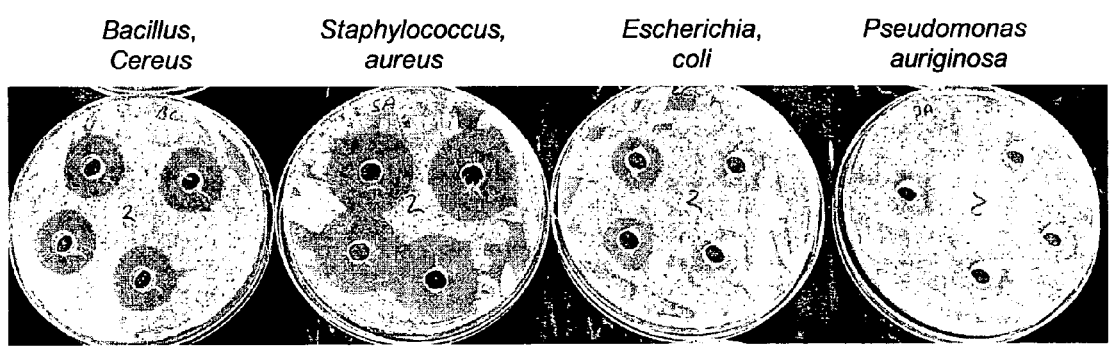

These formulations demonstrate only a limited degree of antibacterial activity and this activity is below that observed with the prototype antimicrobial formulation described in Example 2 as evidenced by the smaller zones of inhibition in Well/Disc diffusion assays (compare FIG. 4*a* (gels) with FIG. 4*b* (prototype)).

In addition to the reduced activity, the formulations containing the high glucose concentrations, when placed into aluminium tubes, solidify making the formulations unusable. The tubes containing formulations with lower concentrations of glucose demonstrate a lack of stability as evidenced by a decrease in antimicrobial activity over time.

Example 2.3

Improved Formulation Characteristics of Antimicrobial Endogenous and Sustained Release Hydrogen Peroxide Generating System—Varying the Carbohydrate and Water Concentration This example describes attempts to minimise the quantity of water present in formulations according to the invention, to minimise problems relating to stability as excess water may give rise to hydrolysis of the glucose oxidase. The formulations still require sufficient water to permit generation of $H_2O_2$, ease of application and to prevent precipitation of sugars during storage. Varying concentrations of sugars are mixed and heated as described in example 2.2 to determine the primary source for the precipitation and granular texture observed in earlier formulations. From this analysis, sugar concentrations are adjusted to reduce this effect. Following the addition of enzyme, suitable formulations are tested to determine antibacterial activity.

It is found that the concentration of water could be reduced from 20% to 10% which is the minimum concentration permitting enzyme activity, ease of application and prevention of sugar precipitation.

Uncontrolled heat treatment of sugars tends to produce carmelisation resulting in a formulation that acquires a yellow to brown colouration. To eliminate carmelisation, and thereby produce a clear material, a manufacturing process is developed in which the order of addition of sugars and their dissolution by heating is carefully selected to circumvent the carmelisation process. Glucose oxidase enzyme is added to this formulation and antibacterial activity, stability and suitability for application were assessed. These improvements to the Prototype formulation form the basis for all future formulations/systems described herein.

Example 3

Single Component Antimicrobial System, Having an Endogenous Hydrogen Peroxide Reservoir and Sustained Release A formulation for a single component antimicrobial system (hereafter referred to as 'Antimicrobial System' or $A^3IS$ or A3IS is made in accordance with Table 3.

TABLE 3

| Ingredient | Percentage by weight |
| --- | --- |
| Purified water | 13.5 adjusted to make 100% |
| Fructose Powder | 35% +/− 5 |
| Glucose Powder | 38% +/− 5 |
| Maltose Powder | 10% +/− 5 |
| Sucrose Powder | 1.5% +/− 1 |
| Glucose Oxidase Powder | 0.5% enzyme (5600 U/g) pre-dissolved in 1.5% of purified water |
| TOTAL | 100% |

The pH of $A^3IS$ is set at pH 5.5. This low pH is within the glucose oxidase range of activity (pH 4.0-7.0 optimum pH of 5.5). If needed, a buffer can be added to obtain the desired pH, as illustrated in Table 4. The buffer is pre-dissolved in purified water and replaces part of the purified water from the formulation above.

TABLE 4

| Optional Buffering Ingredients for pH 5.5 | Percentage by weight |
|---|---|
| Citric Acid/Sodium Citrate | 0.918% pre-dissolved in 2% of purified water for pH 5.5 |
| Phosphoric Acid/Disodium hydrogen phosphate | 1.598% pre-dissolved in 2% of purified water for pH 5.5 |

It will be understood that different ratios of buffering ingredients can be used depending on the desired pH.

It will be understood that Prototype, described in Example 2 and A³IS described here give formulations suitable for use according to the invention. The subsequent Examples show analysis of various characteristics of A³IS.

The sugars described in Table 3 are added in the following sequence: fructose, glucose, maltose and sucrose. Each carbohydrate is dissolved fully in the water by heating to approximately 90° C. before the next carbohydrate is added. Alternatively the sugars can be prepared as above but under a vacuum at −0.5 Bar, which reduces the boiling point of the sugars to a temperature of less than 90° C. preventing discoloration.

When the carbohydrates are fully dissolved and clear, the mixture is allowed to cool to below 60° C. and optional buffering ingredients pre-dissolved in water are added to the main mixture.

When the base mixture is at a temperature below 40° C., a temperature which allows retention of enzyme activity, the glucose oxidase enzyme which is pre-dissolved in water is added and dispersed into the mixture. The mixture is allowed to cool to room temperature. When cool, the mixture is dispensed into aluminium tubes which are then sealed. Tubes are stored at room temperature.

Example 3.1

A Prototype Antimicrobial Endogenous and Sustained Release Hydrogen Peroxide Generating System—Varying the Enzyme Concentration and Type Honey is known to contain several enzymes in addition to glucose oxidase, including diastase and invertase. Diastase and invertase enzymes are incorporated into the prototype formulation of Example 2 to determine if they can enhance overall antibacterial activity by allowing for a slower but sustained release of $H_2O_2$ by acting on different carbohydrates in the formula.

We investigate several combinations and concentrations of enzyme to determine this potentially enhanced antibacterial activity. Diastase and invertase in differing combinations are added to the A³IS and compared to A³IS containing glucose oxidase only. We find no improvement in antibacterial activity in any of the formulations containing multi enzymes.

Figure 5A:
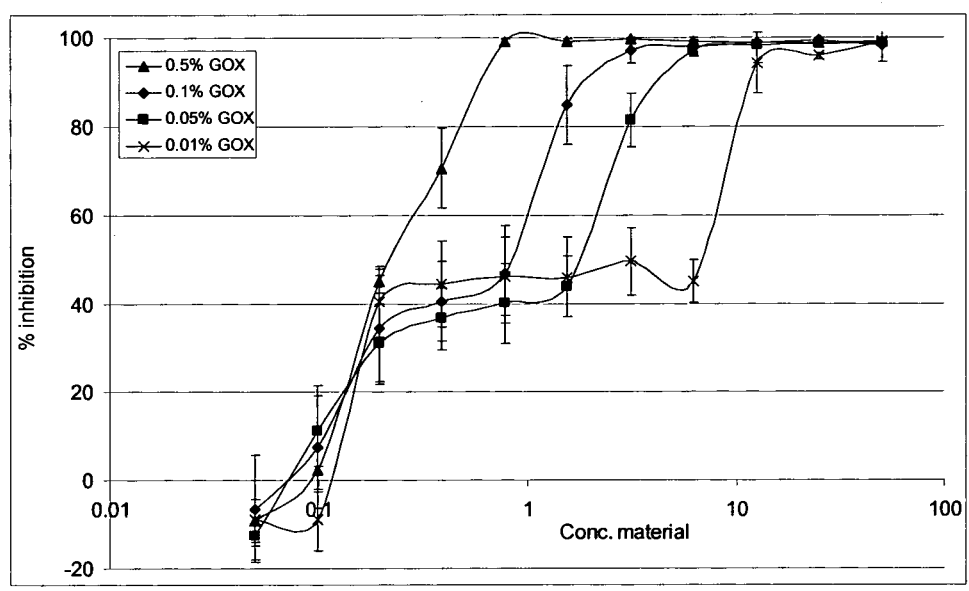

Different concentrations of glucose oxidase are also incorporated and compared by spectrophotometric assay to determine their quantity/activity relationship. The antibacterial activity of A³IS increases proportionally to the concentration of glucose oxidase. A substantial antibacterial effect is attained at an enzyme concentration of 0.05% (FIG. 5a).

This shows that a range of antibacterial activity can be achieved by varying the concentration of glucose oxidase. The enzyme can be dispersed with ease throughout the material during mixing.

Example 4

A³IS—an Innovative and Augmented Hydrogen Peroxide Generating System

Hydrogen peroxide is quantified following the method of (Kerkvliet 1996 and Serrano et al., 2004), using Merckoquant test strip (no. 10011; Merck, Germany). Results are expressed in milligrammes $H_2O_2$ per liter. The suitability of the method for hydrogen peroxide determination is verified by spiking freshly prepared Manuka honey dilutions with liquid $H_2O_2$ and verifying that the assay could accurately detect the quantity of $H_2O_2$ present.

Figure 5B:
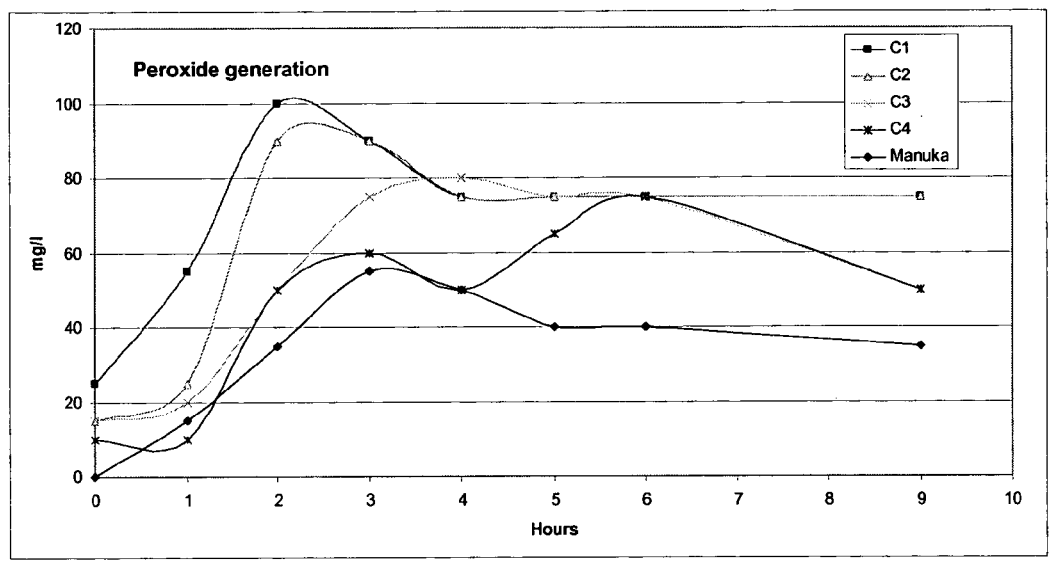

Table 5 and FIG. 5b show that A³IS, with 0.5% sigma Aldrich GOX enzyme 5600 U/g and diluted 50% (C1), 25% (C2), 12.5% (C3) or 6.25% in de-ionised water (DI) generate significantly increased levels of hydrogen peroxide compared with Manuka honey diluted at 50% in DI water.

TABLE 5

| | Sample/mg H2O2/l | | | | |
|---|---|---|---|---|---|
| Time hr. | C1 | C2 | C3 | C4 | Manuka |
| 0 | 25 | 15 | 15 | 10 | 0 |
| 1 | 55 | 25 | 20 | 10 | 15 |
| 2 | 100 | 90 | 50 | 50 | 35 |
| 3 | 90 | 90 | 75 | 60 | 55 |
| 4 | 75 | 75 | 80 | 50 | 50 |
| 5 | 75 | 75 | 75 | 65 | 40 |
| 6 | 75 | 75 | 75 | 75 | 40 |
| 9 | 75 | 75 | 50 | 50 | 35 |

Figure 5C:
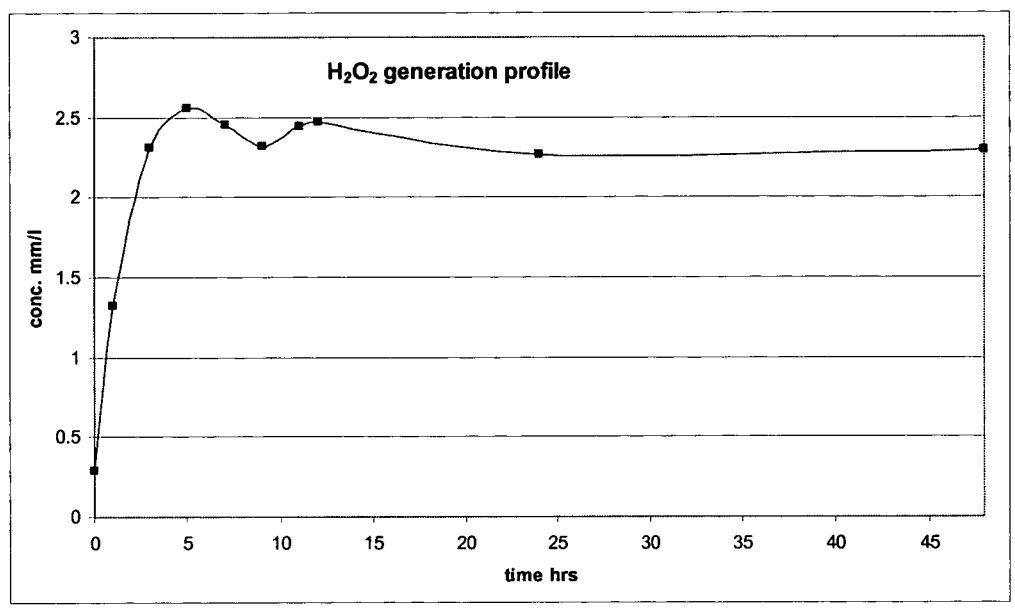

FIG. 5c shows this increased production of hydrogen peroxide (A³IS diluted 25% in DI water) is maintained for a period of at least 48 h.

Example 4.1

Figure 5D:
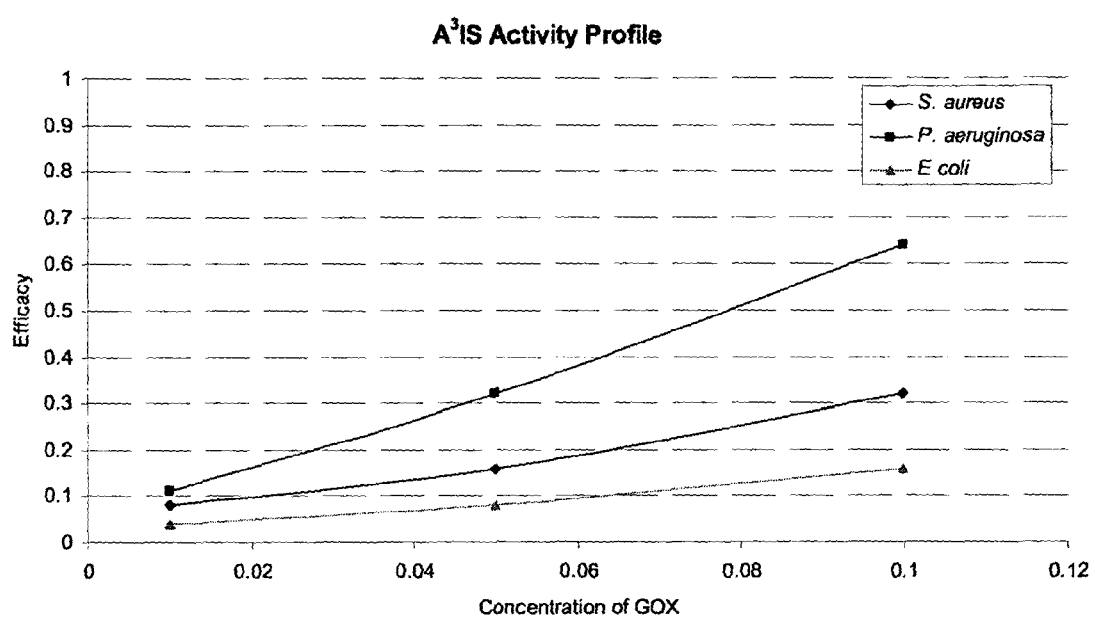

A³IS—Antimicrobial Activity Increased with Increased Glucose Oxidase Concentration FIG. 5d shows a dose response relationship between the concentration range of glucose oxidase and antimicrobial effect on S. aureus, as measured using a spectrophotometric inhibition bioassay.

FIG. 5d further demonstrates that it is possible to address the issue of potency/efficacy, as the formulations produced may be adjusted by variations of the concentration of glucose oxidase which is incorporated during manufacture, results shown on Staphylococcus aureus, Pseudomonas aeruginosa and Escherichia coli.

Example 5

A³IS—Endogenous Hydrogen Peroxide Reservoir

When A³IS is mixed with water within the dilution range 50% to 0.1% the liberation of hydrogen peroxide is detected immediately. Table 6 shows that up to 75 mg/L hydrogen peroxide is detected at T=0. This is in contrast to Manuka honey which fails to register any liberation of peroxide at time zero (See Example 1 Table 2) and demonstrates the presence of a significant endogenous reservoir of hydrogen peroxide generated during the formulation process.

Also, after three hours of incubation of diluted samples the amount of peroxide detected in A³IS significantly exceeds that detected in the natural honey, Table 6.

TABLE 6

| | % Dilution | | | | | | | | | | | |
|---|---|---|---|---|---|---|---|---|---|---|---|---|
| | 50.00 | 25.00 | 12.50 | 6.25 | 3.13 | 1.56 | 0.78 | 0.39 | 0.20 | 0.10 | 0.05 | 0.025 |
| Manuka | | | | | | | | | | | | |
| Normal pH | 3.89 | 4.35 | 4.96 | 5.95 | 6.60 | 6.87 | 7.03 | 7.11 | 7.12 | 7.14 | 7.15 | 7.15 |
| Normal pH Aw | 0.908 | 0.970 | 0.985 | 0.994 | 0.994 | 0.995 | 0.996 | 0.996 | 0.996 | 0.996 | 0.996 | 0.997 |
| % water | 53.0 | 74.7 | 84.5 | 91.3 | N/A | N/A | N/A | N/A | N/A | N/A | N/A | N/A |
| $H_2O_2$ mg/L (T = 0 hours) | 0 | 0 | 0 | 0 | 0 | 0 | | | | | | |
| $H_2O_2$ mg/L (T = 3 hours) | 0 | 35 | 35 | 65 | 55 | 40 | 40 | 35 | 30 | 0 | 0 | 0 |
| Adjusted pH | 6.6 | 6.6 | 6.88 | 7.02 | 7.10 | 7.13 | 7.18 | 7.20 | 7.20 | 7.21 | 7.21 | 7.21 |
| Adjusted pH Aw | 0.906 | 0.966 | 0.983 | 0.990 | N/A | N/A | N/A | N/A | N/A | N/A | N/A | N/A |
| $A^3IS$ | | | | | | | | | | | | |
| Normal pH | 5.5 | 6.0 | 6.96 | 7.05 | 7.13 | 7.17 | 7.17 | 7.19 | 7.2 | 7.21 | 7.21 | 7.19 |
| Normal pH Aw | 0.906 | 0.964 | 0.983 | 0.990 | 0.995 | 0.996 | 0.997 | 0.997 | 0.997 | 0.997 | 0.997 | 0.997 |
| % water | 52.4 | 71.8 | 83.9 | 90.7 | N/A | N/A | N/A | N/A | N/A | N/A | N/A | N/A |
| $H_2O_2$ mg/L (T = 0 hours) | 75.0 | 75.0 | 75.0 | 75.0 | 70.0 | 60.0 | 55 | 55 | 45 | 5 | 0 | 0 |
| $H_2O_2$ mg/L (T = 3 hours) | 90 | 90 | 75 | 80 | — | — | — | — | — | — | — | — |
| Adjusted pH | 3.8 | 5.6 | 6.55 | 6.9 | 7.03 | 7.12 | 7.17 | 7.19 | 7.20 | 7.21 | 7.21 | 7.21 |
| Adjusted pH Aw | 0.904 | 0.964 | 0.982 | 0.991 | N/A | N/A | N/A | N/A | N/A | N/A | N/A | N/A |

This endogenous reservoir, shown here ranging between 10 and 75 mg/l hydrogen peroxide depending on the quantity of GOX present in the $A^3IS$, is shown in FIG. 5a, FIG. 5b and Table 6. Such a reservoir advantageously provides hydrogen peroxide, and its antimicrobial activity, for immediate effect upon application of $A^3IS$. Combined with higher level of hydrogen peroxide produced upon dilution, this would be expected to contribute to a significantly increased antimicrobial effect compared with other systems such as Manuka honey.

Example 6

$A^3IS$—Endogenous Hydrogen Peroxide Reservoir is Storage Stable

Figure 6:
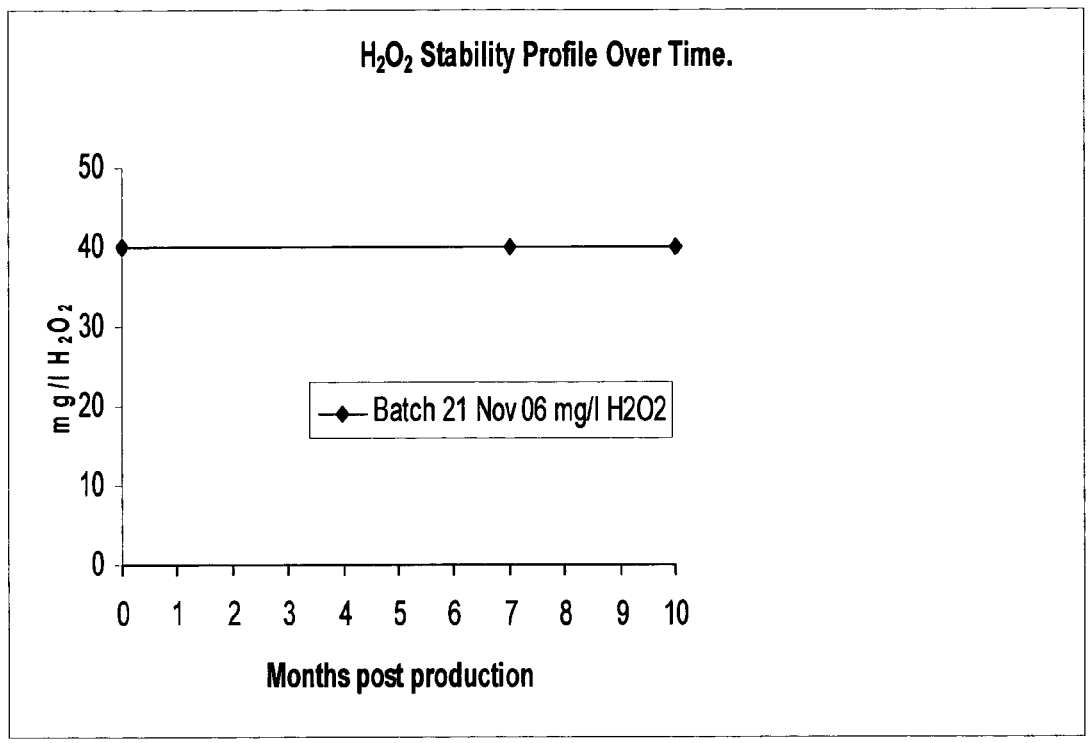

A surprising and advantageous feature of $A^3IS$ is the retention of both antimicrobial activity and the hydrogen reservoir over time as shown in FIG. 6.

Figure 7A:
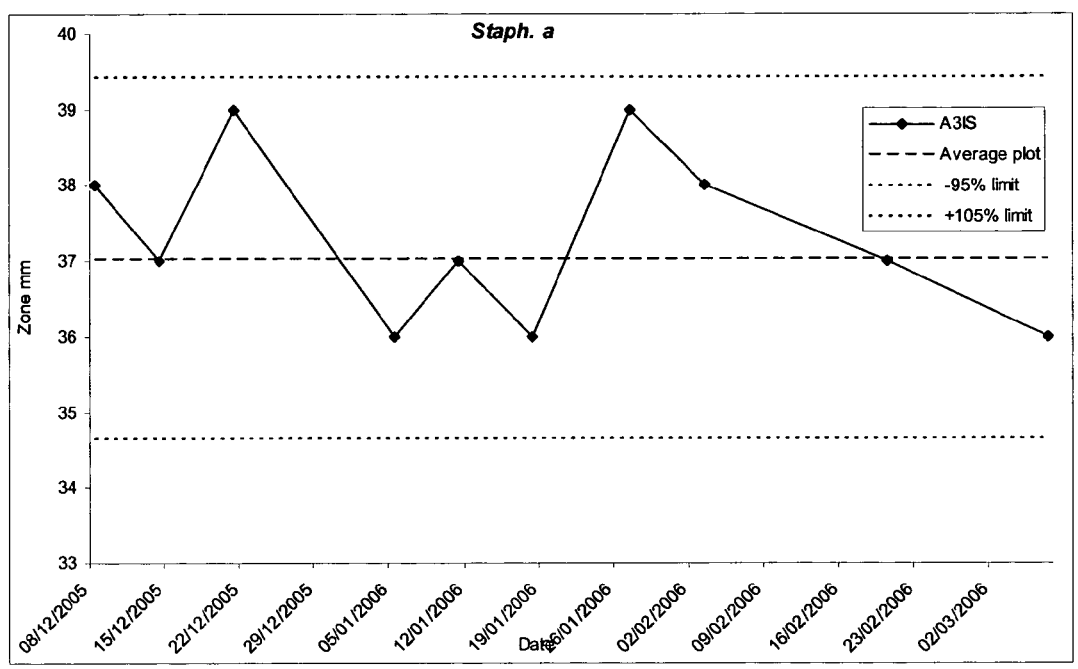
Figure 7B:
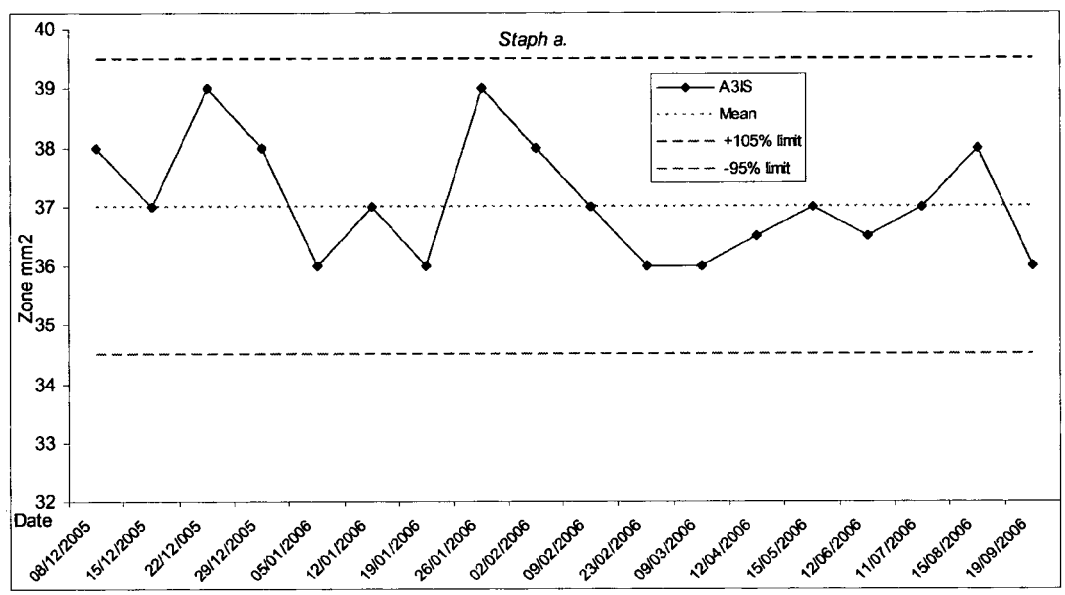

The available $H_2O_2$ reservoir produced by $A^3IS$ is storage stable as batches placed on stability retain the same levels of $H_2O_2$ as that detected when the batches are initially produced. Retention through stability of immediately available $H_2O_2$ is a unique feature of the $A^3IS$ formulations. Using the well diffusion assay to assess antimicrobial activity we demonstrate that a consistent level of antimicrobial activity is maintained over time. FIG. 7a shows the zones of inhibition measured at each sampling time point and the results graphed using 95% confidence limits during a period of three months. Similarly FIG. 7b shows extended stability of antimicrobial activity over a 9 month period. Extended stability data indicates that the $A^3IS$ formulation shows no loss of activity even after a period of 14 months.

Using the well diffusion assay to assess antimicrobial activity we demonstrate that a consistent level of antimicrobial activity over time. FIG. 7a shows the zones of inhibition measured at each sampling time point and the results graphed using 95% confidence limits during a period of three months. Similarly FIG. 7b shows extended stability of antimicrobial activity over a 9 month period. Extended stability data indicates that the $A^3IS$ formulation shows no loss of activity even after a period of 14 months.

Example 7

$A^3IS$—Potent Antimicrobial Activity Against *Staphylococcus aureus*

Figure 8A:
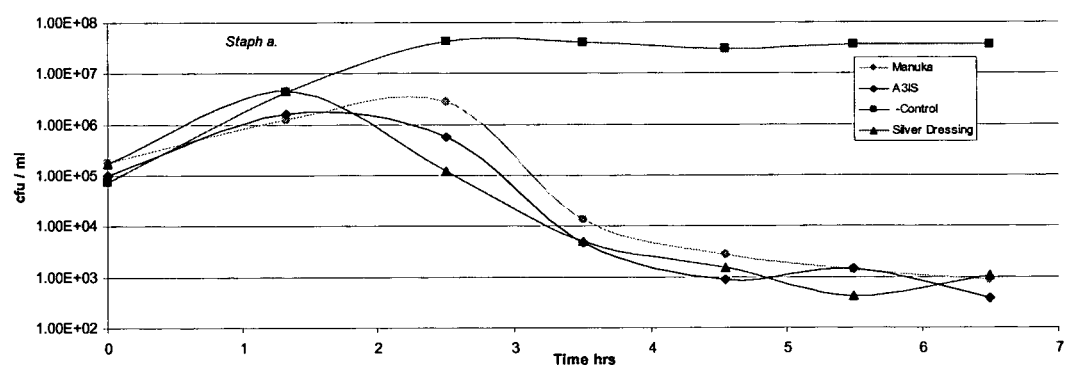
Figure 8B:
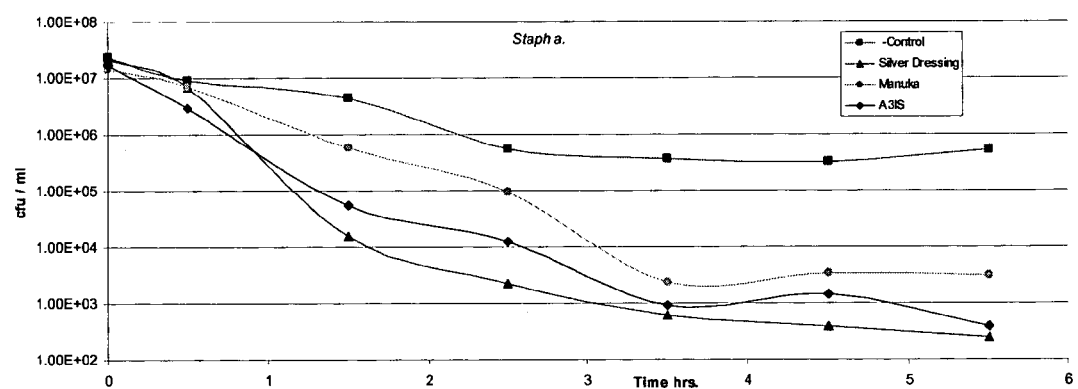

$A^3IS$ is shown to have antimicrobial activity against *Staphylococcus aureus*. FIG. 8a and FIG. 8b shows bacterial kill curves performed using two separate protocols, the NCCLS guidelines, method (FIG. 8a) and a Medical device manufacturer's specific protocol (FIG. 8b) over a 6.0 hour period. $A^3IS$ has increased efficacy compared with Manuka honey and comparable efficacy to silver dressing.

Figure 8C:
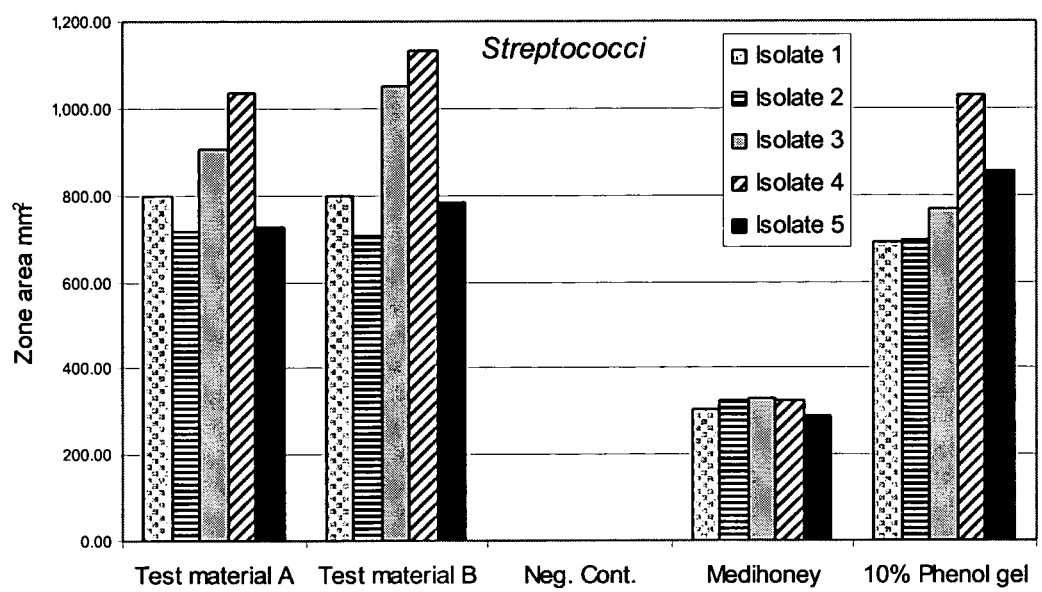

FIG. 8c shows the results of an inhibition assay (3 day repeats) for $A^3IS$, Medihoney® and a 10% phenol gel when tested against 5 clinical isolates of the Beta haemolytic Streptococci Group A. $A^3IS$ is at normal pH 5.5 (test material A) and pH 7 (test material B), a negative control of $A^3IS$ containing no GOX is included. Formulation $A^3IS$ demonstrates comparable in vitro efficacy to a 10% phenol gel and is superior to Medihoney®.

Example 8

$A^3IS$—Potent Antimicrobial Activity Against *Campylobacter*

Figure 8D:
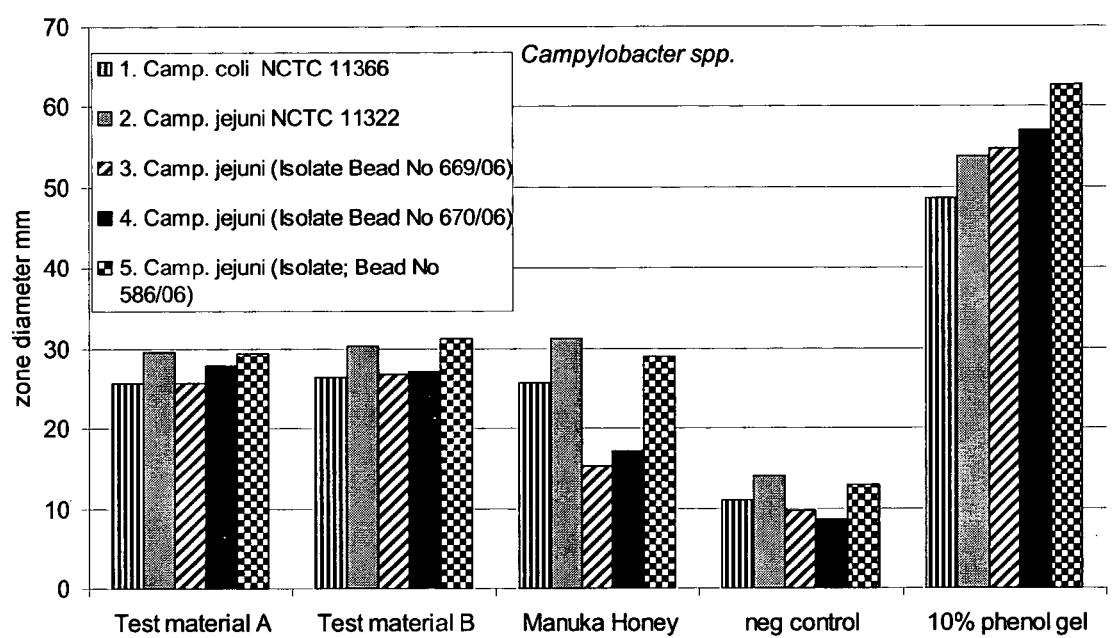

$A^3IS$ is shown to have antimicrobial activity against *Campylobacter*. FIG. 8d shows the results of an inhibition assay (3 day repeats) for formulation $A^3IS$, Manuka honey and a 10% phenol gel when tested against 5 clinical isolates of the *Campylobacter* spp. Formulation $A^3IS$ is at normal pH 5.5 (test material A) and pH 7 (test material B), a negative control $A^3IS$ containing no GOX is included. Results indicate significant anti-*Campylobacter* in-vitro efficacy and the superiority of $A^3IS$ over Manuka honey.

Example 9

$A^3IS$—Potent Antimicrobial Activity Against *Propionibacterium acnes*

$A^3IS$ is shown to have antimicrobial activity against *Propionibacterium acnes* (*P. acnes*).

Figure 9A:
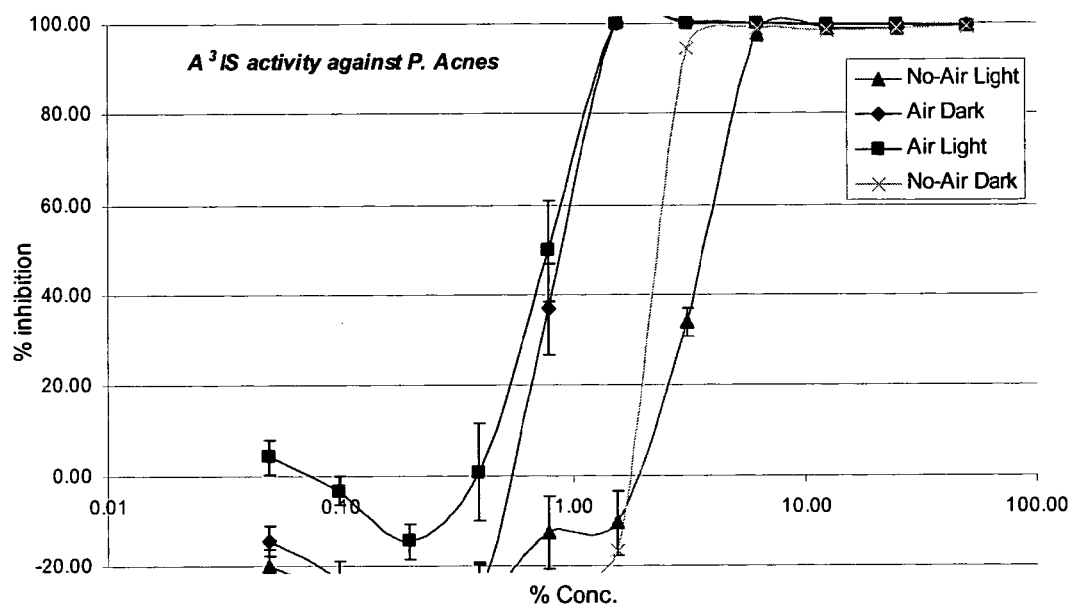
Figure 9B:
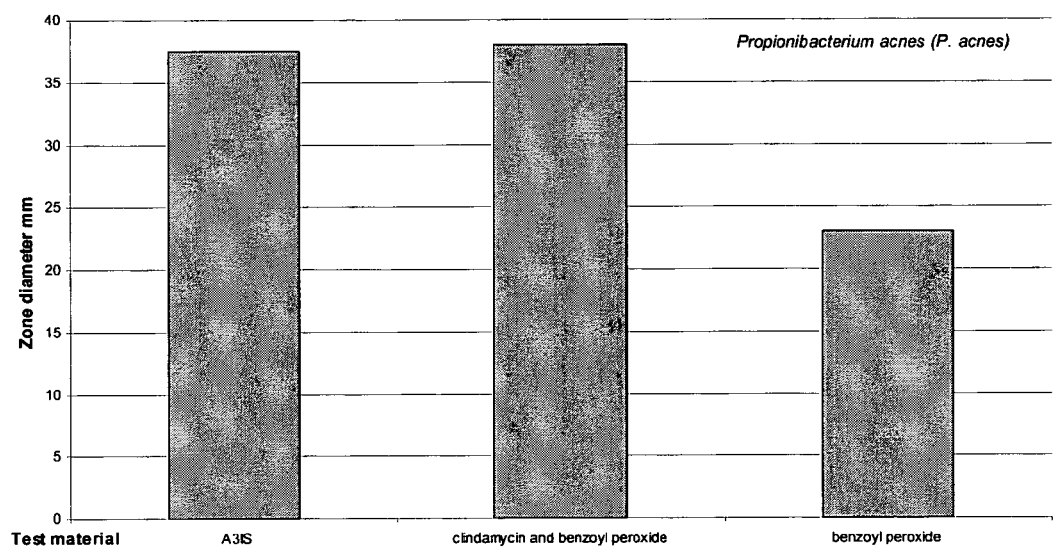

FIG. 9a. shows the inhibition results of $A^3IS$ against *P. acnes* under varying incubation conditions: light and dark aerobic, light and dark anaerobic. $A^3IS$ demonstrates a high level of activity against *P. acnes*, indicating the material may have potential for topical acne application. The results for $A^3IS$ and currently available anti-acne commercial products including some commercial products which incorporate antibiotics are shown in FIG. 9b. These results indicate that $A^3IS$ is comparable with 'respect to' in vitro anti-acne efficacy to commercially available anti-acne products containing Clindamycin and Benzoyl peroxide.

Example 10

$A^3IS$—Potent Antimicrobial Activity Against MRSA

Figure 10:
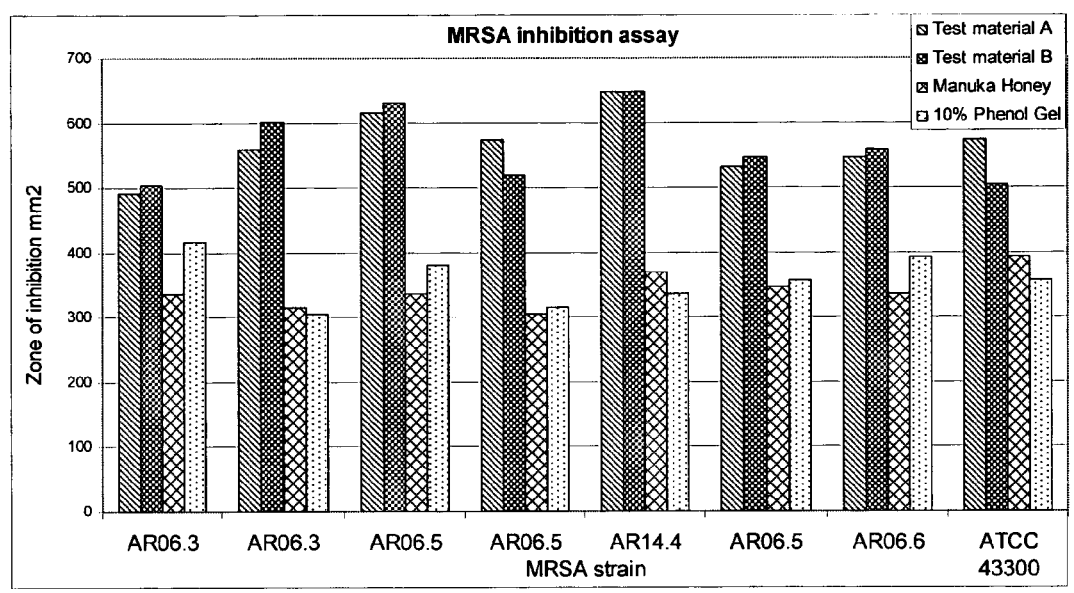
Figure 11A:
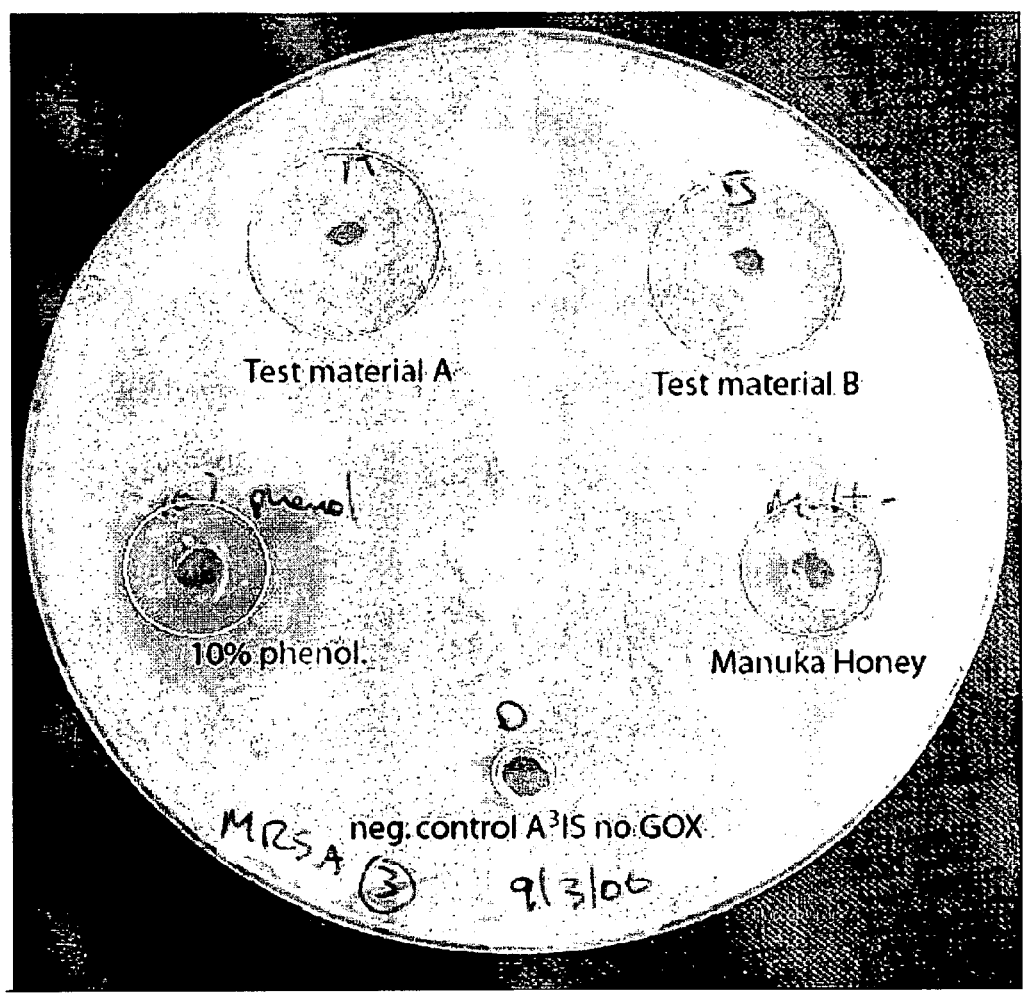

The Antimicrobial System formulation is shown to have antimicrobial activity against 8 strains of MRSA on three different days and compared to a 10% phenol standard and to Manuka honey FIG. 10. Formulation $A^3IS$ is at normal pH 5.5 (test material A) and pH 7 (test material B), a negative control $A^3IS$ containing no GOX is included. The results demonstrate significant in vitro anti-MRSA efficacy and the superiority of $A^3IS$ over Manuka honey and a 10% phenol gel control. Zones of inhibition are shown in FIG. 11a. Test material A is adjusted to pH 5.5 and test sample B is adjusted to pH 7. FIG. 11a shows the enhanced results of $A^3IS$ which is approximately 300% better than the Manuka honey. This clearly shows that the $A^3IS$ has superior and advantageous properties over and above Manuka honey.

Example 11

Figure 11B:
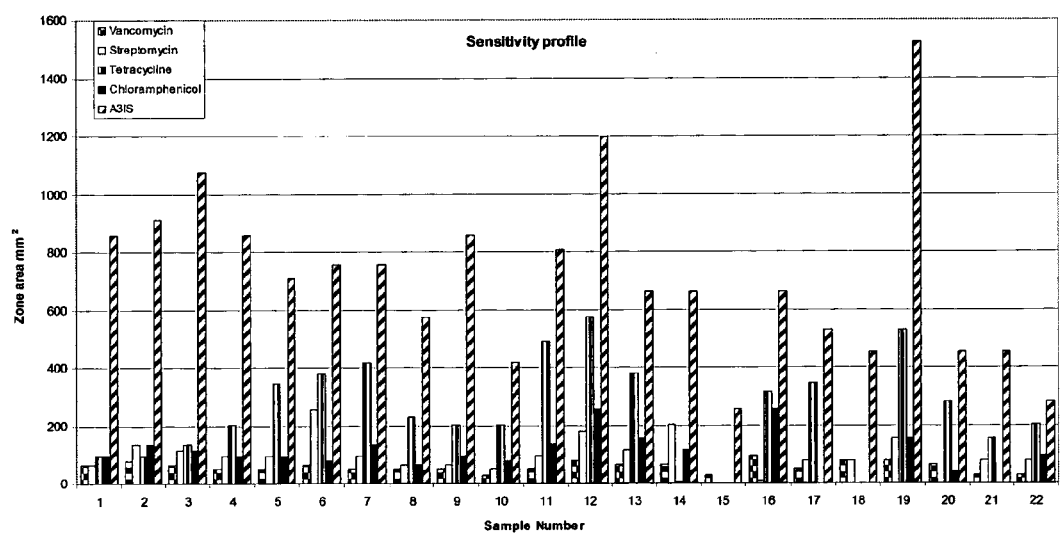

$A^3IS$—Potent Antimicrobial Activity Against Clinical Isolates of Mastitis and Retention of Activity in Raw Milk FIG. 11b shows the results of an inhibition assay (3 day repeats) for A3IS and four antibiotics (Vancomycin, Streptomycin, Tetracycline and Chloramphenicol) when tested against 22 clinical isolates of Mastitis causing *Staphylococcus aureus* organisms. Formulation $A^3IS$ demonstrates superior in vitro efficacy to all of these antibiotics. Clinical isolate number 15 is resistant to Vancomycin, Streptomycin and Tetracycline and shows only mild sensitivity to Chloramphenicol, however, it demonstrates sensitivity to A3IS.

Figure 11C:
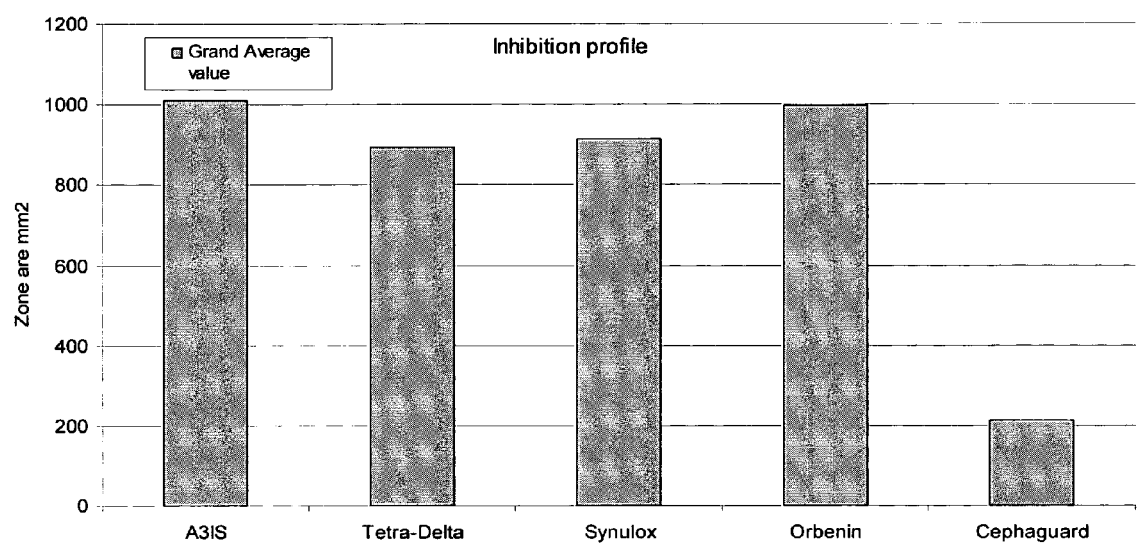

FIG. 11c shows the results of an inhibition assay (3 day repeats) for $A^3IS$ when tested against 22 clinical isolates of Mastitis causing *Staphylococcus aureus* organisms. Formulation $A^3IS$ demonstrates comparable in vitro efficacy to three of the leading commercially available multi antibiotic products for Mastitis and is superior to one of these products.

Figure 11D:
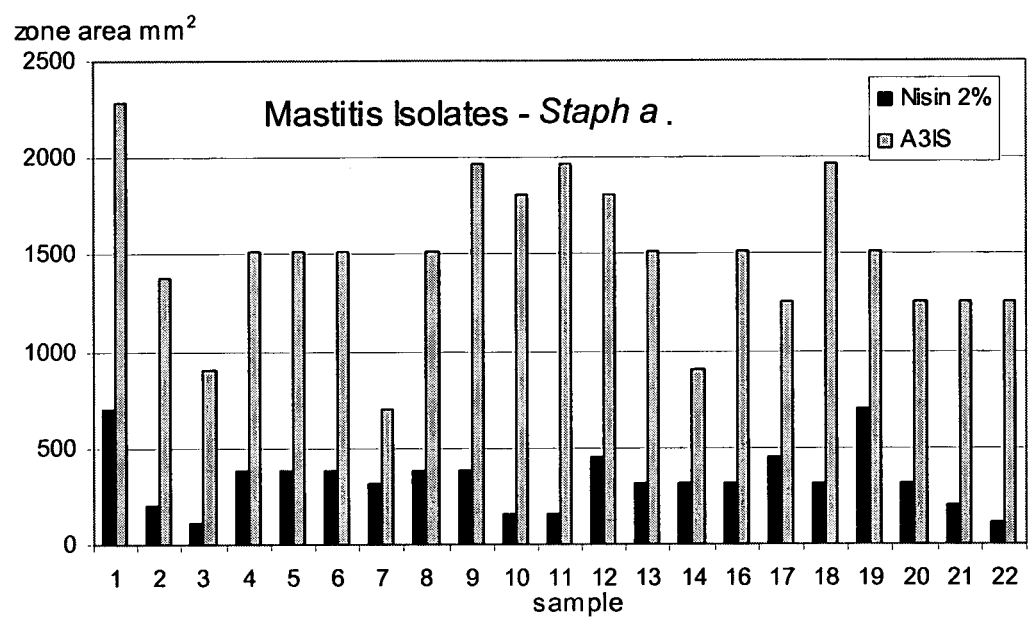

FIG. 11d shows the results of an inhibition assay (3 day repeats) for $A^3IS$ tested against a 2% Nisin solution on 21 clinical isolates of Mastitis causing *Staphylococcus aureus* organisms. Formulation $A^3IS$ demonstrates superior in vitro efficacy to the 2% Nisin solution. Note: Clinical isolate number 15 of FIG. 11b was unrecoverable from storage and is not included in this assay.

Figure 11E:

FIG. 11e shows the presence of a 2% Nisin resistant colony within the zone of inhibition during a Nisin efficacy study. $A^3IS$ resistant colonies have never been observed in efficacy studies based on zone of inhibition assays, nor has regrowth of cultures occurred following spectrophotometric based $A^3IS$ inhibition assays.

Five mls of raw milk is inoculated with 0.1 mls of an overnight culture of *Staphylococcus aureus* (containing approximately $5 \times 10^7$ cfu/ml) followed by the addition of 0.5 mls of $A^3IS$ formulation. This mixture is incubated overnight at 37° C. The mixture is then analysed for $H_2O_2$ production and survival of the inoculated *Staphylococcus aureus*. Levels of $H_2O_2$ in excess of 100 mg/l are detected in this milk and few of the inoculated *Staphylococcus* are recovered. The mixture shows no sign of souring which would be expected following overnight incubation at this temperature. By contrast, raw milk to which the $A^3IS$ is not added sours and coagulates. This finding indicates $A^3IS$ retains activity even in a complex medium such as raw milk Example 12

$A^3IS$—In-Vitro Toxicity/Irritancy Measurement

Toxicity/irritancy is determined using normal human fibroblasts (NHFs ECACC 90011807) and normal human keratinocytes (NHKs CC-2501) grown in Eagles Minimum Essential Medium (EMEM) with, 2 mM L-Glutamine, 10% Foetal Bovine Serum (FBS), incubated at 370 C in 5% CO2. Three repeats of two dimensional assays using 24 and 12 well plates, utilising both neutral red and 3-(4,5-Dimethyl-thiazol-2-yl)-2,5-diphenyltetrazolium bromide (MU), Sigma., 'In Vitro Toxicology Assay Kit' for direct contact cell assays are performed, to assess viability after incubation with test materials for 8 hrs (sodium azide—positive control, concentrations of silver gel, zinc gel, A3IS and fresh media—negative control).

ISO 10993, agar overlay tests for cytotoxicity: in vitro method is also used, employing L929 cells (mouse fibroblasts ECACC 85011425). In brief; a confluent monolayer of cells is incubated, this is then covered with a layer fresh medium (EMEM, 2 mM L-Glutamine, 5% FBS, 2% Penicillin-Streptomycin) containing 1.5 g/l of soft agar and allowed to solidify. One tenth of the surface is covered with test materials (previously described) and incubated for 24 hrs. Post incubation the test material is carefully removed and a vital stain (neutral red) in fresh media added. After incubation this is removed, the cells washed and then the dye extracted from the cells and quantified spectrophotometrically for cell viability.

A three dimensional dermal skin model (Skinethic, France) is also employed to determine the irritant effect of the formulation and controls on differentiated keratinocytes as in the stratum corneum, a cultured skin equivalent. The assay employs a three dimensional epidermal skin model and is carried out at several time points. The reconstituted human epidermis model consists of an airlifted, living, multi-layered epidermal tissue construct, produced in polycarbonate inserts in serum-free and chemically defined medium, featuring normal ultra-structure and functionality equivalent to human epidermis in vivo. Quadruplicate in vitro reconstituted human epidermis tissues, age day 17, (size 0.63 $cm^2$) are dosed topically with 2-10 mg/$cm^2$ of the formulation for 3 and 24 hours and tissue viability assessed using MTT assay, using the German Federal Institute for Risk Assessment (BFR-ZEBET) validated protocol.

Cell culture supernatant from the irritancy assay described previously is analysed using an IL-1 Enzyme-Linked Immuno Sorbent Assay (ELISA) (R&D Systems) and a Lactate Dehydrogenase (LDH) ELISA (R&D Systems), for cytokine and enzyme measurement to assess immunostimulatory and irritant effect of test materials.

Cross sections of the 3D skin models used for the irritancy assay are stained with haematoxylin and eosin (H&E), The Technical Procedure Included:

Fixation: The tissues are mechanically and biochemically stabilised in a fixative. The fixative is neutral buffered formalin, 10% formaldehyde in phosphate buffered saline (PBS).

Embedding: The technique used is wax embedding. The samples are progressively immersed in increasing concentrations (20%, 30%, 40%, 50%, 80% and 100%) of pure ethanol to dehydrate the tissue, followed by a clearing agent, xylene (100%), and finally hot molten paraffin wax (impregnation) and allowed to cool and harden.

Sectioning: The sample tissue is then sectioned into 5 micrometer sections using a microtome. These slices are then placed on a glass slide for staining.

Staining: To view the tissue under a microscope, the sections are stained with hematoxylin and eosin (H&E) to asses the rate of surface epidermal degradation caused by each test material.

Figure 12A:
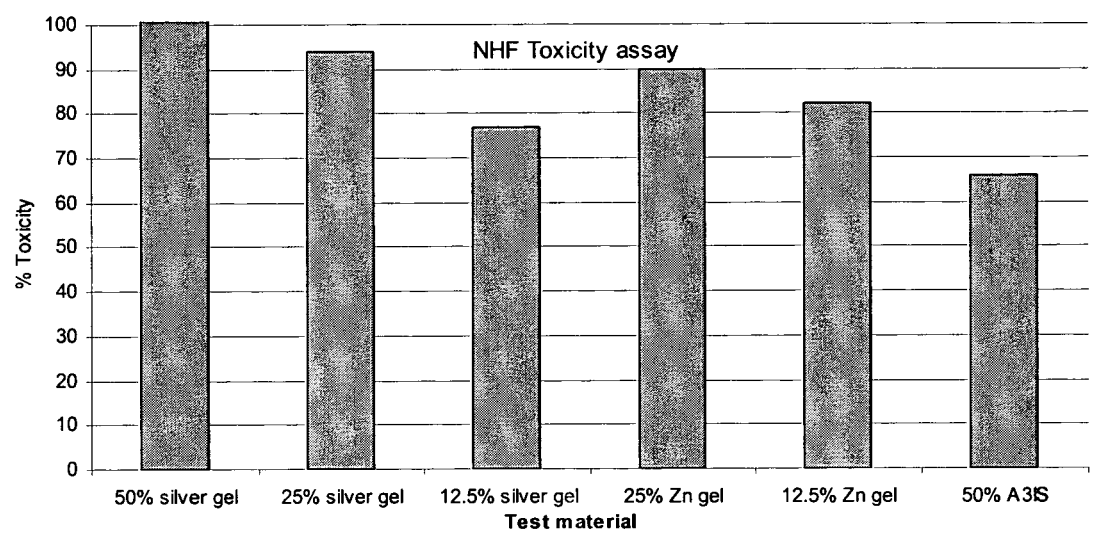
FIG. 12d shows A³IS and other test material MTT irritancy assay over a 24 hour period employing the Skinethic® 3D skin model. A³IS demonstrates less irritancy in this three dimensional assay than the commercially available products tested.
FIG. 12e shows Haematoxylin/Eosin (H&E) stained cross section of Skinethic® 3D skin exposed to the comparative silver containing gel product. Note that the silver formulation causes detachment of the epidermal layer from the basal layer.
FIG. 12f shows Haematoxylin/Eosin (H&E) stained cross section of Skinethic® 3D skin exposed to the comparative silver containing gel product. Note that the silver formulation causes detachment of the epidermal layer from the basal layer.
FIG. 12g shows Haematoxylin/Eosin (H&E) stained cross section of Skinethic® 3D skin exposed to A³IS, Note that A³IS does not cause detachment of the epidermal layer from the basal layer.
FIG. 12h shows Haematoxylin/Eosin (H&E) stained cross section of Skinethic® 3D skin exposed to A³IS, Note that A³IS does not cause detachment of the epidermal layer from the basal layer.
Figure 12B:
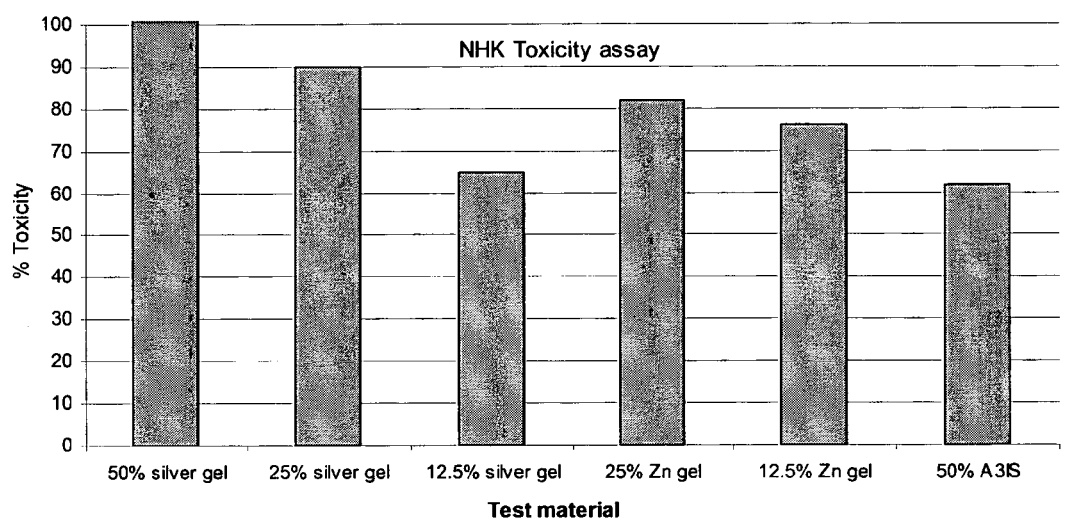

FIG. 12a and FIG. 12b show the results of the initial toxicity assessment of $A^3IS$ by means of the MTT viability assays on NHFs (Normal Human Fibroblasts) and NHKs (Normal Human Keratinocytes). Percent toxicity was calculated according to the formula: % Toxicity=1−(OD average of test material wells/average OD of corresponding control wells (no test material added))×100. Included in the assay are a 50% concentration of A3IS, a range of concentrations of a commercial silver containing gel and a commercial zinc containing gel product, compared to sodium azide (positive control). For the toxicity assay the concentration of test material used was twice that used for the irritancy assay, a 100 mg per well and the contact time was extended to 8 hrs.

Figure 12C:
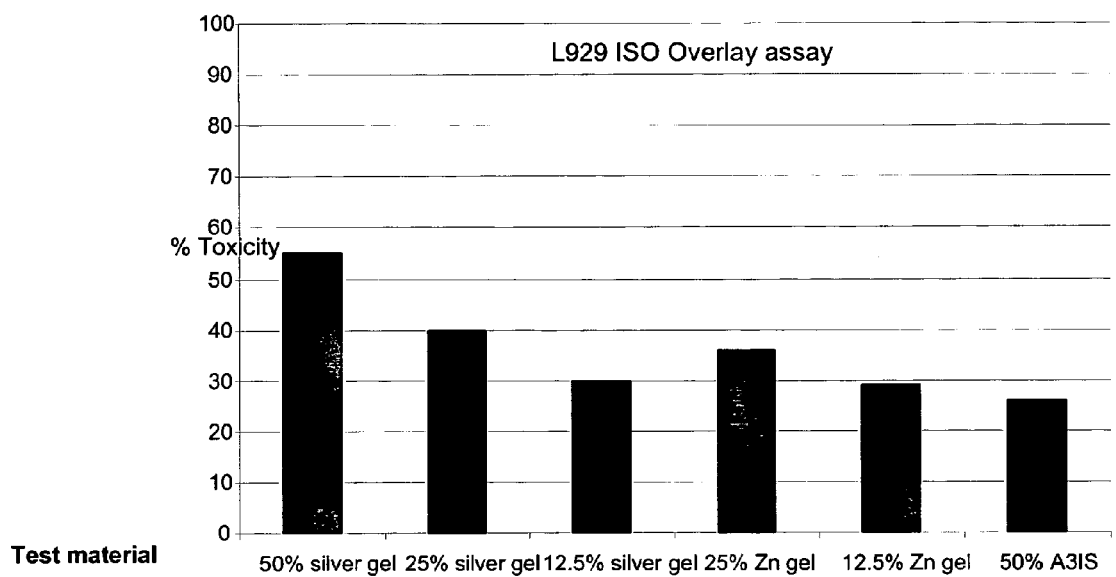

FIG. 12c shows the results of the ISO International Standard, 10993-5 agar overlay assay for cytotoxicity over 24 hrs using neutral red on L929s. Percent toxicity was calculated according to the formula: % Toxicity=1−(OD average of test material wells/average OD of corresponding control wells (sodium azide added))×100. Included in the assay are a 50% concentration of $A^3IS$, a range of concentrations of commercial silver containing gel and commercial zinc containing gel product, compared to sodium azide (positive control). The sodium azide positive control gives 100% toxicity. For the agar overlay toxicity assay the amount of test materials used was similar to that used for the initial direct contact assays of 100 mg per well however the contact time was extended to 24 hrs.

Figure 12D:
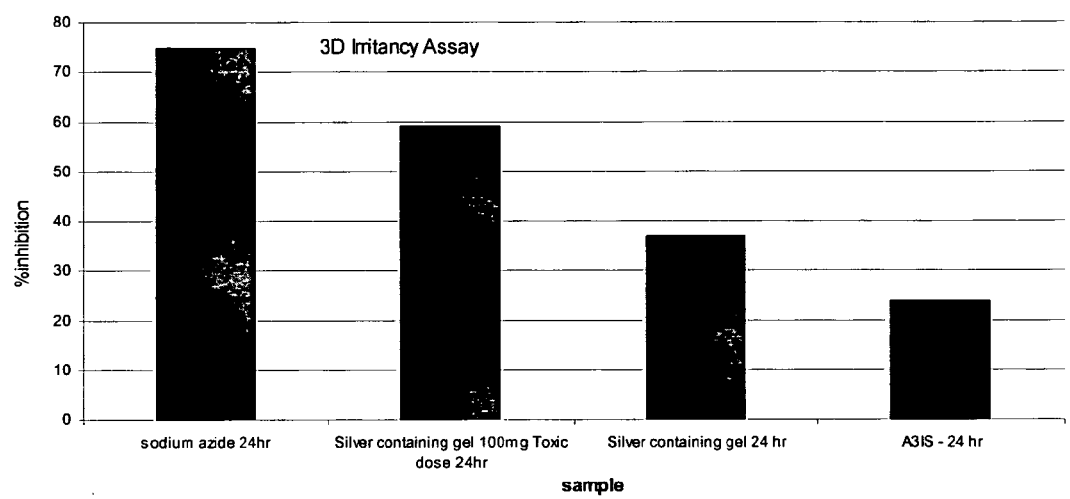
Figure 12E:
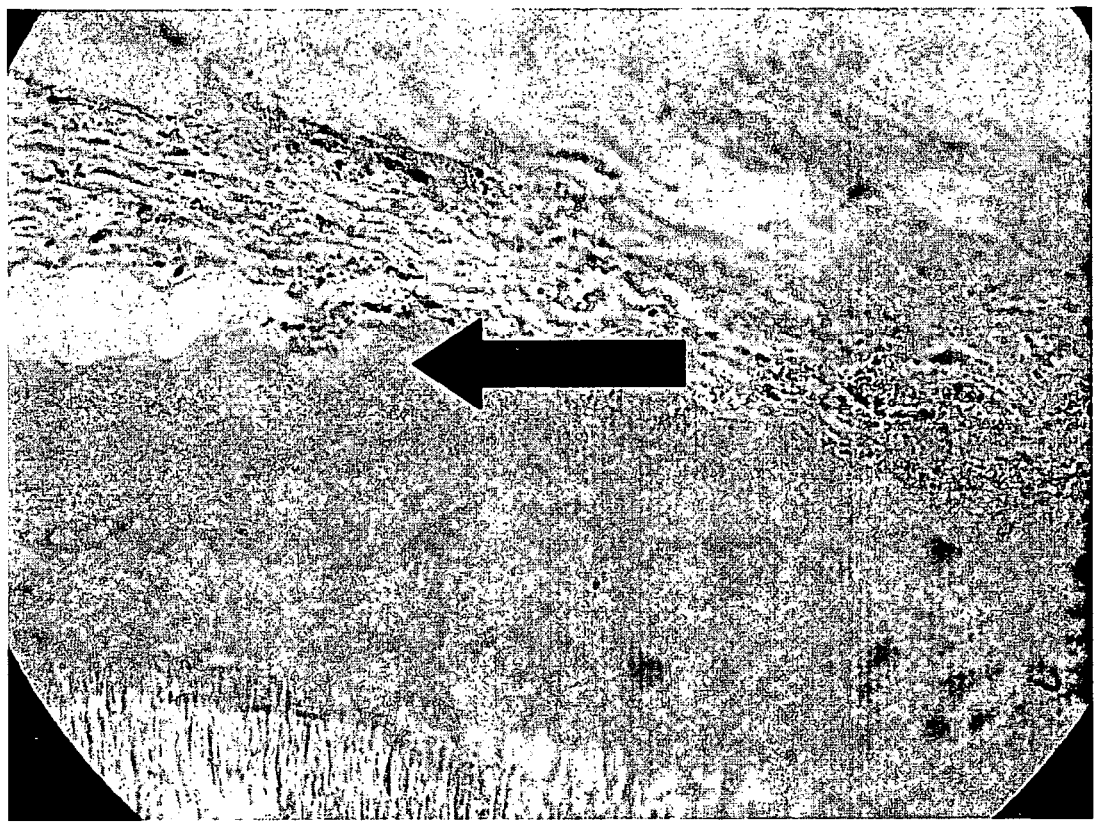
Figure 12F:
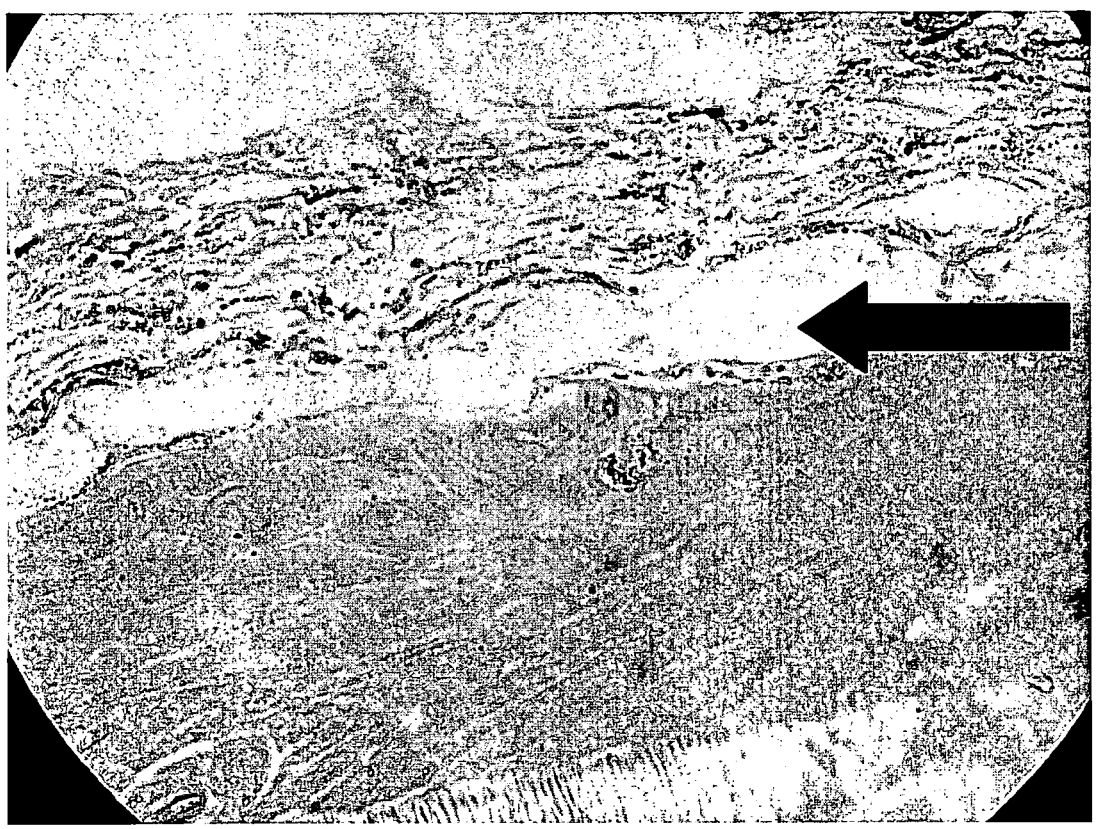
Figure 12G:
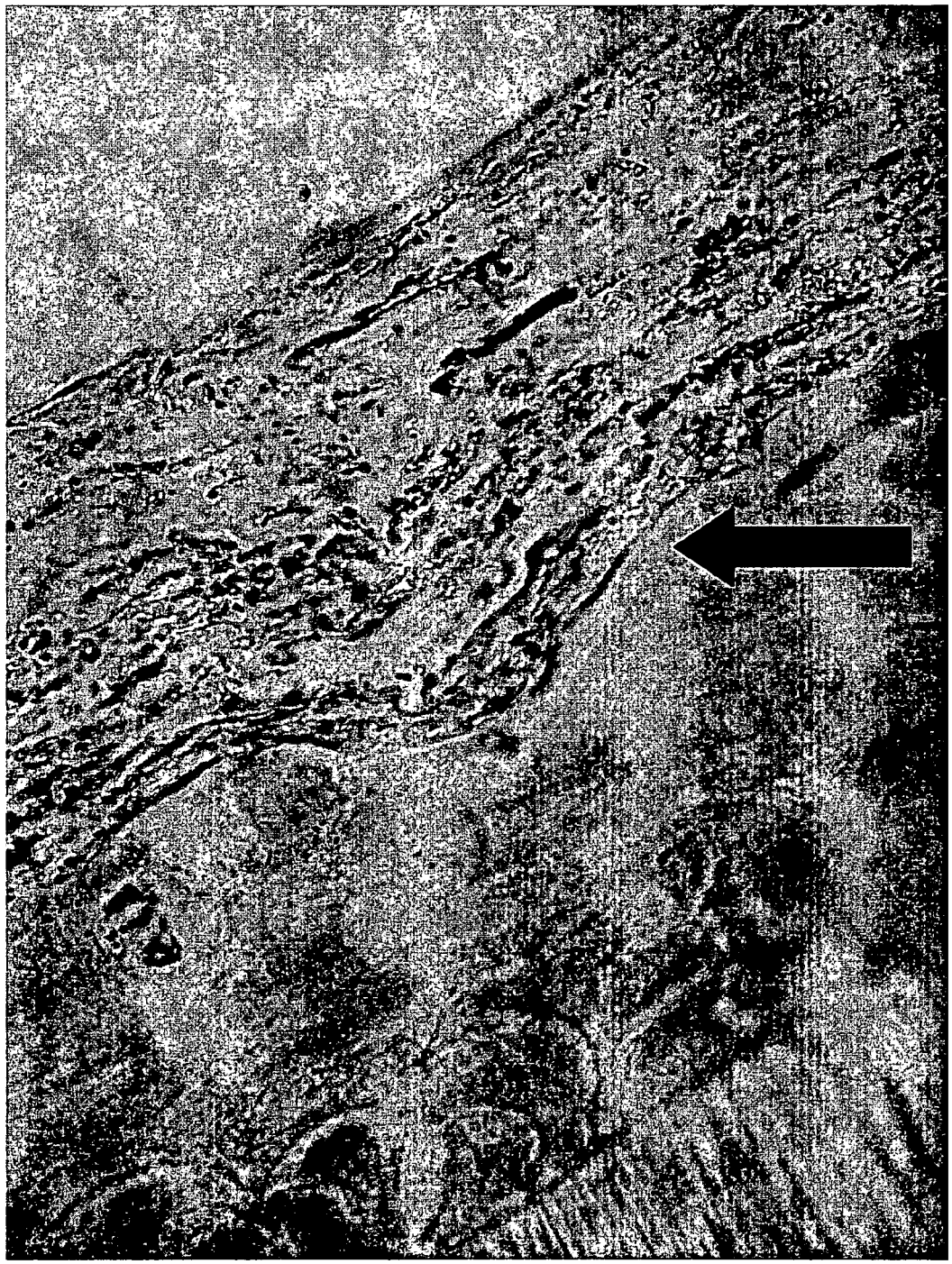
Figure 12H:
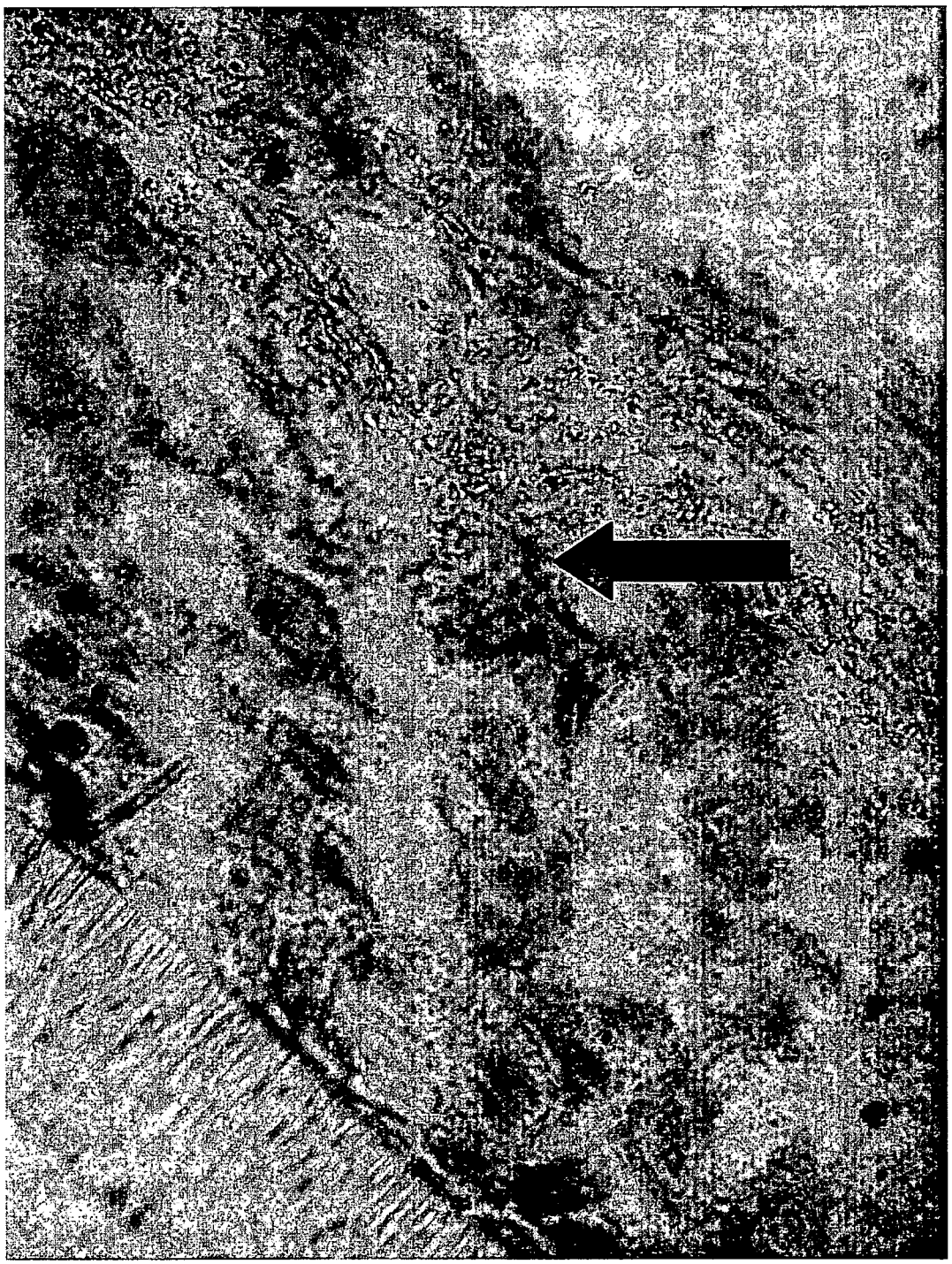

The results of an irritancy assay of the test materials for a range of contact times employing Skinethic® 3D skin model are shown in FIG. 12d. This reconstituted human epidermis model consists of an airlifted, living, multilayered epidermal tissue construct, produced in polycarbonate inserts in serum-free and chemically defined medium, featuring normal ultra-structure and functionality equivalent to human epidermis in vivo. The effects of this direct contact on the 3D skin samples are shown on Haematoxylin/Eosin (H&E) stained cross sections in FIG. 12e and FIG. 12f for the comparative silver containing gel product. FIG. 12g and FIG. 12h show H&E stained cross sections following $A^3IS$ formulation direct contact on the 3D skin samples. The results show that the silver formulation causes detachment of the epidermal layer from the basal layer, whereas the sample $A^3IS$ formulation exhibits no damage.

Quadruplicate in vitro reconstituted human epidermis tissues, age day 17, (size 0.63 cm$^2$) were dosed topically with 2-10 mg/cm$^2$ of the formulation for 3 and 24 hours and tissue viability assessed using MU assay, using the German Federal Institute for Risk Assessment (BFR-ZEBET) validated protocol. Percent irritancy was calculated according to the formula: % Irritancy=1−(OD average of test material skins/average OD of corresponding control skins (no test material added))×100. $A^3IS$ demonstrates less irritancy in this three dimensional assay than the commercially available products tested.

Example 13

$A^3IS$—Induction of Inflammatory IL-1 Release from Skin Cells

FIG. 13a shows the results of an ELISA assay of the supernatant removed during the 3D irritancy assay over a 48 hour period, measuring and comparing the release of IL-1 when exposed to $A^3IS$ formulation, to a sodium azide positive control, and a commercial silver containing gel product. The results indicate that IL-1 is released from the skin cells exposed to the $A^3IS$ formulation. FIG. 13b Illustrates the measurement of released Lactate Dehydrogenase (LDH) in the cell media used during the irritancy test protocol. Results show LDH release by cells following exposure to the $A^3IS$ formulation, a sodium azide positive control, and a commercially available silver containing gel product. Lactate dehydrogenase is released by cells exposed to destructive compounds. The results indicate that the $A^3IS$ formulation is less toxic than commercially available silver containing gel products.

Example 14

$A^3IS$—Terminal Sterilisation $A^3IS$ was filled into glass bottles and plastic tubes. These were then sterilised by Gamma irradiation. Post sterilisation, the samples antibacterial activity was compared to pre sterilisation results. It was found that Gamma irradiation did not reduce activity. There was slight discolouration of the primary container; however the irradiation process did not affect the activity or the colour of the test material FIG. 14 shows the efficacy of $A^3IS$ prior to and after gamma irradiation on *S. aureus, E. coli* and *Pseudomonas aeruginosa*.

Example 15

$A^3IS$—Incorporation in a Collagen—GAG (Glycosaminoglycan) Matrix—as an Antibacterial Dressing Picture of $A^3IS$ in GAG on *S. aureus* and pictures of the infiltration of GAG (FIG. 15a to FIG. 15c).

Collagen—GAG (glycosaminoglycan) matrix as has been previously described (Wilkins, L., M., et al, 1993. Development of a bilayered Living Skin Construct for Clinical Applications. Organogenesis Inc.) is formulated and A3IS was added to this matrix at a ratio of 1:1.

The mixture is poured onto a sterile surface to form a thin layer of approx 1 mm and dried in an incubator for 24 hrs to form a skin dressing. Once dry, 1 cm sections are cut, and placed onto inoculated agar plates inoculated with *S. aureus, E. coli* and *P. acnes*. Antibacterial activity against *S. aureus, E. coli* and *P. acnes* is observed. There are clear defined zones of inhibition and no bacterial growth is observed under the dressing.

The test sections are also placed onto a confluent monolayer of NHFs (normal human fibroblasts) in 6 well plates at time $T_0$. It is found that there was little to no toxicity.

The test sections were also co-incubated with NHF cells, in cell culture wells. It was found that in addition to adhering to the bottom of the cell culture wells, as was expected, the NHF cells also infiltrated, attached to and grew on the test sections. This demonstrates that Collagen—GAG matrices incorporating A³IS are suitable matrices for cell attachment and growth (see FIG. 15*b* and FIG. 15*c*).

Example 16

A³IS—Incorporation in an Alcoholic Gel

A³IS is mixed with an alcoholic gel consisting of absolute alcohol, ultrez 10 gelling agent, di-isopropanolamine and propylene glycol, which is mixed prior to the addition of A³IS resulting in a clear non-adhesive material. This gel formulation is tested using the well diffusion and surface diffusion bio assay to determine zones of inhibition against *S. aureus, E. coli* and *P. acnes*. Results are shown for *S. aureus* FIG. 16*a*. It should be noted that the zones of inhibition are artificially low in this situation due to the absorptive property of the gel matrix, thus not allowing free diffusion through the agar matrix but there is a clear zone around the gel matrix.

The gel formulation is put on a short term stability study of 6 weeks, including a freeze thaw test. Results indicated that the gel formulation maintained stability throughout the test period FIG. 16*b*. Results are shown for *S. aureus*.

Example 17

A³IS—Incorporation onto Commercially Available Wound Dressings

Picture of A³IS in wound dressings FIG. 17

Formulation A³IS was poured onto the surface of a range of commercially available dressings Kaltostat® (Comvita), Kendal® (Telfa) and a Collagen—GAG (glycosaminoglycan) matrix as previously described and allowed to diffuse into the dressing for several hours to form a thin layer of approximately 1 mm. 1 cm2 sections were cut and placed onto agar plates, previously inoculated with *S. aureus, E. coli* and *P. aeruginosa*. The antibacterial efficacy of A³IS impregnated dressings was then compared to Aquacel® (Convatec) and Betadine® (Seton) commercially available dressings that contain elemental silver and iodine FIG. 17. It was found that the A³IS dressings are as effective antimicrobially as Aquacel (Convatec) and Betadine® (Seton) and a commercially available dressing that use elemental silver and iodine.

Example 18

A³IS—Potent Antimicrobial Activity Against Onychomycosis

A case study on the efficacy of A³IS in the treatment of fungal nail infections was carried out on a human volunteer. The infected nail was the big toe nail on the right foot and the infection was localised on the left side of the nail. The infection had been present for a considerable period of time, approximately 2 years. Prior to treatment, a photograph of the infected nail was obtained FIG. 18*a*. The treatment was carried out once daily in the morning, subsequent to the subject having a shower and toweling dry. A³IS was applied to the surface of the nail over the infected region rather than over the entire nail surface. A³IS was then covered with a bandage whose wadding had been moistened using water and the nail was therefore covered in an occlusive dressing for the rest of the day FIG. 18*b*. This treatment was carried out daily for a period of three weeks. After a period of two days, another photograph was taken FIG. 18*c*. It is evident that the infected region of the nail has changed appearance in that it is now darker in colour. During the period of treatment, there was little evidence of further physical alteration except the development of an increasingly larger section of un-infected nail growing out. A further photograph 8 weeks after initiation of the treatment is shown FIG. 18*d*. In this the band of uninfected nail is clearly visible, indicating that the dermatophytes have been eliminated.

The invention claimed is:

1. A storage-stable antimicrobial and immunostimulatory formulation comprising glucose oxidase, D-glucose, additional sugars selected from one or more of sucrose, fructose or maltose and hydrogen peroxide in an aqueous solution;
    wherein glucose oxidase is present in an amount sufficient to provide an activity of at least 10 U per 100 g of the formulation;
    D-glucose is present from 20 to 85% by weight based on the weight of the total formulation;
    additional sugars selected from one or more of sucrose, fructose or maltose are present from 5 to 70% by weight based on the weight of the total formulation;
    water is present from 10 to 20% by weight based on the weight of the total formulation;
    the formulation has a pH from approximately 4 to 8;
    and wherein the formulation provides a two-stage hydrogen peroxide release in which
        storage-stable endogenously produced hydrogen peroxide is bioavailable within the formulation at a level of at least 10 mg per liter for immediate release; and
        the sustained release of further hydrogen peroxide for at least a twenty-four hour period occurs upon administration or application of the formulation.

2. The formulation of claim 1 wherein the additional sugars are present from 10 to 70% by weight based on the weight of the total formulation.

3. The formulation of claim 1 wherein fructose is present from 8 to 50% w/w %, maltose is present from 4 to 15 w/w %, sucrose is present from 0.5 to 3 w/w % based on the weight of the total formulation.

4. The formulation of claim 1 wherein the additional sugars and D-glucose are present at a ratio of approximately 0.05:1 to 3.5:1.

5. The formulation of claim 1 wherein the storage-stable endogenously produced hydrogen peroxide is bioavailable within the formulation at a level of at least 75 mg per liter for immediate release.

6. The formulation of claim 1 wherein the level of sustained release hydrogen peroxide produced upon rehydration of the formulation is at least 10 mg per liter.

7. The formulation of claim 1 further comprising a buffering agent.

8. The formulation of claim 7 wherein said buffering agent is selected from carbonic acid-bicarbonate, phosphoric acid and disodium hydrogen phosphate.

9. The formulation of claim 1 further comprising at least one viscosity modifying ingredient.

10. The formulation of claim 1 with a pH from approximately 5 to 7.

11. The formulation of claim 1 in a form suitable for topical, enteral or parenteral administration.

12. The formulation of claim 1 in the form of a topical ointment, cream, lotion, oil, liniment, liquid or gel.

13. The formulation of claim 12 wherein said formulation is in a form suitable for intramammary administration.

14. The formulation of claim 12 wherein said formulation is formulated to be part of a teat seal, tissue, bandage or dressing.

15. The formulation of claim 1 in a form adapted for delivery via a dissolvable film strip or strips, dental floss, toothpaste, mouthwash or mouth guards.

16. A storage-stable antimicrobial and immunostimulatory formulation of claim 1, wherein the D-glucose is present from approximately 26% to 43% by weight based on the weight of the total formulation;
sucrose is present between 0.5% to 2.5% by weight based on the weight of the total formulation;
fructose is present between 30% to 40% by weight based on the weight of the total formulation; and
maltose is present between 5% to 15% by weight based on the weight of the total formulation.

17. The formulation of claim 16 wherein the D-glucose is present from approximately 33% to approximately 43% by weight based on the weight of the total formulation.

18. The formulation of claim 16, wherein the maltose is present between 5% and 9%.

19. The formulation of claim 1 wherein the level of sustained release hydrogen peroxide produced upon administration or application of the formulation is 20 mg per liter.

20. A storage-stable antimicrobial and immunostimulatory formulation containing glucose oxidase, D-glucose, sucrose, fructose, maltose and hydrogen peroxide in an aqueous solution and an optional buffering agent;
wherein an effective amount of glucose oxidase is present in an amount sufficient to provide an activity of at least 10 U per 100 g of formulation;
wherein the D-glucose is present from approximately 33% to approximately 43% by weight based on the weight of the total formulation;
sucrose is present between 0.5% to 2.5% by weight based on the weight of the total formulation;
fructose is present between 30% to 40% by weight based on the weight of the total formulation;
maltose is present between 5% to 15% by weight based on the weight of the total formulation;
water is present from 10 to 20% by weight based on the weight of the total formulation;
the formulation has a pH from approximately 4 to 8; and
the formulation provides a two-stage hydrogen peroxide release in which
storage-stable endogenously produced hydrogen peroxide is bioavailable within the formulation at a level of at least 10 mg per liter for immediate release and
the sustained release of further hydrogen peroxide for at least a twenty-four hour period occurs upon administration or application of the formulation.

21. The formulation of claim 20, wherein the optional buffering agent is present in an amount effective to achieve a pH of from approximately 4 to 8.

* * * * *